(12) United States Patent
Pandia et al.

(10) Patent No.: US 9,462,956 B2
(45) Date of Patent: Oct. 11, 2016

(54) CALCULATING HEART RATE FROM ACCELERATION SIGNALS CONTAINING CARDIAC ACTIVITY SIGNALS

(71) Applicant: Texas Instruments Incorporated, Dallas, TX (US)

(72) Inventors: Keya R. Pandia, Stanford, CA (US); Sourabh Ravindran, Dallas, TX (US); Edwin Randolph Cole, Highland Park, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 65 days.

(21) Appl. No.: 14/667,160

(22) Filed: Mar. 24, 2015

(65) Prior Publication Data

US 2015/0196213 A1 Jul. 16, 2015

Related U.S. Application Data

(62) Division of application No. 12/861,874, filed on Aug. 24, 2010, now abandoned.

(60) Provisional application No. 61/242,688, filed on Sep. 15, 2009, provisional application No. 61/262,336, filed on Nov. 18, 2009, provisional application No. 61/262,331, filed on Nov. 18, 2009.

(51) Int. Cl.
*A61B 5/029* (2006.01)
*A61B 5/04* (2006.01)
*A61B 5/0402* (2006.01)
*A61B 5/11* (2006.01)
*A61B 5/00* (2006.01)
*A61B 7/00* (2006.01)

(52) U.S. Cl.
CPC .......... *A61B 5/04017* (2013.01); *A61B 5/029* (2013.01); *A61B 5/0402* (2013.01); *A61B 5/1102* (2013.01); *A61B 5/6831* (2013.01); *A61B 7/008* (2013.01); *A61B 2505/07* (2013.01); *A61B 2560/0475* (2013.01); *A61B 2562/0219* (2013.01)

(58) Field of Classification Search
CPC .......... A61B 2562/0219; A61B 5/113; A61B 5/0402; A61B 5/1118; A61B 5/6823; A61B 5/0205; A61B 5/08; A61B 5/1116; A61B 5/7239; A61B 5/0002; A61B 5/02416; A61B 5/0535; A61B 5/0809; A61B 5/0816
See application file for complete search history.

*Primary Examiner* — Rex R Holmes
(74) *Attorney, Agent, or Firm* — Lawrence J. Bassuk; Frank D. Cimino

(57) ABSTRACT

A heart monitor includes a single chest accelerometer (210), an analog signal conditioning and sampling section (215) responsive to said accelerometer to produce a digital signal substantially representing acceleration, and a digital processor (220) operable to filter the acceleration signal into a signal affected by body motion and to cancel the body motion signal from the acceleration signal, thereby to produce an acceleration-based cardiac-related signal. Other processes and electronic systems are also disclosed.

6 Claims, 40 Drawing Sheets

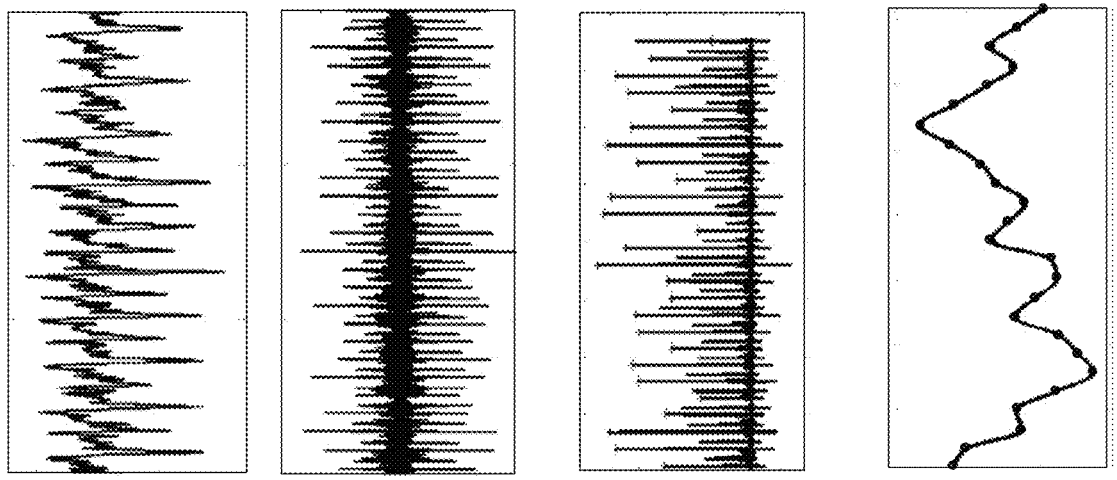
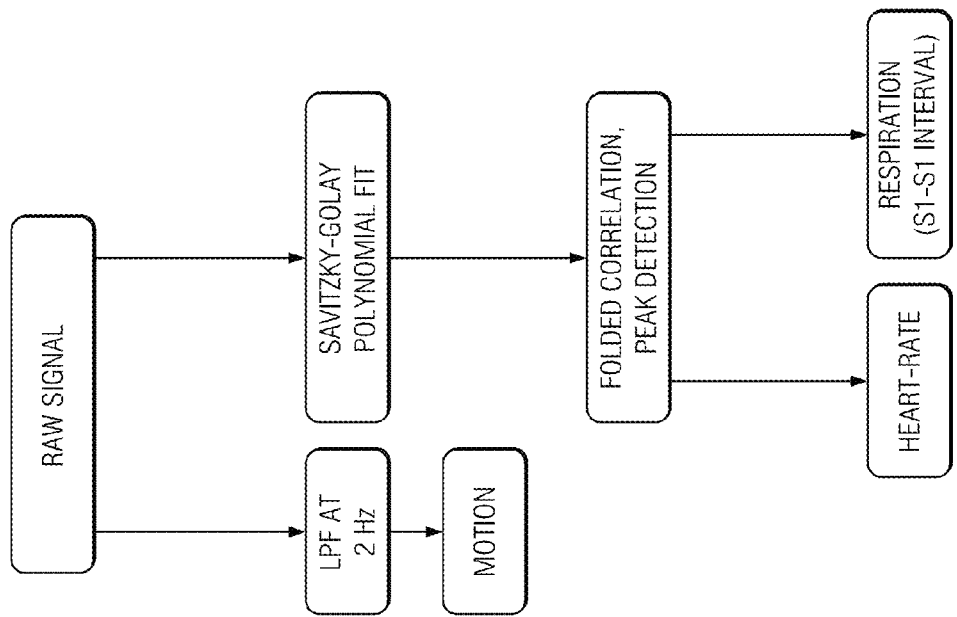
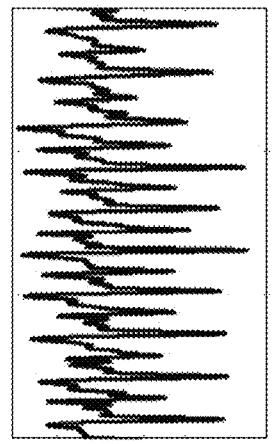
FIG. 14

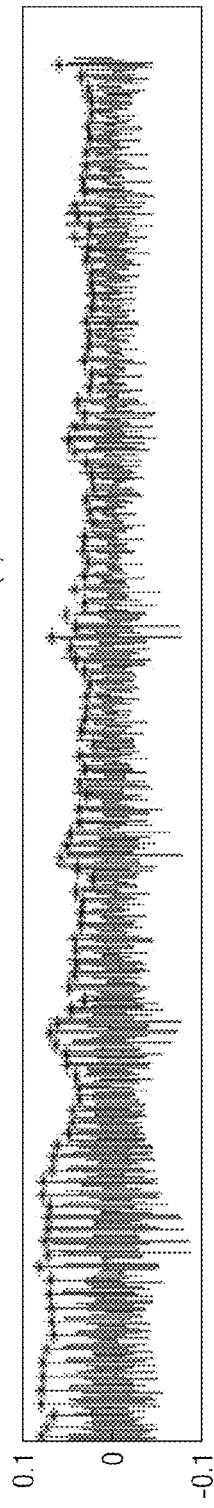
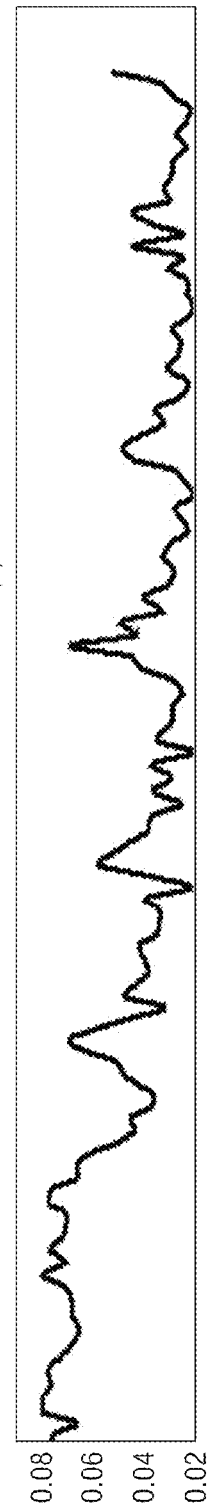
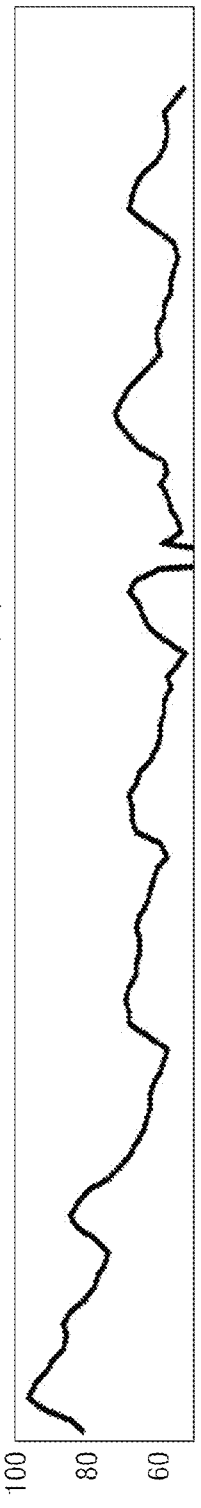
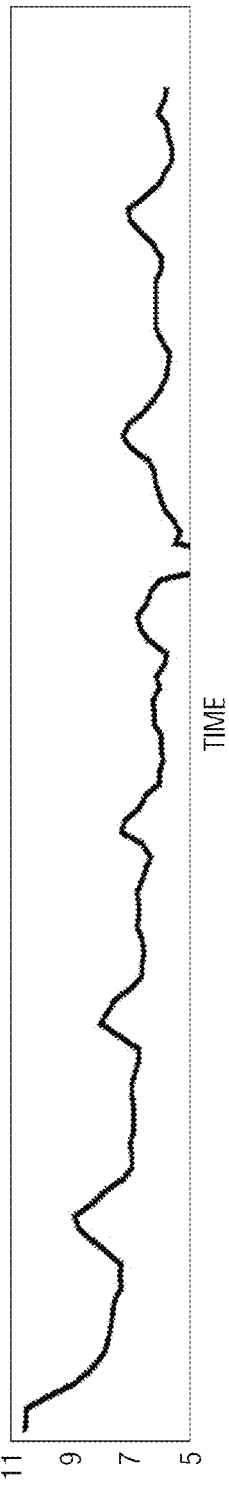
FIG. 35B

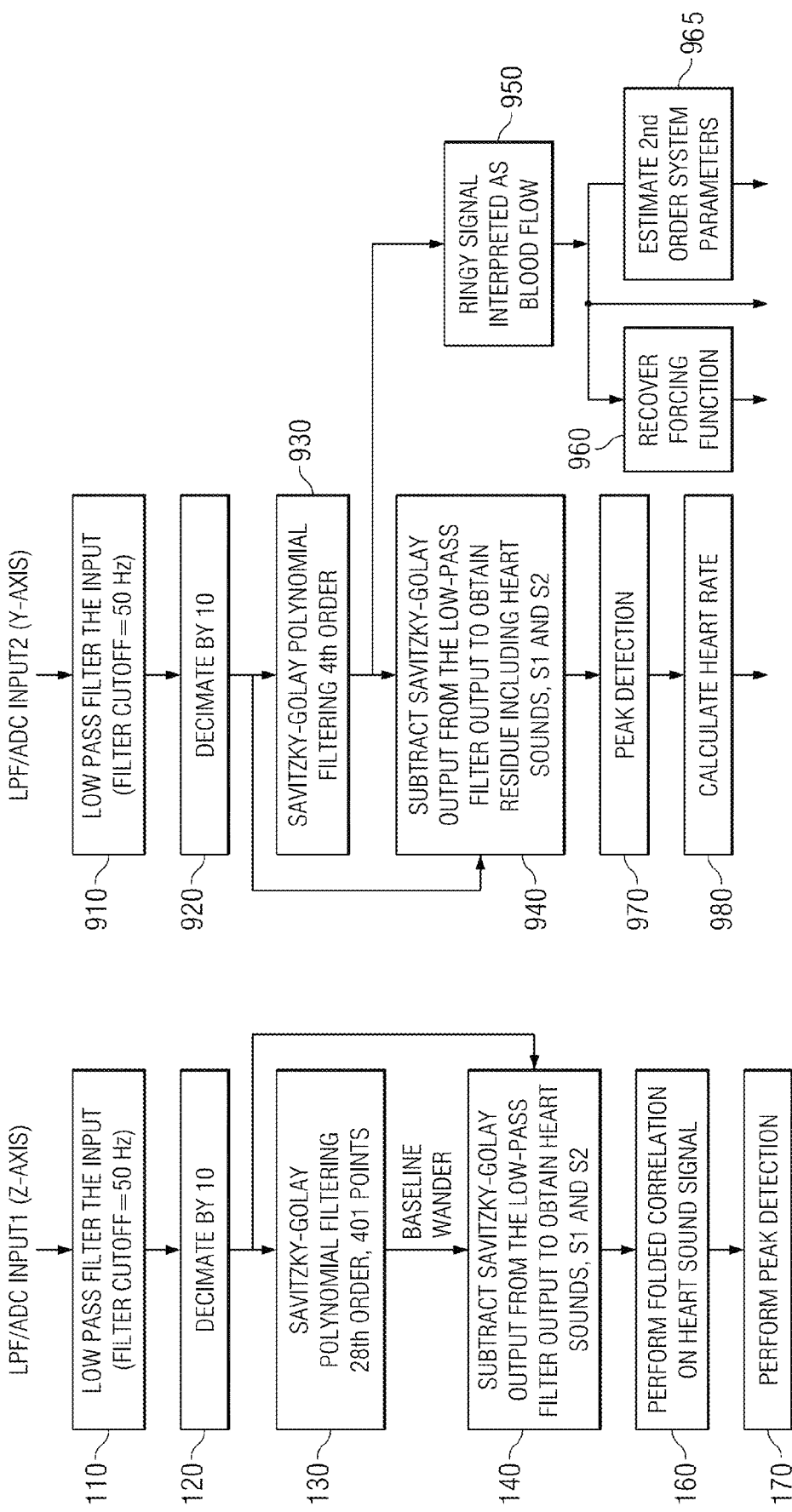

CALCULATING HEART RATE FROM ACCELERATION SIGNALS CONTAINING CARDIAC ACTIVITY SIGNALS

CROSS-REFERENCES TO RELATED APPLICATIONS

This application is related to U.S. patent applications as follows:

This application is a divisional of prior U.S. application Ser. No. 12/861,874, filed Aug. 24, 2010, now abandoned.

This application is related to U.S. patent application "Motion/Activity, Heart-Rate and Respiration From a Single Chest-Worn Sensor" Ser. No. 12/861,882 (TI-68552) filed Aug. 24, 2010 simultaneously herewith, which is incorporated herein by reference in its entirety.

This application is related to U.S. patent application "Motion/Activity, Heart-Rate and Respiration From a Single Chest-Worn Sensor" Ser. No. 12/861,882 (TI-68552) filed Aug. 24, 2010 simultaneously herewith which is incorporated herein by reference in its entirety.

This application is related to provisional U.S. patent application "Motion Artifact Cancellation to Obtain Heart Sounds from a Single Chest-Worn Accelerometer" Ser. No. 61/242,688 (TI-68518PS) filed Sep. 15, 2009, for which priority is claimed under 35 U.S.C. 119(e) and all other applicable law, and which is incorporated herein by reference in its entirety.

This application is related to provisional U.S. patent application "Motion/Activity, Heart-rate and Respiration From a Single Chest-worn Sensor" Ser. No. 61/262,336 (TI-68552PS) filed Nov. 18, 2009, for which priority is claimed under 35 U.S.C. 119(e) and all other applicable law, and which is incorporated herein by reference in its entirety.

This application is related to provisional U.S. patent application "Estimation of Blood Flow and Hemodynamic Parameters from a Single Chest-worn Sensor" Ser. No. 61/262,331 (TI-68553PS) filed Nov. 18, 2009, for which priority is claimed under 35 U.S.C. 119(e) and all other applicable law, and which is incorporated herein by reference in its entirety.

This application is related to provisional U.S. patent application "Heart Rate Detection In High Noise Conditions" Ser. No. 61/104,030 (TI-66732PS) filed Oct. 9, 2008, which is incorporated herein by reference in its entirety.

This application is related to U.S. Patent Application Publication "Heart Rate Detection In High Noise Conditions" 20100094150, dated Apr. 15, 2010 (TI-66732) which is incorporated herein by reference in its entirety.

This application is related to provisional U.S. patent application "Robust Heart Rate Detection in the Presence of Pathological Conditions" Ser. No. 61/023,581, filed on Jan. 25, 2008 (TI-65798PS), which is incorporated herein by reference in its entirety.

This application is related to U.S. Patent Application Publication "Method and System for Heart Sound Identification" 20090192401, dated Jul. 30, 2009 (TI-65798) which is incorporated herein by reference in its entirety.

This application is related to U.S. Patent Application Publication "Method and Apparatus for Heart Rate Monitoring" Ser. No. 12/768,488 filed Apr. 27, 2010 (TI-67877), which is incorporated herein by reference in its entirety.

This application is related to U.S. patent application "Parameter Estimation for Accelerometers, Processes, Circuits, Devices and Systems" Ser. No. 12/398,775 (TI-65353) filed Mar. 5, 2009, and which is incorporated herein by reference in its entirety.

This application is related to the US patent application titled "Processes for More Accurately Calibrating E-Compass for Tilt Error, Circuits, and Systems" Ser. No. 12/398,696 (TI-65997) filed Mar. 5, 2009, and which is incorporated herein by reference in its entirety.

STATEMENT REGARDING FEDERALLY SPONSORED RESEARCH OR DEVELOPMENT

Not applicable.

COPYRIGHT NOTIFICATION

Portions of this patent application contain materials that are subject to copyright protection. The copyright owner has no objection to the facsimile reproduction by anyone of the patent document, or the patent disclosure, as it appears in the United States Patent and Trademark Office, but otherwise reserves all copyright rights whatsoever.

FIELD OF TECHNOLOGY

The field of technology is in the areas of monitoring of the human body, automatic analysis and display of monitoring data locally for medical and other purposes and telecommunication remotely for tele-medicine, and processes, circuits and devices for body monitoring of heart function, circulatory function, respiration, or other physiological processes. Biomedical instrumentation and signal processing are further fields.

BACKGROUND

Ambulatory measurement of cardiac activity can facilitate home health monitoring of older adults and of patients with a history of cardiovascular conditions. Evaluating cardiovascular performance of patients in ICU (intensive care unit) and hospital settings, in mobile ambulances, and at accident and trauma sites also involves or can involve ambulatory cardiac measurement.

Most current solutions for heart rate monitoring involve cumbersome equipment, such as heart rate recording belts to be worn around the chest, electrocardiogram (ECG) electrodes and leads, and in most cases electrical contact to the skin. However, such methods remain obtrusive, and are not optimal for long-term and ambulatory monitoring.

An alternative method of heart rate measurement uses heart sounds, conventionally measured with stethoscopes or phonocardiograph.

Detection and early warning of risk factors for and any incident of heart failure is vitally important in medicine, allied medical fields, residential care-giving, exercise venues and other settings. Heart failure can be caused by, and is at risk in case of, coronary artery disease, hypertension, valve disorder, past myocardial infarction, muscle disorder, congenital heart conditions, etc.

Current solutions for not only heart rate monitoring but also respiration monitoring are believed to involve cumbersome and expensive equipment e.g., respiration and heart rate monitoring belts to be worn around the chest, spirometers and canulas to be worn around the mouth and nose, and electrocardiogram (ECG) electrodes and leads to be taped on the body. Not only are these solutions obtrusive and expensive, but may also be too restrictive to be well-suited for ambulatory monitoring.

Noise mixed with signals received by the sensors used in heart monitoring, respiration monitoring, body motion and other monitoring applications can adversely affect the accuracy of each type of signal. Accordingly, methods for robust detection and separation of such signals in noisy conditions are desirable. Accuracy of heart rate detection is important in many commercial heart monitoring applications (e.g., heart rate monitors in exercise equipment, personal heart rate monitors, etc.) and medical heart monitoring applications (e.g., digital stethoscopes, mobile cardiac monitoring devices, etc.).

Simpler, more economical and more efficient methods and devices are desirable in the art for obtaining, isolating, determining and monitoring resting data and ambulatory data, such as robust, accurate detection of heart rate, timings of heart sounds (S1 and S2) and pathological cardiac conditions, and robust detection of respiration in connection with respiratory and pulmonary disorders, as well as data on body motion and ambulatory data and activity data.

Conventional approaches to address the bodily motion signal separation and/or removal problem are believed to involve multi-signal adaptive algorithms that need an additional motion signal reference recording typically from a secondary sensor. Also, the reference signal needs to be reasonably well correlated to the motion picked up by the primary sensor. Such arrangements are very difficult to establish in a real setting and can cause poor rejection of the motion signal and body motion artifacts. Some conventional single-channel de-noising techniques reinforce all major signal peaks and fail to distinguish body motions from heart sounds.

In addition to medical-related applications, solving the above problems could also help monitor older adults for unexpected changes in gait, for falls, for syncope (fainting), for accidents and trauma incidents. Fitness monitoring at home, in exercise venues, and in institutional care settings could also benefit.

Hemodynamic data also challenge the art to find methods and devices for obtaining, isolating, determining and monitoring more simply, economically and more efficiently. Hemodynamics as discussed herein includes the study of blood flow-related data directly or indirectly related to blood flow, such as: heart stroke volume, cardiac output, pre-ejection period, contractility (ability of heart to contract, inotropy), and related causal or caused bodily dynamics such as exercise and exercise recovery, and the Valsalva maneuver (such as when pushing or straining while holding one's breath, or otherwise doing the maneuver in a medical test).

Measurement of blood flow, hemodynamics and cardiovascular performance is integral to a holistic assessment of an individual's health. Specifically, patients with past conditions of heart disease like heart failure (potentially arising out of one or more of many causes like coronary artery disease, heart valve or heart muscle disorders, past myocardial infarction, hypertension etc.) may need constant monitoring in order to improve a person's quality of life via timely and appropriate diagnostic interventions. While the physiological mechanisms underlying these conditions are fairly well understood, the technology to monitor these physiological vitals needs considerable improvement.

Most current solutions for the measurement of blood flow and other hemodynamic parameters are believed to involve cumbersome and expensive equipment e.g., Impedance Cardiography (calls for electrodes to be connected on the skin), Doppler Echo Cardiography, Continuous Blood Pressure Monitoring etc. Not only are these solutions obtrusive and expensive, but may also be too restrictive to be well-suited for ambulatory monitoring applications.

SUMMARY OF THE INVENTION

Generally, and in one form of the invention, a heart monitor includes a single chest accelerometer, an analog signal conditioning and sampling section responsive to the accelerometer to produce a digital signal substantially representing acceleration, and a digital processor operable to filter the acceleration signal into a signal affected by body motion and to cancel the body motion signal from the acceleration signal, thereby to produce an acceleration-based cardiac-related signal.

Generally, and in another form of the invention, a data communication system includes a short range wireless circuit, a modem, and a digital processor operable to digitally low-pass filter in response to the short range wireless circuit with a first rolloff frequency less than about one hundred Hertz (Hz) to produce a first signal, and the digital processor further operable to apply a smoothing filter procedure to produce a slow wander signal, and to cancel the slow wander signal from the first signal to produce a second signal, and to generate data based on counting peaks based on the second signal and feed a third signal representing the data to the modem.

Generally, and in a process form of the invention, an electronic process includes sensing an original signal with an accelerometer, digitally low-pass filtering in response to the original signal and with a rolloff frequency less than about one hundred Hertz to produce a first filtered signal including components among which is a slow wander, digitally smoothing-filtering in response to the first filtered signal according to a procedure that substantially follows the slow wander in the first filtered signal thereby to produce a slow wander signal, and canceling the slow wander signal from the first filtered signal.

Generally, and in a further form of the invention, an electronic signal processing system includes a streaming data interface, a nonvolatile memory holding instructions representing a filtering process and coefficients, and an electronic processor coupled to the nonvolatile memory to operate in accordance with the instructions, the processor having an input coupled to the streaming data interface for a streaming data signal including noise and operable to digitally electronically execute a smoothing-filter-based procedure on the streaming data signal by a multiply-accumulation with at least some of the coefficients stored in the nonvolatile memory, the coefficients and procedure of a type adapted to reduce the noise and to largely remove slow variations thereby to produce a residue stream, the streaming data interface having an output for a signal based on the residue stream.

Other monitors, processors, circuits, devices and communication systems and processes for their operation and manufacture are disclosed and claimed.

BRIEF DESCRIPTION OF THE DRAWINGS

FIG. 14 is a partially-flow, partially graphical depiction of an inventive process for FIG. 13 separating a respiration signal, a heart signal and a body motion signal from each other using a single chest sensor.

(FIG. 33 is on same sheet as FIG. 37.)

FIG. 35B is a voltage-versus-time graph of another four concurrent waveforms over about a minute for a Valsalva Release phase of a Valsalva maneuver; the first waveform representing the blood flow signal from inventive polynomial filtering of the accelerometer Y-axis as in FIG. 31 (right side), the second waveform representing peak amplitude PAmp of that blood flow signal from accelerometer Y-axis, the third waveform representing Stroke Volume, and the fourth waveform representing Cardiac Output.

FIG. 36A is a flow diagram of inventive process for separating a heart signal from body motion and noise using Z-axis sensor input such as for use in FIG. 31 or with FIG. 36B.

FIG. 36B is a flow diagram of inventive process for separating a heart signal as well as a blood signal from each other using Y-axis sensor input such as for use in FIG. 31 and for obtaining further hemodynamic data and other information from the single Y-axis of the chest sensor.

Corresponding numerals in different Figures indicate corresponding parts except where the context indicates otherwise. A minor variation in capitalization or punctuation for the same thing does not necessarily indicate a different thing. A suffix .i or .j refers to any of several numerically suffixed elements having the same prefix. A first, second, third, etc. waveform is referenced in top to bottom order for a given Figure.

DETAILED DESCRIPTION OF EMBODIMENTS

Some structure and process embodiments provide motion artifact cancellation or motion signal separation to obtain heart sounds from a single chest-worn accelerometer.

Miniature, high-sensitivity MEMS accelerometers are presently available. Here, such an accelerometer is incorporated into a single, chest-worn sensor for recording of signals including some related to heart sounds. (The latter signal components are also themselves sometimes called heart sounds herein. The term "heart sound" refers in an expansive way to a signal analogous to cardiac S1, S2, and/or heart murmur or other cardiac waveform features, obtained from the processing of accelerometer data or other sensor data, and not necessarily to an audible sound.)

However, a major challenge of ambulatory monitoring is the corruption of heart signals by body motion artifact signals and the confusion of such signals. In some measurements, the chest acceleration signal as picked up by the accelerometer 10 in FIGS. 1-3 had a rather slow varying, but very strong (20-50 mv peak-to-peak) motion component. Riding on top of this motion signal, was a higher frequency, but weaker (5-10 mv peak-to-peak) heart sound signal. Significant variability between subjects was observed in the frequency content of both the motion and the heart sounds. Also, the two signals—motion and heart sounds—are not entirely frequency separable. Thus, simple digital band pass filtering does not consistently work to separate them. Physical motion impulses from the feet couple very differently and in a non-stationary and non-correlated manner to sensors placed at different parts of the body and also to orthogonal axes of the same sensor. Accordingly, even using multiple sensors to cancel out an artifact is complicated or unreliable.

Figure 3:
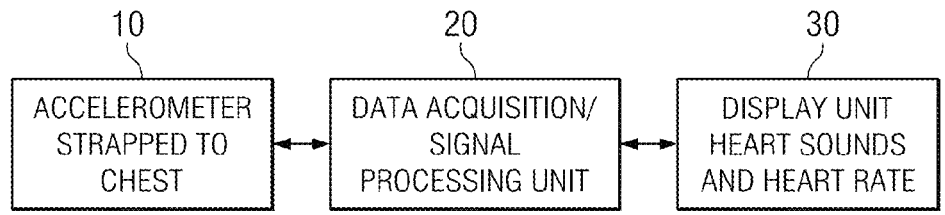
FIG. 3 is a block diagram of an inventive structure and process for separating a heart signal from body motion and noise using a single accelerometer chest sensor.
Figure 4:
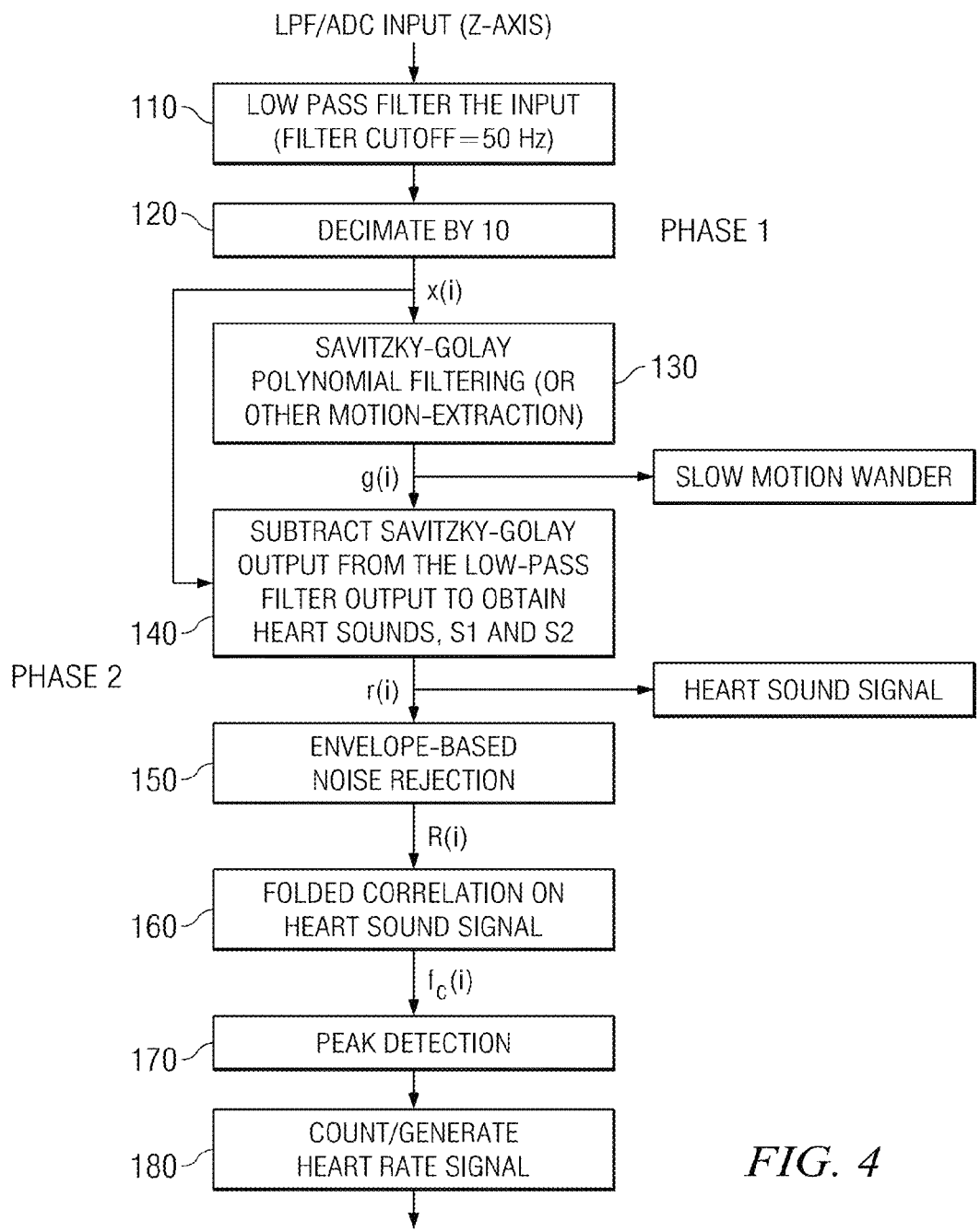
FIG. 4 is a flow diagram of the inventive structure and process for separating a heart signal from body motion and noise using a single accelerometer chest sensor and remarkable smoothing filter and residue circuit, envelope-based noise rejection, folded correlation and other steps.

Some of the embodiments remarkably introduce a Data Acquisition/Signal Processing unit 20 with a special smoothing filter 130 in FIGS. 3-4 that tracks slow varying body motion signal wander or variation and then removes the wander from the sensor-based signal to give a clean (motion-removed) biomedical signal of interest on a Display unit 30. The smoothing filter 130 involves a polynomial filter or comparably effective smoothing filter used directly or in a composite signal processing path. Some embodiments use a subtraction step 140 as in FIG. 4 to remove non-stationary motion artifacts reliably and robustly. Removing such artifacts makes the system more fully immune to sensor placement and contact variations on the chest that might arise when using sensor 10. This provides a simple, yet effective way to reduce the impact of motion artifacts and allow the reliable detection of primary heart sounds and subsequent derivation of heart rate even when a person is walking while being monitored. In this way, motion signal removal or separation, and heart-sound signal detection and heart-rate detection are facilitated. No secondary reference or noise source is needed, thus reducing complexity of system design. Embodiments of structure and method thus extract primary heart sound signals from chest-worn sensor (e.g., accelerometer) data in the presence of motion artifacts.

Results from six subjects showed a primary heart signal detection rate of 99.36% with a false positive rate of 1.3% as described elsewhere herein (TABLE 2). Such type of embodiment appears to outperform noise removal techniques such as wavelet de-noising and adaptive filtering. (In certain motion conditions, or in combination, alternative approaches like Wavelet Decomposition, Adaptive Filtering, Blind Source Separation may in some embodiments also be used instead of, separately from, parallel to, or in combination with, the polynomial filtering.)

Advantages include: 1) uses as few as a single sensor or signal capture component, 2) eliminates use of a secondary reference sensor, 3) allows unobtrusive and non-invasive monitoring of vital biomedical signals in ambulatory settings for continuous monitoring applications, 4) separates heart signals independent of non-stationary bodily motion wander.

For biomedical instrumentation and signal processing for heart sounds specifically, problematic motion artifacts are thus removed from biomedical signals—such as from chest accelerometer signals and/or from electrocardiogram (ECG) signals—for use in ambulatory health monitoring settings. The embodiments can also be extended by use of a spectrum analyzer (Fourier analysis) to extract frequency separable components of interest too.

Ambulatory monitoring of cardiac activity can find widespread applications in home health monitoring of patients with a history of cardiovascular conditions, monitoring older adults, ICU and hospital monitoring, monitoring vital signs in mobile ambulances, at accident and trauma sites and can be used for fitness monitoring at exercise centers and elsewhere.

Figure 1:
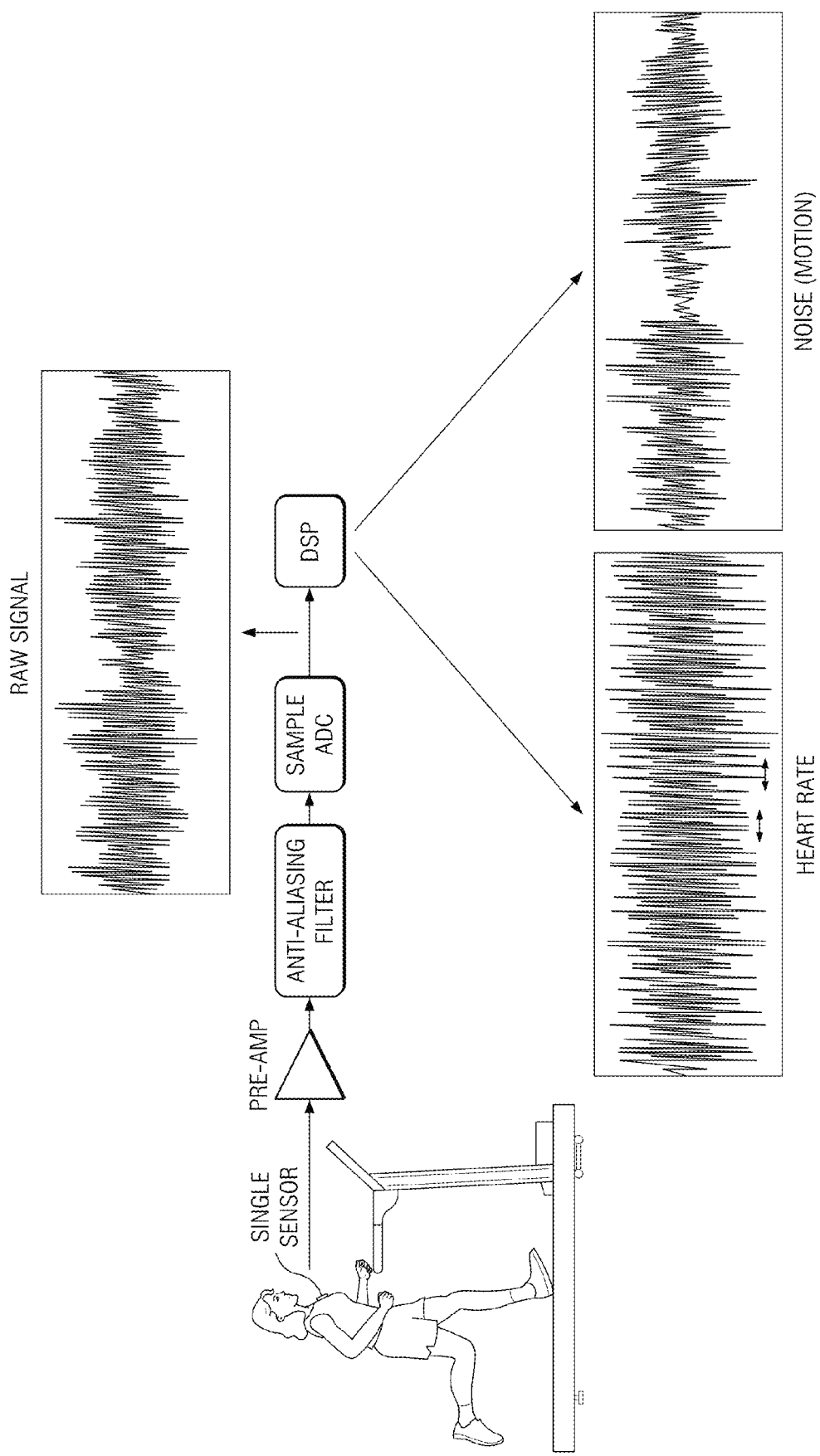
FIG. 1 is a partially-block, partially-pictorial, partially graphical depiction of an inventive structure and process for separating a heart signal from body motion and noise using a single chest sensor.
Figure 2:
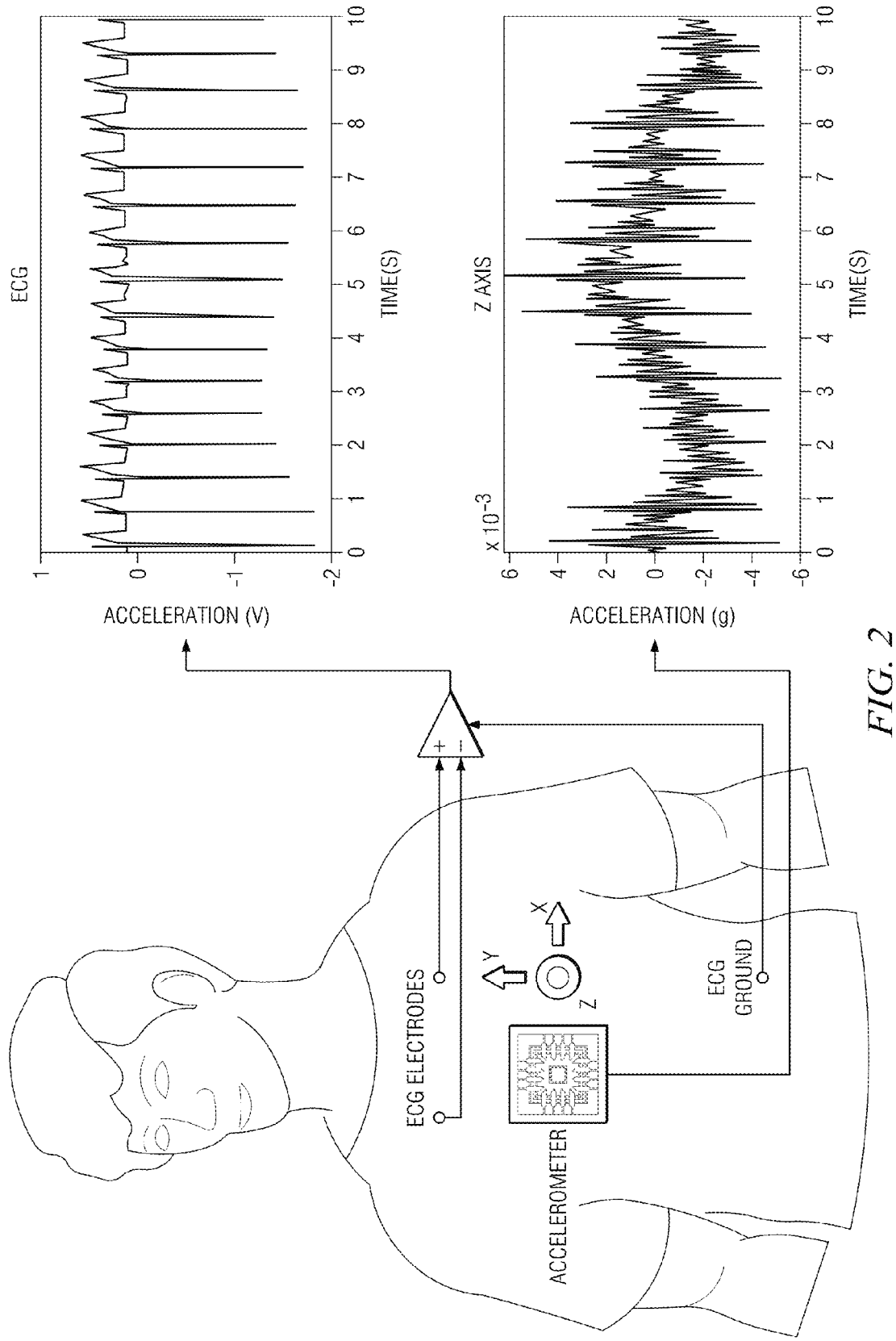
FIG. 2 is a partially-schematic, partially-pictorial, partially graphical depiction of a measurement setup including both an accelerometer sensor on the chest with a composite signal having heart signals and motion and noise, as well as an electrocardiogram ECG circuit with ECG electrodes affixed to the body and showing an operational amplifier and an ECG signal.

In some structure and process embodiments for removal of motion-related artifacts from biomedical signals, beneficial monitoring is provided for, e.g., either or both of two independent signal sources—accelerometer 10 and ECG of FIG. 2. Chest acceleration signals are collected in an ambulatory (walking) setting from real human subjects using a chest-worn accelerometer 10—providing primary heart sounds signified as S1 and S2. Heart sound S1 includes audible sounds concurrent with tricuspid and mitral valve activity and shows on a seismocardiogram as a pulse bundle. Heart sound S2 is mainly associated with pulmonary valve and aortic valve activity. Structures and processes of the embodiments thus remove motion artifacts and facilitate the use of a single, miniature, chest-worn MEMS accelerometer to pick up heart activity and heart rate—derived from heart sounds—from ambulatory subjects as shown in FIGS. 1 and 2. In FIG. 2, electrocardiogram signals are independently collected from the human subjects walking briskly or running on a treadmill—providing signal components such as QRS from the ECG.

Some background heart anatomy terms are as follows. De-oxygenated blood enters right atrium of heart via inferior vena cava and superior vena cava from systemic veins. The right ventricle of heart receives de-oxygenated blood from right atrium and pumps it via the pulmonary artery to the lungs where carbon dioxide is released and oxygen is received into the blood. The blood moves from the lungs via the pulmonary vein to the left atrium of the heart. Valves open and close at the entry to, between, and exit from, the atria and ventricles. The left atrium passes oxygenated blood to the left ventricle, which pumps the oxygenated blood out the large artery called the aorta. The aorta connects by systemic arteries to cerebral, coronary, renal, visceral (splanchnic), and skin vasculatures and to vasculature of skeletal muscles. The names of the valves are: tricuspid valve—right atrium to right ventricle; pulmonary valve—right ventricle to pulmonary artery; mitral valve—left atrium to left ventricle; and aortic valve—left ventricle to aorta.

The primary heart sound components, S1 and S2, are composite signals generated by valve closures. S1 is caused by the closure of the mitral and tricuspid values of the heart, and S2 is caused by the closing of the aortic and pulmonary valves. An analog electrical heart monitoring signal is captured by two or more ECG electrodes, and the signal is a varying voltage representing electrical activity of the heart, i.e., the signal generated in a person's body to cause the heart to contract or relax. The ECG signal has three main components, a P-wave, a QRS complex made up of a Q-wave, an R-wave, and an S-wave, and a T-wave. The pulses include a small positive P pulse, a larger negative-going QRS depolarization pulse near in time to the S1 heart sound, and a large positive-going T pulse near in time to the S2 heart sound. The P-wave represents the depolarization (electrical activation) of the atria of the heart. The QRS complex represents the ventricular activity of the heart. The T-wave represents the re-polarization of the ventricles.

Process and structure embodiments can also be extended to other biomedical signals corrupted by motion wander—e.g., ECG electrocardiogram, PPG—photoplethysmogram (signal from a Pulse Oximeter), EEG—electroencephalogram, EMG—electromyogram, ICG—Impedance Cardiogram signals—or almost any other signal that might be affected by a separable wander. Thus, motion-related artifacts are removed from such other biomedical signals in products that can be produced by a manufacturer in volume.

Remarkably, with some of the embodiments of structure and process, polynomial smoothing and differentiating functions and operations are performed. A secondary reference sensor or signal source is unnecessary. Gross motion is tracked and canceled out from the primary accelerometer-based signal. A polynomial smoothing filter 130 (for example, a Savitzky-Golay filter) is electronically instantiated herein and digitally smoothes a given accelerometer-based data signal stream by approximating it within a specified data window by a polynomial of a specified order that best matches the data in the window in a least-squares sense. Here, the electronic smoothing filter 130 fits the slower variations in body-motion-induced components of the biomedical sensor-based signal and subtracts them as smoothed content from the biomedical sensor-based signal to leave behind what is called a residue signal. The residue signal provides a thus-extracted, faster-varying signal—primarily the heart sounds and other cardiac activity, as well as some residual or remaining noise.

Such polynomial filtering 130 preserves higher order moments around inflection points, or at extrema like peaks and troughs, that a digital moving average or low-pass filter does not. In other words, the polynomial filtering better preserves features—like local maxima and minima—through a least-squares polynomial fit around each point. Also, unlike a moving average, in estimating the value of the fit at a certain point, it does not factor in the values on the polynomial fit around it, therefore not introducing a bias at such features while reducing the noise.

In FIG. 1, a system embodiment has hardware that provides a measurement set-up and monitoring embodiment. A miniature (weight—0.08 gram, size—5×5×1.6 mm) triple axis, low-power, analog output MEMS accelerometer (LIS3L02AL, STMicroelectronics, Geneva, Switzerland) is taped onto the chest (e.g., a few inches to the left of the sternum along the third or fourth rib). (Taping the accelerometer sensor or using a chest band presses the accelerometer sensor to or against a bare or shaved portion of the chest and efficiently couples chest acceleration to the sensor.) An acceleration signal corresponding to the cardiac activity is captured along the Z-axis—the dorso-ventral direction orthogonal to the plane of the chest. The chest acceleration signal is AC coupled with a 3 Hz cut-off and amplified with a gain of 100 and low pass filtered—for anti-aliasing—through a three-stage, 5-pole Sallen-and-Key Butterworth filter with a 1 kHz corner frequency. A commercial quad operational amplifier (op amp) package (LT1014CN, Linear Technology, Milpitas, Calif.) is used for the analog front-end. The accelerometer signal is then sampled at 10,000 Samples/sec using a data acquisition card (National Instruments, Austin, Tex.) and captured and stored on a computer using MATLAB software (Version 2007b, The Mathworks, Natick, Mass.).

The AC coupling with approximately 3 Hz cutoff, which is a non-critical rolloff frequency, is provided, for example, by a series coupling capacitor C coupled to an input resistance established for the amplifier.

In FIG. 2, a reference ECG (lead II) is acquired simultaneously in a three electrode (single lead) electrocardiogram ECG amplifier configuration as a standard of reference in order to compare with the accelerometer-derived cardiac signal for the evaluation of the performances of the heart rate extraction from the accelerometer signal.

In FIGS. 3 and 4, for detection of primary heart sounds and cardiac activity, the acceleration signal is digitally low pass filtered in a step 110 at 50 Hz—using a 3326 tap digital FIR filter with a steep 80 dB roll-off over 20 Hz—and decimated in a step 120 by a factor of 10. (Rolloff frequency less than 60 Hertz attenuates 60 cycle USA power line interference with biomedical signals of interest, and rolloff may be made less than 50 Hertz for applicable countries using 50 Hertz. While the rolloff frequency could be made higher, this FIR filter also desirably attenuates white noise above the frequency range of the signals being monitored.) Also in a Phase 1, a high order Savitzky-Golay polynomial smoothing filter 130, using 28th order and 401 point frame, is used to capture the relatively slow-varying motion wander and leave out the more rapidly varying heart sound signal components. (Matlab syntax for such filter is g=sgolayfilt (X,28,401) where g is the filter output and X is a latest input column vector of 401 sample values of windowed data.) In a Phase 2, the smoothing filter 130 output is subtracted in a step 140 from the decimated LPF output to obtain heart sounds S1 and S2. A folded correlation process in a step 160 then enhances and strengthens the polynomial filtered S1/S2 peaks in the motion-removed acceleration signal. Such folded correlation process 160 is described in further detail elsewhere herein and with background in U.S. Patent Application Publication "Heart Rate Detection In High Noise Conditions" 20100094150, dated Apr. 15, 2010 (TI-66732), which is incorporated herein by reference. Then the location of the peaks is threshold-detected in a step 170 using an electronic amplitude-based peak picking process, and the selected peaks are counted in a step 180 to calculate heart rate HR.

Figure 5:
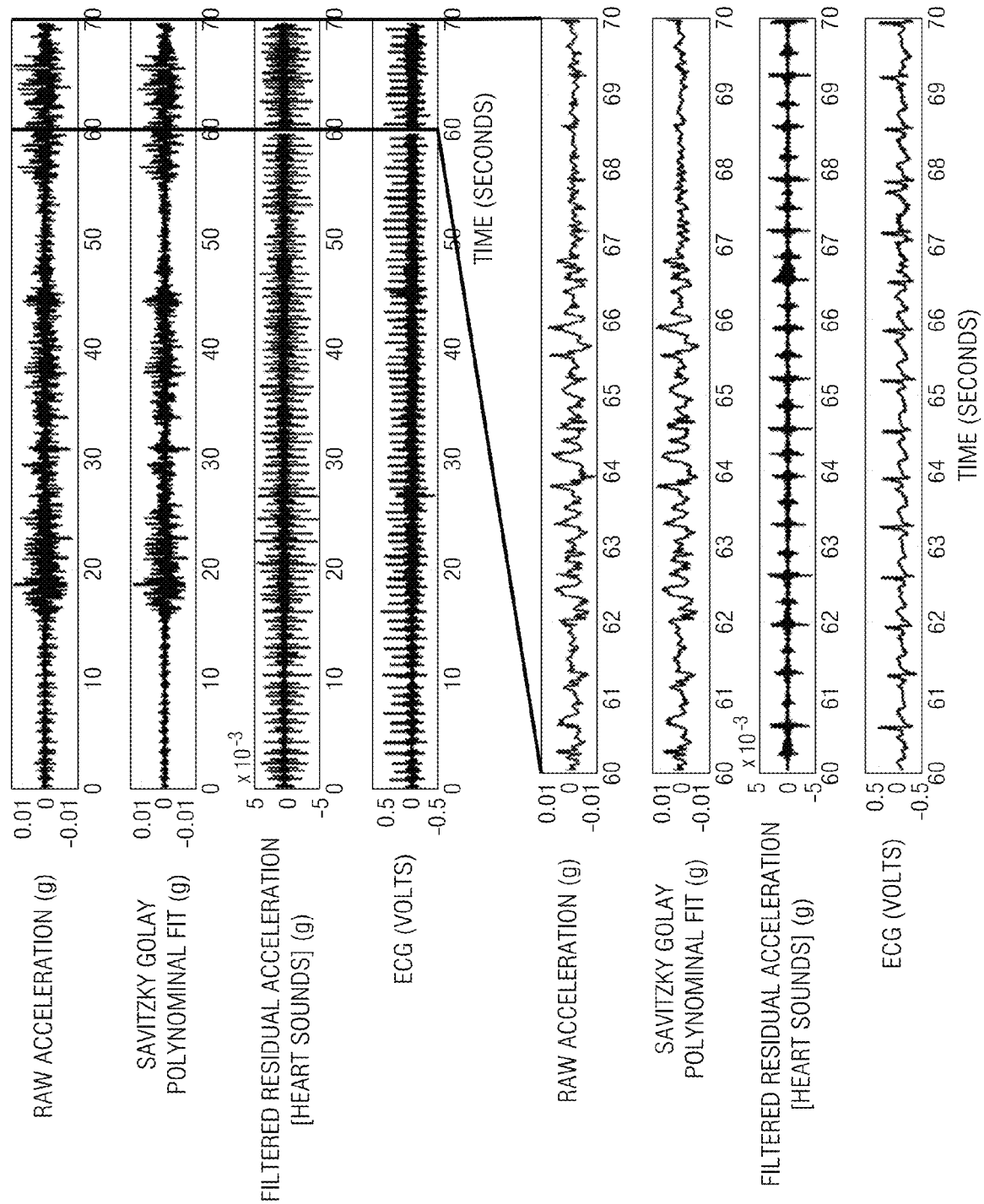
FIG. 5 is a set of four concurrent waveform traces of voltage versus time in various parts of the inventive structure and process of FIGS. 2, 3 and 4 with a subject walking around a room. A time interval portion of the traces is magnified and shown as four time-magnified waveforms maintaining the same voltage scale for each. Some of the traces are accelerometer-based and one is ECG-based.

In FIG. 5, a chest-acceleration signal is derived from the accelerometer sensor while a subject is walking around a room and low pass filtered at 50 Hz (step 110) as shown in a first waveform. LPFing (low pass filtering) sub-50 Hz is used in some of the examples because most of the desired signal power lies in that range and in general LPFing with some rolloff frequency below about one hundred Hertz in many of the embodiments avoids making the bandwidth so wide as to encompass and integrate a substantial or undue amount of sensor noise (thermal, white spectrum). In case LPF with a rolloff frequency above power-line frequency is used, then some embodiments also include notch-filtering for power-line frequency rejection. In FIG. 5, a second waveform is an electronically-derived polynomial smoothing filter 130 output corresponding primarily to the body motion. A third waveform concurrently shows the residue signal after subtraction 140 in FIG. 4 and isolates the primary heart sounds. A simultaneous ECG timing signal is shown as a fourth concurrent waveform for reference.

Figure 6:
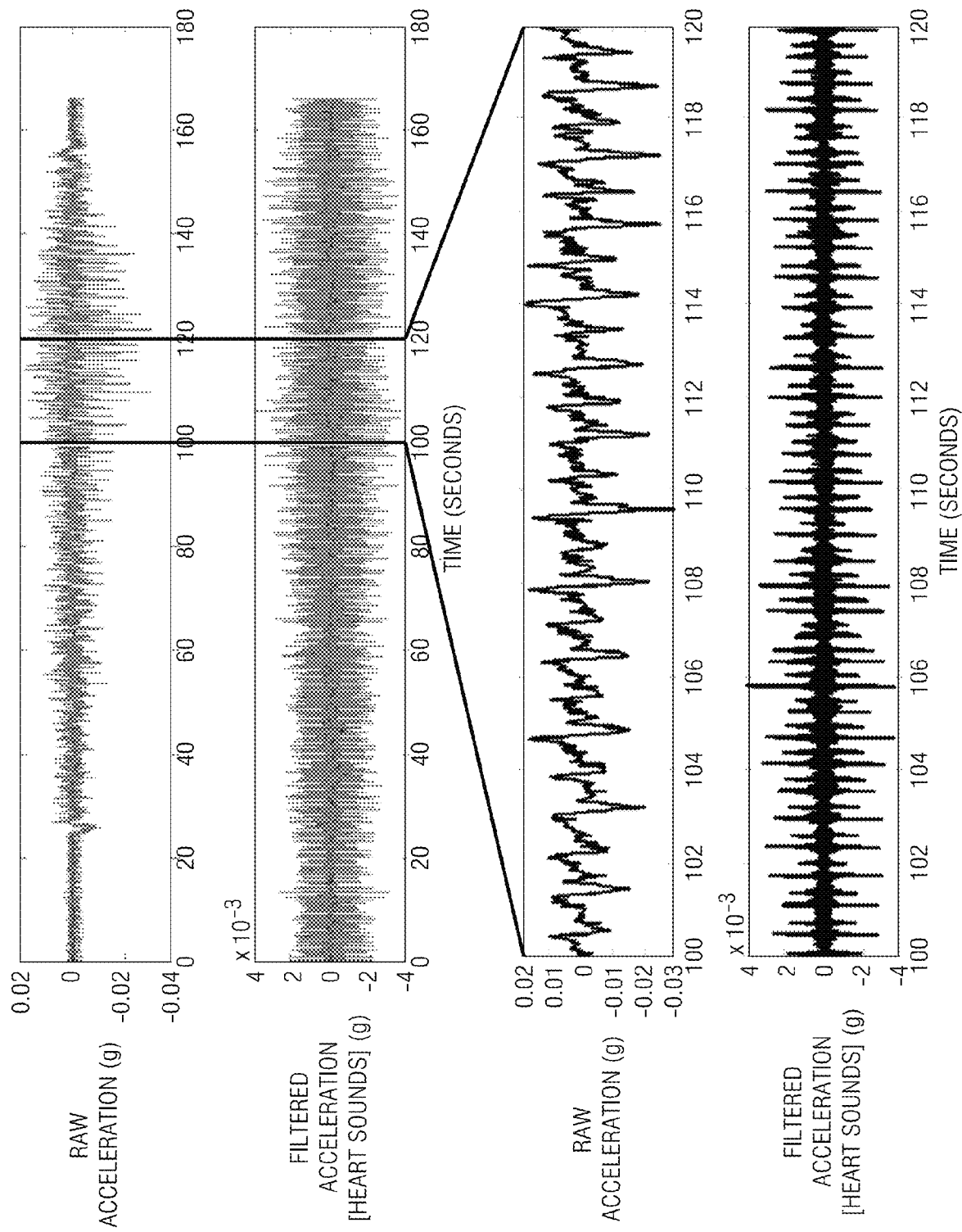
FIG. 6 is a pair of concurrent accelerometer-based waveform traces of voltage versus time in parts of the inventive structure and process of FIGS. 2, 3 and 4 with a subject walking on a treadmill. A time interval portion of the traces is magnified and shown as time-magnified waveforms maintaining about the same voltage scale for each.

In FIG. 6, the same embodiment monitors a chest-acceleration signal from the accelerometer Z-axis sensor while the subject walks on a treadmill. A brief rest recording is followed by motion. Compared to FIG. 5, the plot of FIG. 6 analogously shows an unfiltered (raw) acceleration signal and the residue from step 140 after the polynomial smoothing of step 130. Note the magnified scale in some parts of FIG. 6, and that FIG. 6 has a different scale than in FIG. 5.

Figure 7A:
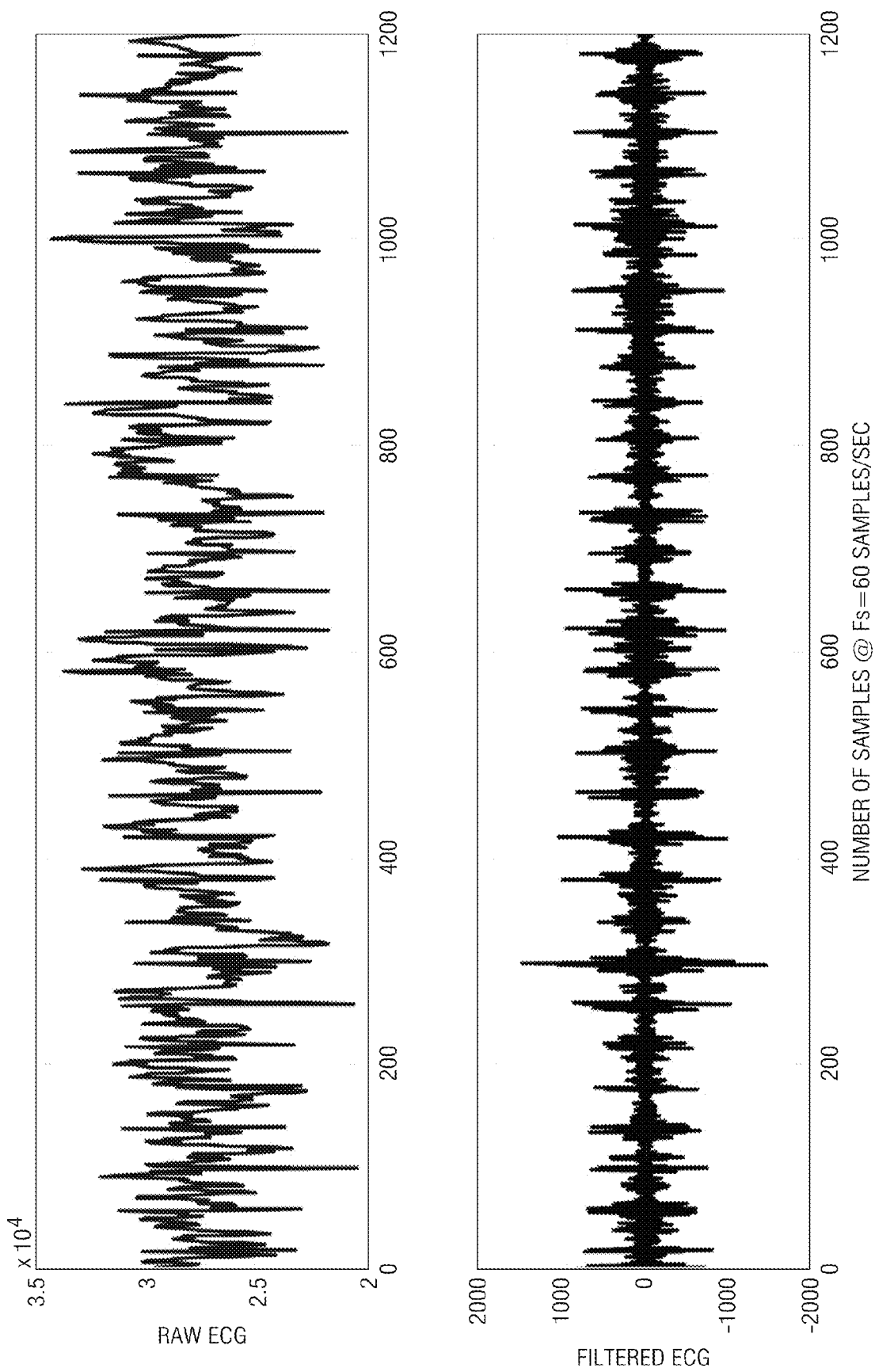
FIGS. 7A, 7B, and 7C are each a pair of concurrent noisy handgrip ECG-based waveform traces of voltage versus time in parts of the inventive structure and process of FIGS. 2 and 4 with a subject walking on a treadmill. The ECG-based waveforms are one unfiltered, and one inventively filtered to recover a heart sounds signal.
Figure 7B:
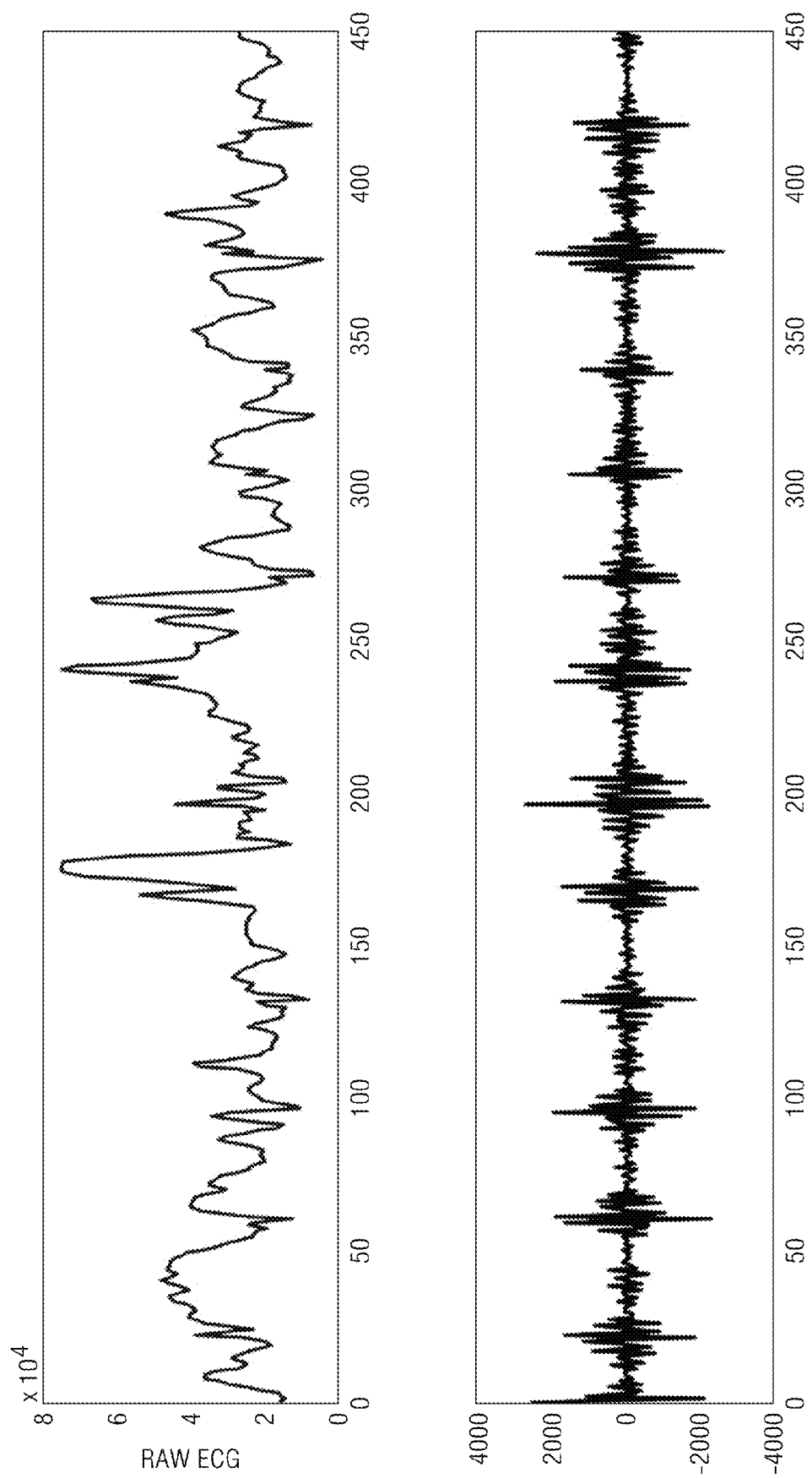
Figure 7C:
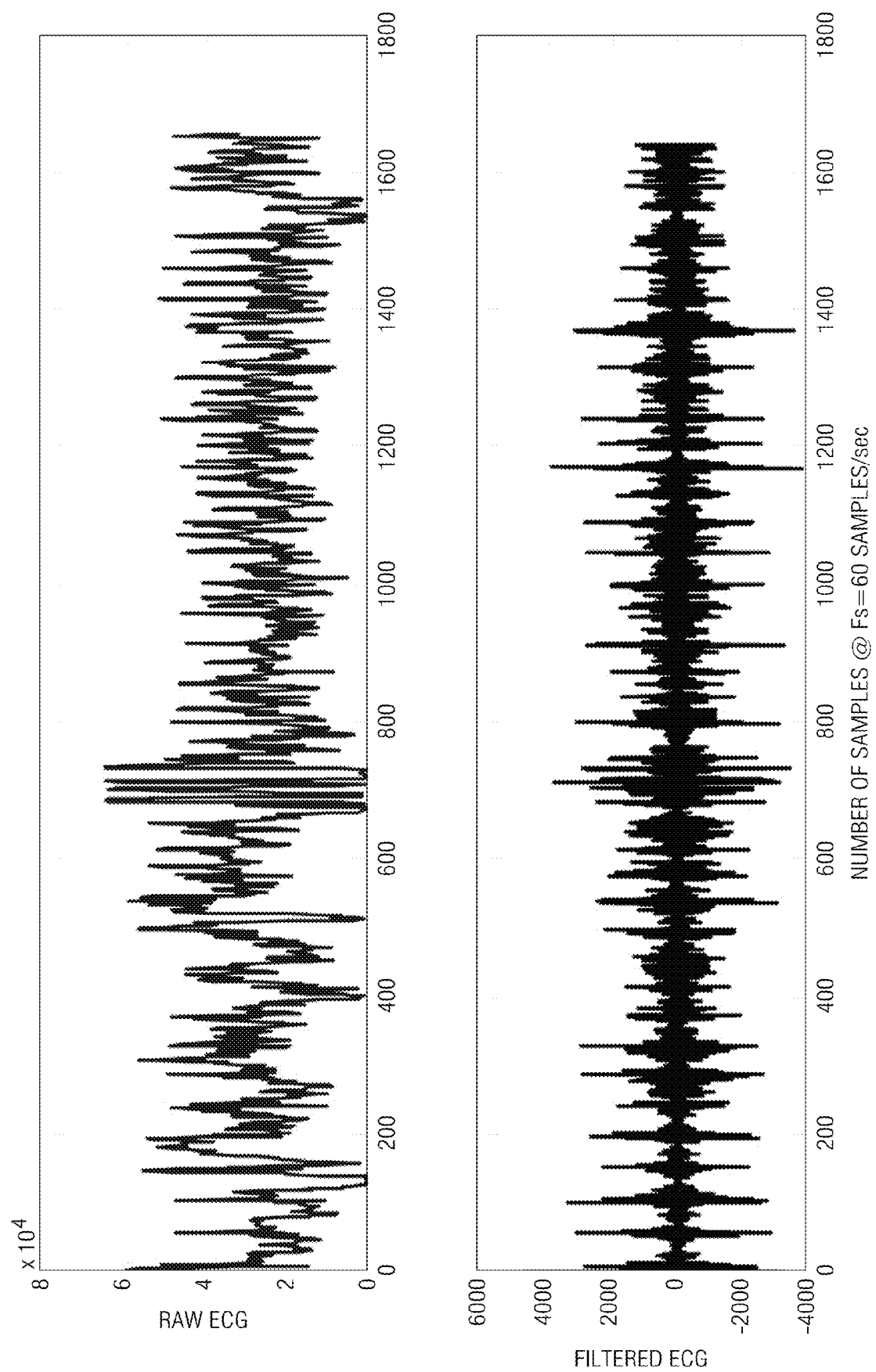

FIGS. 7A-7C show signal plots for an ECG filtering embodiment 2. The plots have different time scales and walking conditions. Raw ECG signal from the ECG electrodes in FIG. 2 and a concurrent filtered ECG signal waveform, by applying steps 110-140 separately to the ECG signal, are depicted for a subject walking on a treadmill.

In another embodiment, satisfactory S1-S2 heart signals were extracted from raw motion-affected accelerometer Z-axis data by LPF (low pass filtering) with corner at 100 Hz and then Savitzky-Golay filtering at $20^{th}$ order, followed by subtraction of the S-G signal from the LPF signal, and followed further by signal enhancement. It appears that polynomial filtering of motion-affected LPF accelerometer signals, using polynomial filtering on the order in a range of approximately $20^{th}$ order or higher order to at least over $30^{th}$ order, is satisfactory for obtaining heart signals as a residue by subtraction of the polynomial filtering output from the LPF signals. Using polynomial fits at such orders successfully captures both coarser and finer motion effects. The smoothing filter in some embodiments can be lower order as well, and may obtain good results even with a $1^{st}$-order polynomial in case of some window sizes and applications. Also, lower order polynomial filtering is contemplated and found useful as discussed later hereinbelow. Using a number of points at least approximately half again (1.5 or more times) an order of the polynomial and even substantially higher than that, in some of the embodiments, is believed to help to reduce noise.

Figure 8:
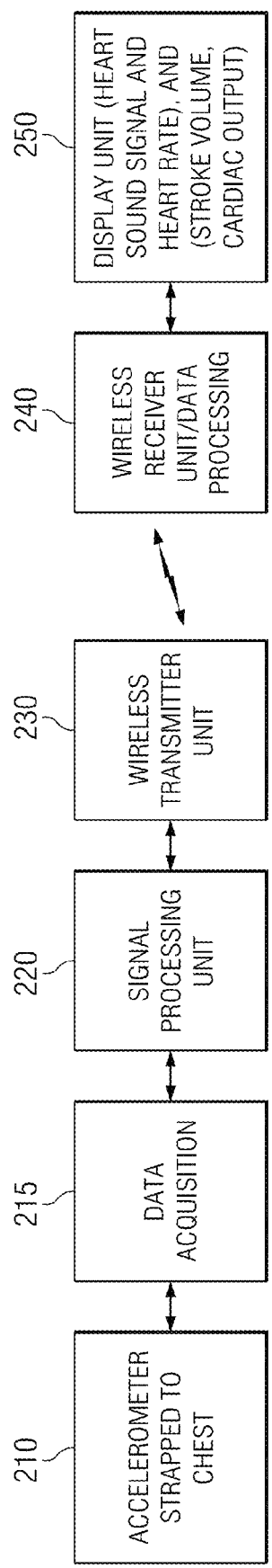
FIG. 8 is a block diagram of another inventive structure and process for obtaining cardiac information using an accelerometer chest sensor, such as heart rate and information related to beat-to-beat changes in stroke volume and cardiac output.

In FIG. 8, a wireless embodiment has the accelerometer sensor 210 in a chest-worn miniature unit including Bluetooth or pico-network wireless or an RF transponder. The miniature unit 210 wirelessly communicates with a Data acquisition/signal processing unit 215, 220 of FIGS. 8 and 4 such as provided on a belt clip, in a cell phone or in a gateway elsewhere in a residence (see FIG. 39). In FIG. 8, the signal processing unit 220 is coupled to a wireless modem 230 or transmitter (or to a wireline modem) for transmission to a remote location such as a medical clinic. The medical clinic has a receiver or transceiver such as in a cell phone or wireless or wireline modem 240, and further has a data storage and display unit 250. The medical clinic can interrogate the residential data acquisition/signal processing unit 220 by transceiver 240 via residence-based modem 230 and re-configure the residential unit 215, 220 for various performances and for more or less information and more or less frequent communications.

In FIGS. 3 and 8, any two or more, or all, of the described components can combined in a single digital system. The monitoring signal capture component 210 is configured to capture a heart monitoring signal from a person and provide it to an analog signal conditioning and sampling section 215 (A-to-D) that feeds digital data to the signal processing component 220. In some forms, the A-to-D happens physically within the accelerometer chip and the signal flow remains electronically arranged as shown. Either or both of components 210 and 215, 220 may provide amplification and noise reduction of the analog and/or digital signal in the process. In various embodiments, the heart monitoring signal may be provided to the processing component 220 in real-time, and/or may be provided periodically as the signal is being captured, and/or may be recorded and provided to the processing component at a later time.

The digital heart monitoring signal may be provided to the data acquisition 215 and signal processing unit 220 by wired or wireless forms of communication, e.g., wired using a USB port, electrode wires, logic circuitry, etc. or wirelessly such as by a Bluetooth connection, Zigbee, or otherwise. In FIG. 8 a communications network for remote transmission can be wide area network (WAN) such as the Internet, a wireless network, a local area network (LAN), or a combination of networks. Similarly, the processing component 220 may be connected to an output component 250 by any of the foregoing connections and networks. Any suitable display device and/or recording apparatus 250 is used such as, for example, a computer monitor, a display of a handheld computing device, a display in a personal heart rate monitoring device, a display in a piece of exercise equipment, etc. The system hardware of FIG. 39 may be applied with one program at both the premises at which the accelerometer is used and a replica of that system hardware applied with that program and/or an additional program at the remote premises such as a medical clinic.

The system components including signal processing component 220 may also be implemented by or as part of any suitable digital system (e.g., a general purpose processor, a digital processor, a personal heart rate monitoring system, a heart rate monitoring system in a piece of exercise equipment, a personal computer, a laptop computer, a server, a mainframe, a personal digital assistant, a television, a cellular telephone, an iPod, an MP3 player, etc.) configured to receive the digital heart monitoring signal from the monitoring signal capture component 210. The processing component 220 is configured to process the digital heart monitoring samples in the digital heart monitoring signal in accordance with embodiments of methods described herein. In one or more embodiments of the invention, the processing component 220 includes functionality, e.g., a computer readable medium such as memory, a flash memory, an optical storage device, a disk drive, flash drive, etc., to store executable instructions implementing an embodiment of a method for processing heart monitoring samples as described herein and to execute those instructions.

Embodiments like those of FIGS. 8 and 4 and other Figures herein have potentially wide-ranging applications from commercial products that already have in-built accelerometers (e.g., mobile phones, personal entertainment devices, content players, computer game controllers etc.) and those that do not (clothing, accessories etc.) to fitness products (heart straps, belts, wearable adhesive bandages or sensor tapes, clips, straps, bands or carriers for temporary affixing to one's chest, arm or elsewhere on the body, or implantable sensor devices), Embodiments are suitably made as a part or whole of ambulatory monitoring products for ambulances, at trauma sites (e.g., for accident or burn victims), for home-monitoring of older adults and all populations to which the advantages of the embodiments commend themselves.

The accelerometer 210 signals from all three axes are suitably also processed to electronically double-integrate the acceleration to determine the location of the person wearing it. Since the person is likely to have been in bed overnight, the processing determines the location of the person during the day by double-integrating the acceleration starting from initial conditions of position initially at the bed location, and zero initial vector velocity. This information can be helpful as a cue to the person who is visually impaired, to care-giver, and to a family member. The accelerometer processing can indicate that the person is in a given room of the residence, as an assist for one who is visually impaired, or can indicate that the person is leaving or has left the residence to inform a care-giver or family member. In this way, the accelerometer and associated processor provide numerous services for all concerned, in various ways as taught herein.

For background on accelerometer calibration and double-integration see U.S. patent application "Parameter Estimation for Accelerometers, Processes, Circuits, Devices and Systems" Ser. No. 12/398,775 (TI-65353) filed Mar. 5, 2009, which is incorporated herein by reference in its entirety.

Due to its low-cost and ease of use, products using the embodiments have potential for commercial success not only in urban and developed areas but also widely in the developing world as well as in rural parts of the developed world or in any place where low-cost, remote health monitoring facilities may be rare, if available at all.

The smoothing filter 130 of FIG. 4 is configured based on a specified order M and frame size (number of sample points N). For instance, a Savitzky-Golay polynomial smoothing filter is used in some embodiments to best approximate the acceleration signal in the least-squares sense to capture the motion-dependent baseline-wander. In some embodiments, the smoothing filter is implemented in flash memory of a local processor of FIG. 39 such as a belt-worn unit or provided in a home network gateway or clinic office network gateway, or cell phone or otherwise.

The matter of selecting and or finding feasible and optimum values for order M and window length ($N_W$ in points, $t_W$ in time) for the polynomial smoothing filtering is discussed next. In general for a fixed window length, $N_W$, a higher order polynomial will fit the high frequency components of the streaming data better. For a given order M, a shorter window of time will allow fitting the high frequency component better.

In FIG. 4, the working hypothesis is that the accelerometer signal has a low-frequency (motion) component and a high frequency (heart signal) component. The polynomial filter is used to fit to the motion component.

A way to approach the optimization problem estimates the inherent order of the low-frequency component and picks the smallest window that satisfies the condition that $N_W > M+1$ and $N_W$ is odd (i.e., $N_W = 2N+1$). The smaller window size $N_W$ is, the smaller is the number of taps of the multiply-accumulate filter process implementing the smoothing filtering. For an accelerometer signal in some applications, order M=1 and window size $N_W = 3$ (sampling frequency is 1000 Hz). In some examples herein, higher orders M and window widths $N_W$ are shown.

In FIG. 4, motion, heart sounds and heart rate are electronically separated and ascertained from accelerometer 210 data using the following steps:

a) Low-pass filtering 110 and decimating 120 the accelerometer data
b) Savitzky-Golay filtering 130 to fit the relatively lower frequency motion data
c) Subtracting 140 the output of the Savitzky-Golay filter from the low-pass filtered accelerometer data (from step a) to obtain the heart sounds
d) Performing 160 folded correlation to enhance the primary heart sounds (S1 and S2) peak locations
e) Peak picking 170 to count the number of S1 peaks in a predetermined or configured segment (time interval) and counting 180 the heart rate HR in beats per minute BPM.

Note that the term 'decimation' refers to any process of regularly removing samples from a sample stream, or passing one sample in every $n_D$ samples as decimation parameter, and can but does not necessarily refer to removing all but 1 sample in ten. Thus, if a sample/ADC delivers $f_S$ samples per second, then a decimation process delivers a decimation frequency substantially $f_S/n_D$ samples per second. If a window period is $t_W$ seconds, then the number of points $N_W = 2N+1$ in the window is $N_W = 1 + f_S \, t_W/n_D$. The window period $t_W$ may be selected by considering the time period over which the particular features and behavior of interest are to be obtained by the filtering from the signal. The sampling frequency $f_S$ may be selected with cost, physical size and complexity of anti-aliasing in mind (low pass filter AAF at $0.5 f_S$ or less situated ahead of sampling $f_S$). The sampling frequency $f_S$ may be set substantially greater than the Nyquist frequency for sampling the AAF output. The decimation parameter $n_D$ is then selected, firstly, to yield a decimation frequency $f_S/n_D$ that is sufficiently high relative to the e.g., 50 Hz low pass filter LPF following the sampling/ADC circuit to provide effective operation of that LPF. Secondly, the decimation parameter $n_D$ is also selected to yield a number $N_W$ of window points that is sufficiently high relative to the selected order M of the filter to keep filter noise low while having the $N_W$ window points being sufficiently low in number as to introduce only so many filter computations as needed to achieve satisfactory filtering of the signal stream in the window. The filter computations are related to the product of the number $N_W$ of points per window multiplied by a rate number $r_W$ of windows processed per second. If $r_W = N_W/t_W$, the computations are proportional to $N_W^2/t_W$, which may motivate fewer window points and longer window times in some energy-saving and lower cost processor applications. Remarkably, the examples herein satisfy these considerations for some applications and other examples may readily be devised for other particular applications as well.

Mathematically expressed processes are described in further detail below for preparing various electronic embodiments with smoothing filters for various ways of motion extraction in step 130 and any other purpose to which their advantages commend their use. They are appropriately partitioned into offline and real-time online electronic processes in such embodiments.

The notation $\|(x-Ab)\|$ in Equation (1) signifies the sum of squared differences between the [(2N+1)×1] respective data stream vector sample points or stream components and the (2N+1) respective estimates of those stream components provided by multiplying a [(2N+1)×M] transform matrix A times a [M×1] vector of transform coefficients $b_j$. The number of transform coefficients $b_j$ is M, and they form a [M×1] vector b. A gradient $\nabla$ is the [M×1] vector of first partial derivatives with respect to the transform coefficients $b_j$. The number M of coefficients $b_j$ is called the order, and if the number of transform coefficients $b_j$ is M, then the order of the process is M. The [M×M] matrix of second partial derivatives with respect to the transform coefficients $b_j$ is signified by $\nabla\nabla$. The filter procedure involves, and in effect forms, a coefficients change coefficient vector $\Delta b$ for updating an initial transform coefficient estimate $b=0$ (i.e., all coefficients initialized to zero). This procedure pre-multiplies the matrix of second partial derivatives times the negative of the gradient to obtain that transform coefficients change vector $\Delta b$.

$$\Delta b = -(\nabla\nabla\|(X-Ab)\|)^{-1} \nabla\|(X-Ab)\| \qquad (1)$$

Since the Equation (1) involves a quadratic expression and starts from b=0, the process directly finds the values of the transform coefficients $b = \Delta b$ in one pass without iterating additionally. Equation (2) represents the result of performing the calculus operations represented by Equation (1). (Some embodiments transmit the coefficients b from Equation (2) to a remote site for record storage and further analysis, since they effectively compress much of the information in the data window. If coefficients are to be transmitted, the [Mx(2N+1)] matrix $(A^T A)^{-1} A^T$ is pre-computed and then multiplied by each data window locally on the fly. Other embodiments omit such compression and/or transmission, or only do it locally on remote command, and thereby save some power and processing complexity.)

$$b = (A^T A)^{-1} A^T X \qquad (2)$$

This process generally finds transform coefficients $b_j$ provided the inverse $(ATA)^{-1}$ exists. That inverse exists when the rows of the matrix A are linearly independent (full rank) and enough data points $N_W = (2N+1)$ are provided so that the corresponding number of columns of the matrix is sufficient for an inverse to be delivered.

In the special case of a polynomial transform process, a matrix of indices is raised to powers, wherein the $j^{th}$ column element $A_{nj}$ in the nth row of transform matrix A is raised to a power: $n^j$. In other words, for the 2N+1 different values of n from −N to +N in the window of a data stream X(i+n), the transform finds a set of coefficients $b_j$ for a well-fitting power series to approximate all the values. Such a power series in general is represented by Equation (3):

$$X(i+n) = b_0 + b_1 n + b_2 n^2 + b_3 n^3 + b_4 n^4 + \ldots b_M n^M \qquad (3)$$

Savitzky-Golay filtering outputs as the filter output g(i) for the window indexed i the value of $b_0$ estimated by Equation (2) for each data window, and successively window-by-window for successive indices g(i).

Rows of matrix A are orthogonal when the inner product is zero for any pair of different ones of them. These rows are illustrated in TABLE 1. The rows of values $A_{nj}$ in matrix row n are non-orthogonal for the example of a polynomial transform. ("^" signifies raising to a power.)

TABLE 1

ARRANGEMENT OF MATRIX $A^T$

| | Power m (Order M) | | | | |
|---|---|---|---|---|---|
| Points | 0 | 1 | 2 | 3 | ... M |
| n = −N: | [1 | (−N) | (−N)^2 | (−N)^3 | ... (−N)^M]. |
| ... | | | | | |
| n = −4: | [1 | −4 | (−4)^2 | (−4)^3 | ... (−4)^M] |
| n = −3: | [1 | −3 | (−3)^2 | (−3)^3 | ... (−3)^M] |
| n = −2: | [1 | −2 | (−2)^2 | (−2)^3 | ... (−2)^M] |
| n = −1: | [1 | −1 | 1 | −1 | ... (−1)^M] |
| n = 0: | [1 | 0 | 0 | 0 | ... 0^M] |
| n = 1: | [1 | 1 | 1 | 1 | ... 1^M] |
| n = 2: | [1 | 2 | 2^2 | 2^3 | ... 2^M] |
| n = 3: | [1 | 3 | 3^2 | 3^3 | ... 3^M] |
| n = 4: | [1 | 4 | 4^2 | 4^3 | ... 4^M] |
| ... | | | | | |
| n = +N: | [1 | N | N^2 | N^3 | ... N^M]. |

Next, the process finds an estimated data stream X'=Ab.

$$X'=A(A^TA)^{-1}A^TX \quad (4)$$

An electronic process is set up in a processing circuit as represented by Equation (2) and electronically executed by the processing circuit. For Savitzky-Golay filtering, the process is optimized to only find g(i) as the estimated value of $b_0$ and also to perform as much off-line pre-computation as possible. Accordingly, Equation (4) is revised as in Equation (5) to use only the n=0 row [1×M] of the first pre-multiplying matrix A instead of the whole matrix A in Equation (4), $$g(i)=[1\ 0\ 0\ \ldots\ 0](A^TA)^{-1}A^TX(i) \quad (5)$$

Sometimes a mathematical presentation of Savitzky-Golay filtering regards the window as multiply-added by a set of (2N+1) filter coefficients c(n). Here, a [1×(2N+1)] filter coefficient vector C is introduced so that $$g(i) = CX(i) = \sum_{n=-N}^{+N} c(n)x(i+n) \quad (6)$$

where $$C=[1\ 0\ 0\ \ldots\ 0](A^TA)^{-1}A^T \quad (7)$$

In Equation (8), an alternative notation CI equivalent to Equation (6) post-multiplies Equation (7) by a [(2N+1)×(2N+1)] identity matrix I and designates each of the columns of that identity matrix I as [(2N+1)×1] unit vectors $\epsilon_n$. The phrase 'unit vector' for $\epsilon_n$ means a [(2N+1)×1] vector of all zeroes except for a one (1) at the nth row position. Furthermore, only the matrix inversion computations to form the first row of inverse matrix $(A^TA)^{-1}$ are relevant and are performed, considering the pre-multiplication by [1×M] row n=0 vector [1 0 0 . . . 0]. Thus, the filter coefficients are also equivalently expressed in the notation of Equation (8), which is equivalent to Equation (7).

$$c(n)=\{(A^TA)^{-1}(A^T\epsilon_n)\}_0 \quad (8)$$

The Savitzky-Golay filter does a local polynomial fit in a least square sense. For a given input variable data window x(i+n) and window of length 2N+1 and chosen polynomial degree M, the filter output is given by g(i). Filter coefficients c(n)—2N+1 of them—are computed, e.g. off-line, by electronic operations represented by Equation (7) or (8) and loaded into flash memory of a small signal processing unit either worn on the person or provided nearby and coupled wirelessly to the accelerometer sensor 210 according to the blocks shown in the FIGS. 1-5. The signal processing unit suitably has a digital signal processor circuit such as processor 220 that electronically performs multiply-accumulates (MACs) represented by Equation (6) according to a stored program accessing the filter coefficients c(n).

Some other embodiments use windows that are not centered around the value at index n used as the output (e.g., n=0). It should also be apparent from the above process description that a variety of choices of matrices A are possible and may be used instead of the particular polynomial transform matrix shown in TABLE 1. The skilled worker chooses the desired transform, the window (frame) size (e.g., 2N+1) and the order M. Also, note that g(i) output of a first filter procedure produces a data stream that itself can be windowed as represented by column vector $g_1(i_2)$ in Equation (9B). Accordingly, some embodiments represented by Equations (9A), (9B) cascade two lower order filters of Equation (4) and use straightforward technique to minimize the electronic processing complexity of the computations in implementation. The transform matrices A1 and A2 can be the same or different, the window sizes $(2N_1+1)$ and $(2N_2+1)$ can be the same or different, and the orders $M_1$ and $M_2$ can be the same or different, all these choices being independent of each other.

$$g_1(i_1)=[1\ 0\ 0\ \ldots\ 0](A_1^TA_1)^{-1}A_1^TX(i_1) \quad (9A)$$

$$g_2(i_2)=[1\ 0\ 0\ \ldots\ 0](A_2^TA_2)^{-1}A_2^Tg_1(i_2) \quad (9B)$$

Some embodiments may also apply to the SG process a diagonal weighting matrix W which is all zeroes in a [(2N+1)×(2N+1)] matrix except for weights down the main diagonal. The weights can, for instance, be one at the middle of the diagonal and diminish symmetrically in value farther from the middle of the diagonal. The motivation is that it may not be important for all points in the window to be well-approximated according to unweighted least squares, especially in a filter that is providing a determination of one coefficient as output g(i). In that case, Equation (1) is replaced by Equation (10), which represents that the squares are each weighted in the sum of squares ||(X−Ab)||:

$$\nabla b=-(\nabla\nabla\|W(X-Ab)\|)^{-1}\nabla\|W(X-Ab)\| \quad (10)$$

Then the electronic process represented by Equation (5) for the output instead is:

$$g(i)=[1\ 0\ 0\ \ldots\ 0](A^TWA)^{-1}A^TWX(i) \quad (11)$$

The selection of transform type and matrix A is fixed/predefined by configuration or determined semi-static manner in some embodiments. Dynamic configuration or selection of the matrix A or transform type or parameters of a given transform is contemplated in some other embodiments herein that determine which is the best transform type, order, window size, amount of cascading, etc. to use and then dynamically performs processing and remote communication.

Some other embodiments store and average a set of values from the transform output of Equation (4) from different windowed segments of the data stream X. This approach, roughly speaking, performs several filters in parallel and averages them in an offset manner. All the values represent a reconstructed value corresponding to a same instant of time (i+n)=t, and note that this approach not only uses the n=0 row to approximate $b_0$ but also uses the transform approximations to the other coefficients that are available from Equation (3). In other words, the results of approximating the data stream using $2N_1+1$ successive windows are used by selecting only the particular points that represent a given instant of time t. The number of points $2N_1+1$ averaged (say, some number in a range 3 to 11 points) is enough to average out some noise without much extra computer burden $N_1<=N$. Those points are the successive window data X at indices n=t−i such that for succeeding windows i, the approximate data values X' generated by the power series start at high index n=+$N_1$ and proceed down to n=−N1. The electronic processor 220 (and/or 240) executes instructions or otherwise performs the electronic process as represented by Equation (12), where X'(i+n) is from Equation (4). Equation (12) reduces to Equation (6) when $N_1$=0 (i.e., $2N_1+1$=1).

$$g(t) = [1/(2N_1 + 1)] \sum_{n=-N1}^{+N1} X'(i+n) \Big|_{(i+n=t)} \quad (12)$$

In view of the analysis herein, it is emphasized that other types of processes can be alternatively selected according to the teachings herein, whether they are called Savitzky-Golay or not. The skilled worker sets up a test bench with library accelerometer-based waveforms and then makes the transform matrix choices, choice of number of points (2N+1), and choice of order-value M, either manually or by an automated process. The filtering choices are tested either by visual inspection of a display of output from FIG. 1 process or by automated process according to metrics of false negatives and false positives, etc. as described herein. Transform matrix A values, and values of (2N+1) and M, $2N_1+1$, etc. for one or more such filter processes having favorable metrics are then loaded into the monitoring device flash memory or hard drive and executed in real time on processor 220 (or 240).

A transform for an embodiment approximates an actual data stream vector x(i+n) and produces an output signal stream that follows the heart sound peaks well over time in response to a data stream X herein derived from a body-worn accelerometer. Some embodiments have reduced processing complexity by using low enough frame size (2N+1), order M and/or using an efficient transform matrix A to achieve desired performance for the purposes for which the monitoring is intended. The same transform is desirably low-complexity and well-performing over numerous patients, accelerometers and their positioning on the body, and in different environments of use, such as clinic, hospital, home, exercise venue, etc.

Figure 9:
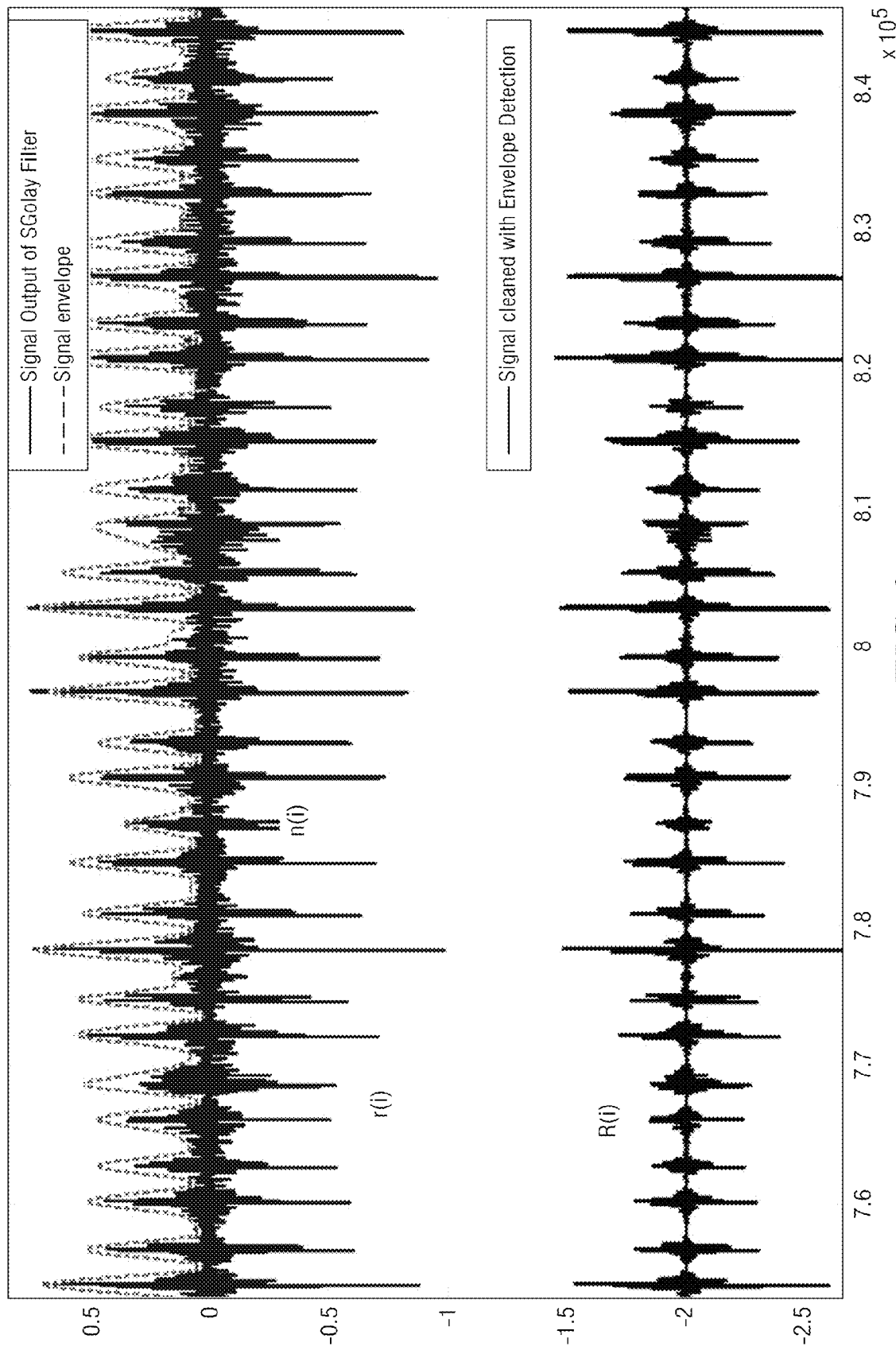
FIG. 9 is a pair of concurrent accelerometer-based waveform traces of voltage versus time in parts of the inventive structure and process of FIGS. 3 and 4 pertaining to envelope-based noise rejection.

In FIG. 4 and turning to a succeeding electronic process portion 150 for envelope-based noise rejection, an amplitude envelope is generated, as shown in FIG. 9. In FIG. 9, the residue signal stream r(i)=x(i)−g(i) of FIG. 4 has some remaining noise from subtracting step 140 that subtracts the smoothing filter output g(i) from the LPF-supplied input x(i). An envelope is fitted to the residue as indicated by the dotted envelope-line in FIG. 9. The amplitude-based processed output R(i) is shown in FIG. 9, as derived from the envelope-fitted residue r(i). The noise n(i) near the horizontal axis is substantially reduced. Operations for this process suitably use an envelope-related variable gain function. Alternatively, the circuit and/or process is arranged to generate zero signal output when the envelope is below a low threshold that still passes the peaks.

Description next turns to the FIG. 4 electronic process portion 160 called folded correlation. For background, see the incorporated patent application publication TI-66732. An input data stream of residue r(i)=x(i)−g(i), or envelope-processed residue R(i) comes to the folded correlation process. Recall that g(i) is the output of the smoothing filter such as represented by Equation (6) or from a buffer memory for it. Processed filtered residue R(i) is windowed by a further data window (also called a frame) of length $2N_2+1$ (with points accessed by an index n=0, 1, 2 ... $N_2$).

The output $f_c(i)$ of the folded correlation is given by Equation (13):

$$f_c(i) = \sum_{n=0}^{N2} R(i - N_2 + n)R(i + N_2 - n) \quad (13)$$

The digital data stream for heart monitoring residue signal samples R(i) from the smoothing filter subtraction is successively processed in overlapping frames indexed i. In general, the value of $2N_2+1$ is selected to be approximately the width $t_W$ of a desired signal event (e.g., an S1, S2, or R-wave). For example, S1 is typically about 100-150 milliseconds long. If the decimated sampling frequency $f_S$ is 1000 Samples/sec, the value of $2N_2+1$ is established, e.g., as an odd number between 101 and 151, and N2 is some number between 50 and 75 inclusive. Thus, $$N2=RND(t_W f_S/2) \quad (14)$$

In some embodiments, the value of N2 is configured in flash memory, and can be selected or altered by a local or remote operator of a FIG. 8 remote digital system portion 240, 250 using the embodiment of structure and process.

In the electronic folded correlation process 160 represented by Equation (13), the heart monitoring residue samples R(i+N2−n) from the later half of each frame are folded around the center heart monitoring sample R(i) in the frame and multiplied by dot product (sum of products in Eq. (13)) with heart monitoring residue samples R(i−N2+n) in the earlier half of each frame. The result of the dot product is a folded correlation output signal stream $f_c(i)$ corresponding to instant i of the input residue signal stream R(i) in the center of the frame.

Figure 10:
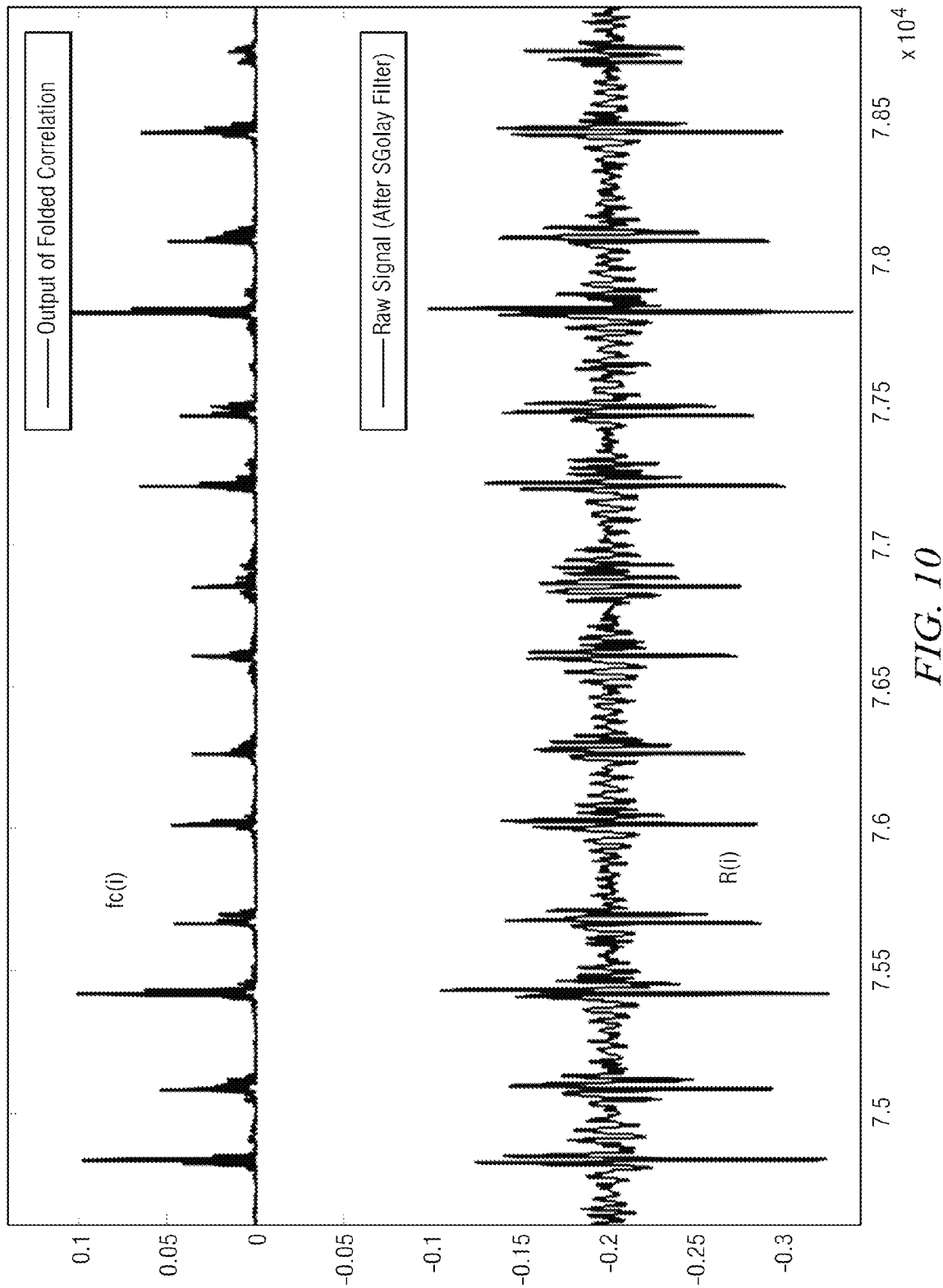
FIG. 10 is a pair of concurrent accelerometer-based waveform traces of voltage versus time in parts of the inventive structure and process of FIGS. 3 and 4 pertaining to folded correlation.

In FIG. 10, the residue signal input R(i) (subtraction of SG fit from LPF input) is shown in a lower waveform and an output $f_c(i)$ of Folded Correlation 160 is shown in an upper waveform. Sharp, distinct, positive peaks in output signal $f_c(i)$ are output by Folded Correlation 160. This is because not only positive peaks but also negative peaks folded-correlate positively with themselves due to multiplication (++=+, −−=−). Between the peaks, the noise folded-correlates with itself negligibly. The resulting output $f_c(i)$ as a whole recovers pulses that follow S1 and S2 heart sounds well.

Succeeding thresholding passes the S1 peaks and counts them. Robust detection of primary heart sounds and heart rate from a chest-worn accelerometer is thus achieved in the presence of interfering motion artifacts. Such capability is directly relevant in applications that involve ambulatory monitoring of cardiovascular and cardio-respiratory health.

Applications include: home health monitoring, fitness applications (exercise monitoring), hospital and ICU (intensive care unit) patient monitoring, and patient monitoring at accident sites, in ambulances, gurneys or rolling patient transfer beds, in mobility aids like scooters and wheelchairs, and other mobile and/or fixed environments in a setting that is related to a hospital, clinic, allied medical testing facility, residence, commercial establishment, airport or otherwise.

Heart signal components may have S1, S2, and heart murmur components. Some embodiments further process heart signal components by coupling the circuitry and signals described herein to processing according to the teachings of U.S. Patent Application Publication 20090192401 "Method and System for Heart Sound Identification" dated Jul. 30, 2009 (TI-65798), which is incorporated herein by reference.

Data used for the evaluation of the methods is collected from six healthy young volunteers. Ambulatory conditions were simulated by the subject walking 2-3 minutes at normal speed.

Table 2 shows the accuracy, number of false positives and number of false negatives for the subjects collectively. Most of the false negatives were due to S2 misses.

TABLE 2

ERROR ANALYSIS OF RESULTS

| Accuracy | 99.36% |
| --- | --- |
| False Positives | 1.3% |
| No. of S1 misses | 2 (0.085%) |
| No. of S2 misses | 13 (0.55%) |

Figure 11:
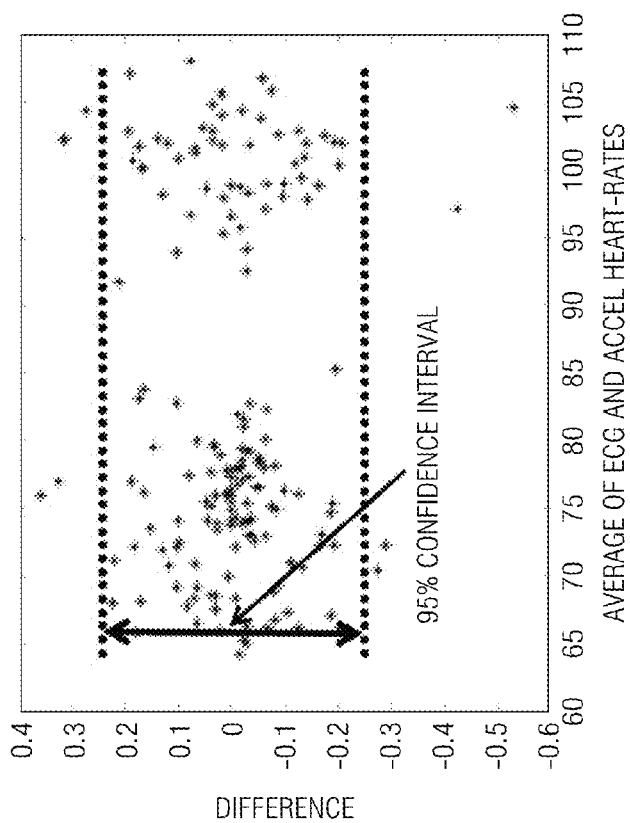
FIG. 11 is a plot of the difference of two heart-rate measures (inventively filtered accelerometer-based and ECG-based) versus their average.

FIG. 11 shows a Bland-Altman plot for heart rates (calculated over every 5 second time segment) for all of the subjects from ECG data and heart rate estimates obtained from the processed accelerometer data. The difference of the two heart-rate measures (accelerometer and ECG) is plotted versus their average. A few outliers are caused by false positives, but overall, most of the data is within a 95% confidence interval. For heart rate calculation both S1 and S2 locations were used. The results are robust over both lower and higher heart rates.

In some embodiments, the odd peaks from the output of a simple form of the peak detector are picked as S1 and the even peaks as S2. This type of selection may lead to some errors since a single false peak can cause the error to ripple along. The effect of this is mitigated to some extent by a choice of performance measures that look at relative time displacement or distance in time as opposed to absolute location in time. Nonetheless, the simple form of the peak detector and process locates most of the S1 and S2 events with very few false positives. In some other embodiments, to reduce S2 false negatives and reduce false positive rate even further, the peak detector is augmented with a circuit or process that incorporates amplitude and S1-S2 interval information to select the S1 and S2 peaks from the output of the peak detector.

Figure 12:
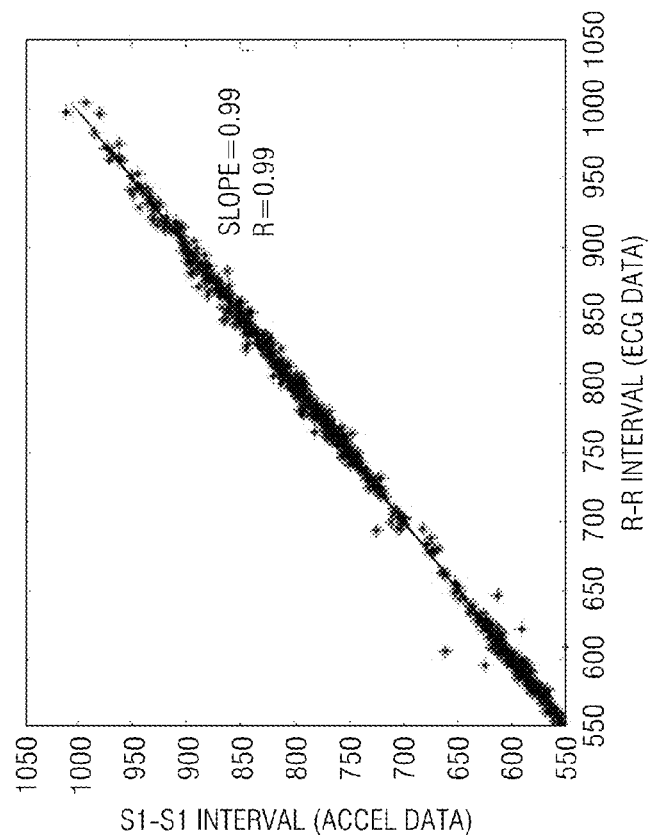
FIG. 12 is a plot having time interval between adjacent S1 cardiac pulses from inventively filtered accelerometer data on one graph axis, versus ECG R-R interval on the other graph axis.

In FIG. 12, to further illustrate the ability of a process embodiment to locate S1 events robustly, the peak detection is made to pick only S1 events. FIG. 12 shows a plot of Cardiac Interval from S1 locations from accelerometer data (S1-S1) on the graph vertical axis, versus ECG R-R interval on the graph horizontal axis. As seen from FIG. 12, a high correlation (correlation coefficient of 0.98) between the cardiac periods was obtained from the different measures. The slope of the least squares fit is 0.99.

Benefits are obtained by themselves and with other benefits by structures and processes described elsewhere herein and in the simultaneously-filed TI-68552 and TI-68553 patent applications, which are incorporated herein by reference.

Description turns next to a set of embodiments that separate and derive motion/activity, heart-rate and respiration from a single signal from a single chest-worn sensor such as a miniature Z-axis accelerometer sensor. Ambulatory measurement of respiration and cardiac activity can find wide application in home health monitoring of older adults and of patients with a history of cardiovascular, respiratory, and other conditions for which respiratory and/or cardiac monitoring are desired. Evaluating cardiovascular performance of patients in ICU and hospital settings, in mobile ambulances, and at accident and trauma sites also calls for ambulatory cardiac and respiratory measurement and monitoring. Conventional solutions for heart-rate and respiration monitoring are believed to be expensive, invasive or obtrusive and too cumbersome for ambulatory and continuous monitoring applications.

Figure 13:
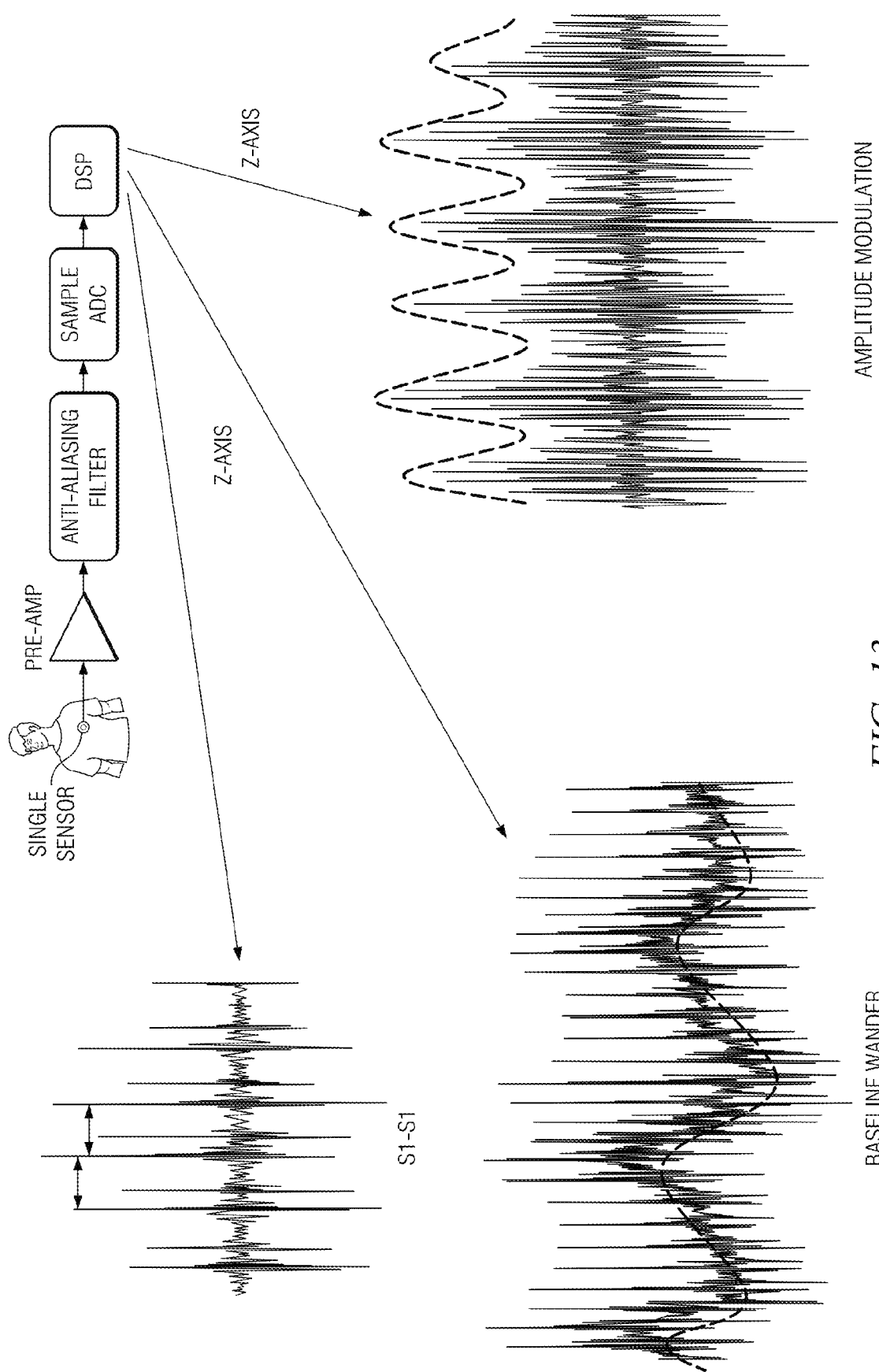
FIG. 13 is a partially-block, partially-pictorial, partially graphical depiction of an inventive structure and process for separating a respiration signal from heart and body motion and other signals using a single chest sensor.

Remarkably, various embodiments with a single, miniature, chest-worn MEMS accelerometer and associated monitoring circuitry measure and monitor respiration, motion and heart activity—reflected by heart sounds—as shown in FIG. 13.

In FIG. 13, embodiments are provided for ambulatory monitoring of heart-rate and heart sounds, activity, body motion and respiration in a non-invasive and minimally obtrusive way. Here, a single sensor, such as with a MEMS accelerometer, extracts not only heart-rate/heart sounds but also respiration in an ambulatory setting. Any signal is used that includes detectable heart sound signals from at least one sensor axis of the accelerometer sensor, or from two or more sensor axes. When a body motion signal component is included in the sensor signal, that body motion signal component is in some embodiments separated out or isolated and delivered as a useful output representing activity or motion as well.

Some advantages of various embodiments are extraction of three vitals (respiration, activity, heart sounds/heart-rate) from a single sensor and a single signal. A miniature sensor embodiment taped on the chest provides a non-invasive and minimally obtrusive way to sense and monitor vital physiological parameters in the presence of motion. Embodiments can be used with minimal inconvenience in ambulatory and continuous monitoring applications, and are very inexpensive and can be made into disposable patches and tapes, for instance.

In FIG. 14, a respiration waveform is obtained, for example, by a monitoring device embodiment of FIG. 13 and its process embodiment. The process in FIG. 14 receives the raw signal stream from the FIG. 13 ADC (analog to digital converter) and then first separates the heart sounds from the composite signal from the sensor using Savitzky-Golay (S-G) polynomial fitting followed by Folded Correlation and Peak Detection to deliver the S1 heart signal peaks. The heart rate is counted in response to the peak detection to provide a Heart-Rate signal output. Concurrently, the respiration is monitored by then measuring the successive times, called the inter-beat intervals or S1-S1 intervals, between heart beats—beat-by-beat. The variation in the measured inter-beat interval over time thus represents respiration because it is respiration-dependent and substantially independent of non-respiratory gross body motion. The monitoring device thus delivers as a respiration waveform that substantially represents the inter-beat interval varying over time. Further respiration processing counts the breathing rate and delivers a resulting breathing rate output, and derives and outputs any other useful information. In the meantime, the motion signal is extracted either from the S-G polynomial smoothing filter 130 as in FIG. 4 or by a low pass filter LPF with corner frequency at 2 Hz as shown in FIG. 14.

In FIG. 14, post-processing of the motion signals is applied to monitor and deliver waveforms representing average activity level over time, monitor walking gait and other motions, and detect a fall if one were to occur. Consequently, deriving motion or activity from an accelerometer is important, such as by the present embodiments. For instance, average activity level can be generated as the root-mean-square (RMS) of the motion waveform measured over an hour and output hour-by-hour. Walking gait can be derived from the Z-axis alone or in combination with signal streams from other accelerometer axes with respiration subtracted out. A fall is indicated such as by a peak detection of an unusually high-magnitude acceleration peak which stands out from any recent or subsequent neighbor peaks in a predetermined window of time such as +/−15 seconds. Some embodiments thus deploy motion-based analysis as a fall sensor as described herein or otherwise in any suitable manner enabled by an embodiment.

Process embodiments as in FIGS. 3-4 separate motion signal components from an accelerometer sensor signal to cleanly and robustly extract heart sounds, which enables the use of the accelerometer 210 to monitor heart sounds in the presence of motion and activity. Moreover, process embodiments as in FIGS. 13-14 separate motion signal components from an accelerometer sensor signal to cleanly and robustly extract heart sounds and use the accelerometer sensor to monitor not only heart sounds but also respiration (derived from heart sounds) in the presence of motion and activity, and further to deliver a motion/activity signal as well. In some embodiments, motion-based gating is performed to reject signal frames in the event that the motion/activity level is unusually high and does not permit reliable detection of heart-rate or respiration or some other derived signal under a given detection process. Reliable cancellation of motion artifacts from accelerometer signals to extract heart sounds is described, among other things, hereinabove and in the simultaneously-filed TI-68518 Patent Application, which is incorporated herein by reference.

In FIGS. 13-14, one example of a monitoring system embodiment has the same hardware and accelerometer sensor description as given in connection with FIGS. 1-4. Respiration monitoring is added as in FIG. 14. A reference ECG may be provided as discussed for FIG. 2.

Figure 15:
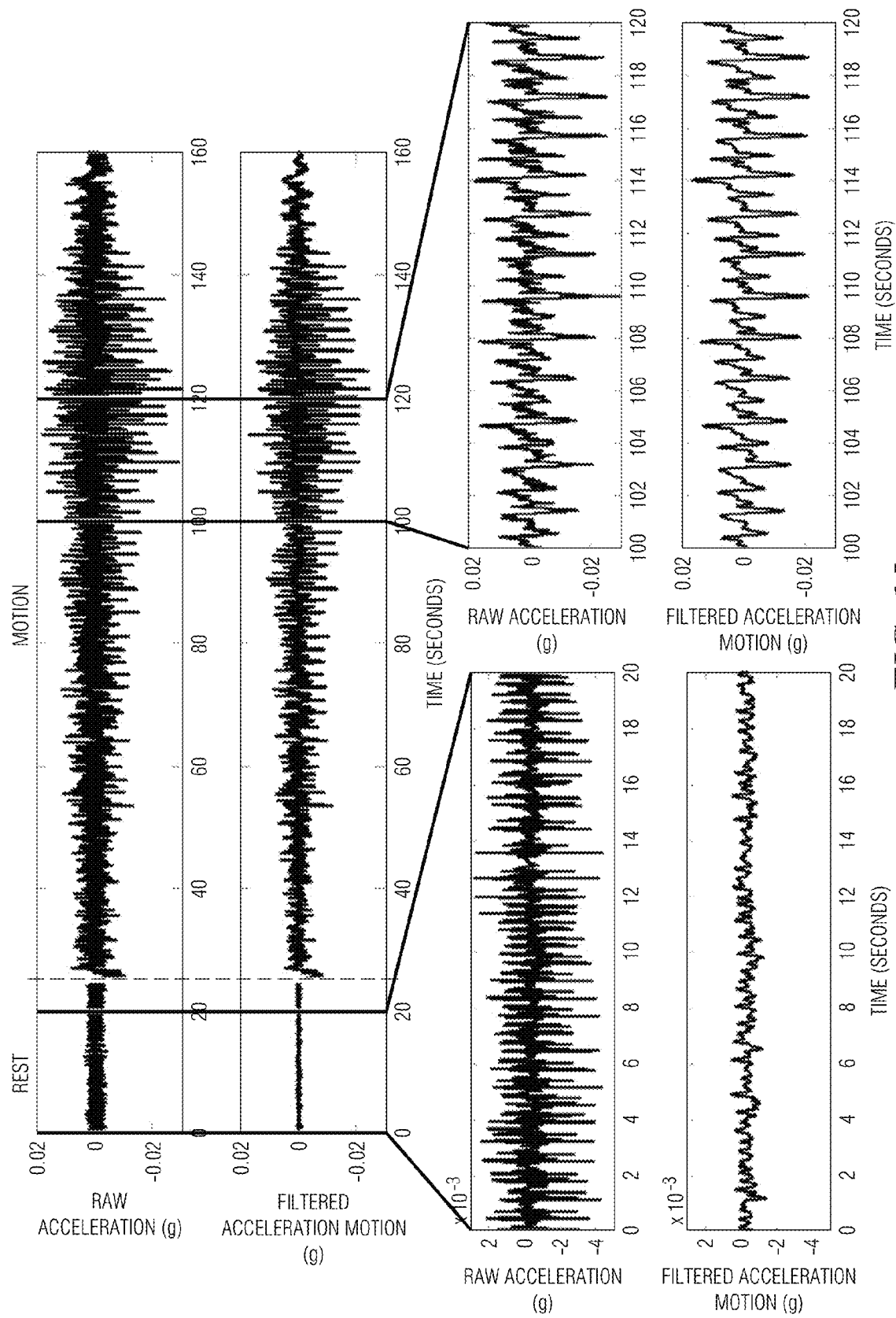
FIG. 15 is a pair of concurrent accelerometer-based waveform traces of voltage versus time in parts of the inventive structure and process of FIGS. 13-14 and shows a raw and inventively filtered accelerometer-based signal during rest and brisk motion. A time portion of the signals during rest is magnified in both voltage scale and time scale. A time portion of the signals during subsequent motion is magnified in time scale and not voltage scale.

In FIG. 15, detection of a body motion waveform is shown. The monitoring device measures gross body motion to sense and monitor activity and can provide a useful index of a person's level of activity over a period of time, and facilitate inferences about the person's lifestyle and metabolic index—jointly with ECG-derived heart-rate. Gait recognition by accelerometer-based motion monitor aids biometric assessment and can identify signs of or precursors to a dangerous fall. Also, using the accelerometer-based motion monitor as an indicator of sudden, high-magnitude acceleration can additionally identify signs of or precursors to a dangerous fall, as well as a fall itself.

In FIGS. 15 and 14, the signal obtained during motion from the chest-worn accelerometer is digitally low-pass filtered at 2 Hz—using a digital FIR filter—to extract the slowly varying baseline wander due to motion. For at least some cases of body motion as well as the body at rest, the respiration signal is well decoupled in frequency from the low-frequency body motion signal and is thus digitally low-pass filtered to successfully extract the respiration signal. FIG. 15 shows the raw and filtered motion signal extracted from the accelerometer during rest and brisk motion. Motion/Activity extraction from the accelerometer is conveniently achieved.

The implementer pays attention to physical attributes of the sensors in order to reduce unnecessary or activity-irrelevant motion artifacts. Coupling noise is reduced through good sensor location and placement and secure attachment of the sensor. Wire line noise or cable noise is kept low or eliminated by intelligent selection and placement and secure electrical and physical attachments. Wireless transmission is alternatively used to couple the hardware components of the monitoring system to reduce or eliminate body motion effects other than those picked up by the accelerometer itself and included in the acceleration signal(s).

Figure 16:
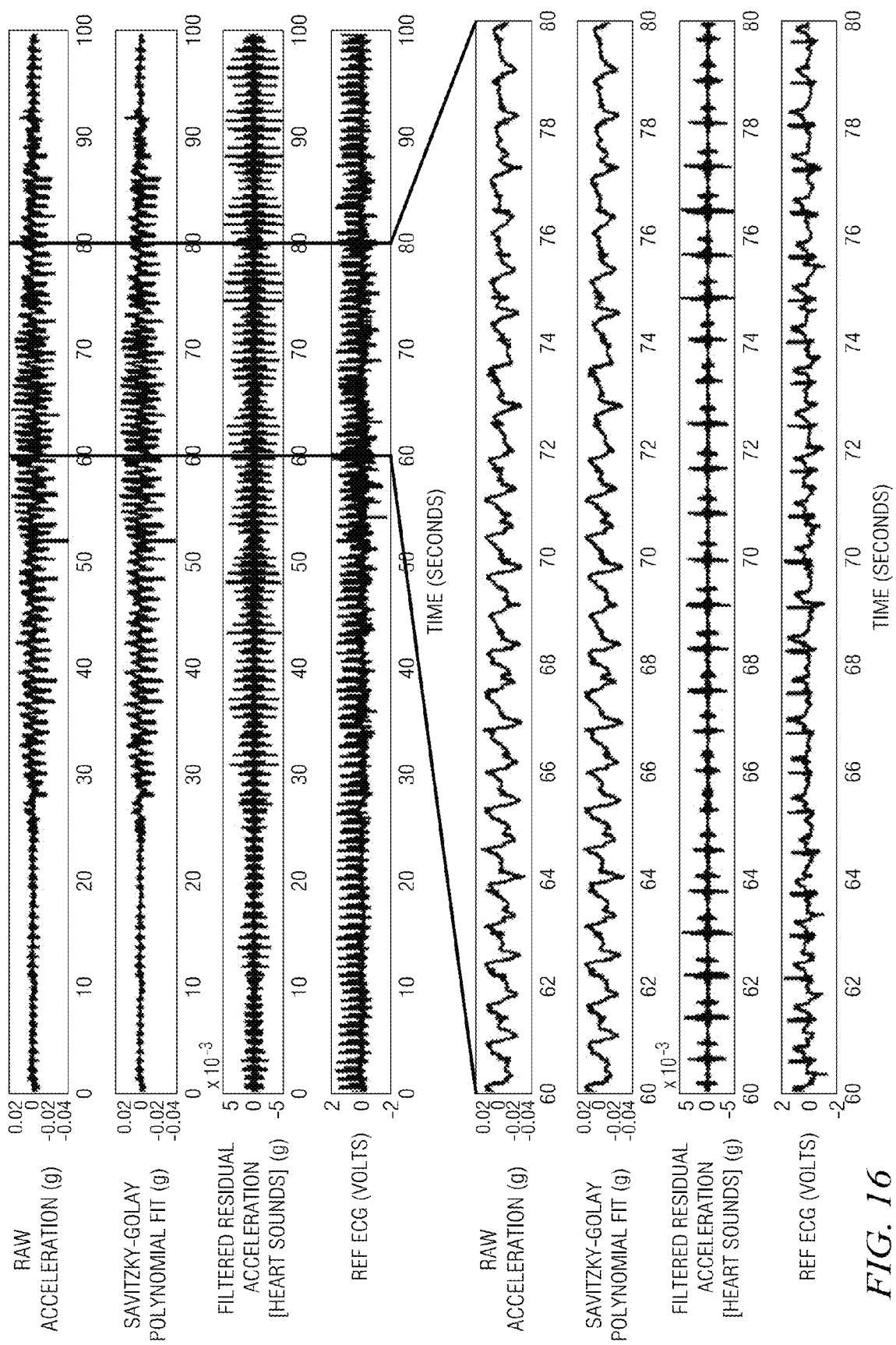
FIG. 16 is a set of four concurrent waveform traces of voltage versus time in various parts of the inventive structure and process of FIGS. 13-14 during motion and brisk walking. A time interval portion of the traces is magnified and shown as four time-magnified waveforms maintaining the same voltage scale for each. Some of the traces are inventively filtered accelerometer-based and one is ECG-based.

In FIG. 16, sensing, detecting, and monitoring heart rate, heart sounds, and cardiovascular and cardio-respiratory activity during motion and exercise importantly support continuous patient motoring and fitness applications, as well as at emergency and accident sites. The accelerometer-based extraction of primary heart sounds—S1 and S2 produced by the heart valve pairs closing at the ends of the diastolic and systolic periods respectively of the cardiac cycle—is robust in the absence or presence of motion, as shown in FIG. 16. The primary heart sounds are robustly detected through the S-G processing of the chest acceleration signal, not only during resting conditions, but also in the presence of strongly interfering motion—like walking.

In a respiration monitor example for FIG. 16, the S-G digital filtering 130 and residue generation 140 by the processor to obtain the heart sounds are as described in connection with FIGS. 3 and 4. Timing- and amplitude-based thresholding 150 and Folded Correlation 160 are applied as process steps of FIG. 4 as described earlier hereinabove. The Folded Correlation 160 in an example has a frame size of 7 at with the 1000 samples/sec that resulted from decimation. The peaks in FIG. 10 corresponding to S1 and S2 in the motion-removed acceleration signal are thus strengthened and are then peak-detected in step 170 for counting 180.

FIG. 16 shows as a first waveform the raw acceleration signal low pass filtered at 50 Hz. A second waveform represents the electronically-performed numerical polynomial fit g(i) corresponding primarily to the motion. A third waveform is the residue r(i) after subtracting the second waveform from the first waveform. The third waveform exposes or isolates the heart sounds, with motion-induced amplitude variations of FIGS. 13 and 16 as amplitude modulation thereon. In FIG. 16, the timing locations of heart sound components S1 and S2 show plainly and precisely, and they are largely independent of the amplitude modulation except for respiration-related variation of inter-beat interval. A fourth waveform in FIG. 16 is the simultaneously acquired ECG signal that is used as a timing reference or reference standard. Heart sound detection in the presence of motion is thus achieved.

Detection of respiration from the inter-beat interval has a physiological basis. Respiration modulates the heart rate, and consequently the inter-beat interval, by a phenomenon called respiratory sinus arrhythmia RSA, which is possibly responsive to respiration-related and other intrapleural or intra-thoracic pressure changes. The respiration-dependent variation in inter-beat interval is conventionally obtained from the R-R interval in the ECG recording. R-R interval robustly tracks respiration even during motion and exercise.

Figure 17:
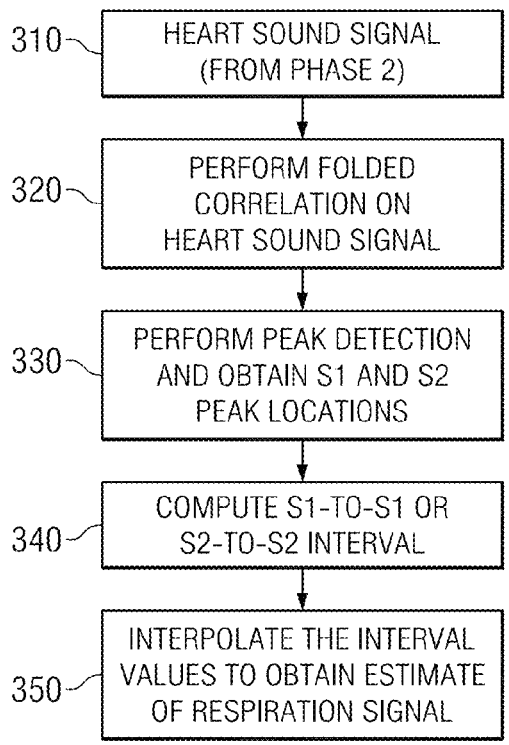
FIG. 17 is a flow diagram of a process for FIGS. 13-14 to separate a respiration signal from a heart signal and using inter-beat intervals of the heart signal, with both the respiration signal and the heart signal substantially separated from body motion and noise signals.
Figure 19:
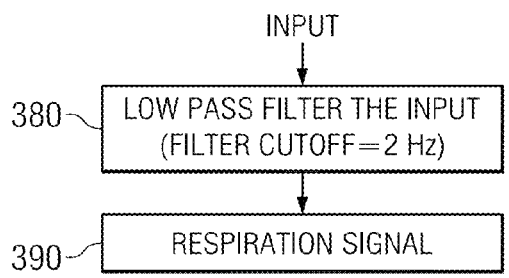
FIG. 19 is a flow diagram of another process for FIGS. 13-14 to separate a respiration signal from a heart signal according to baseline wander method herein for respiration monitoring by a single inventively filtered accelerometer sensor.
Figure 22:
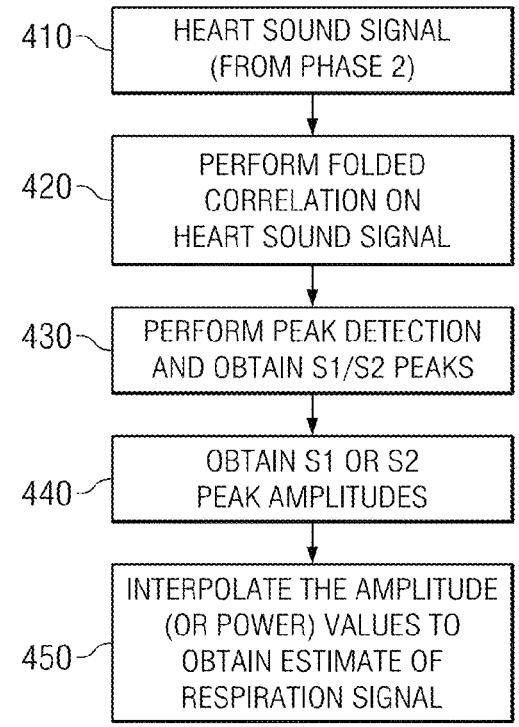
FIG. 22 is a flow diagram of a process for FIG. 13 to inventively separate a respiration signal from a heart signal by amplitude modulation detection of peak heights of the heart signal.

FIGS. 17, 19, and 22 respectively show three processes or methods of electronically generating respiration signal outputs from a sensor input. In various embodiments, these processes are used either individually, or in pairs, or a combination of all.

Some embodiments as illustrated in FIGS. 13, 14, 16 and 17 make the ECG recording optional, or obviate and eliminate the ECG recording, by deriving respiration from an accelerometer sensed-and-residue-detected variation in the S1-S1 interval during motion.

In FIG. 17, a process embodiment obtains the heart sound signal at a step 310 by removal of motion-dependent wander in Phase 2 of FIG. 4. The heart sound peaks are reinforced through Folded Correlation 320, and peak detection 330 is performed to detect the S1-S1 peaks. In a step 340, the S1-to-S1 interval (or S2-to-S2 interval) is repeatedly computed beat-by-beat to electronically obtain data values of successive inter-beat intervals. These data points are interpolated in a step 350 to yield a continuous respiration waveform of FIG. 18.

Figure 18:
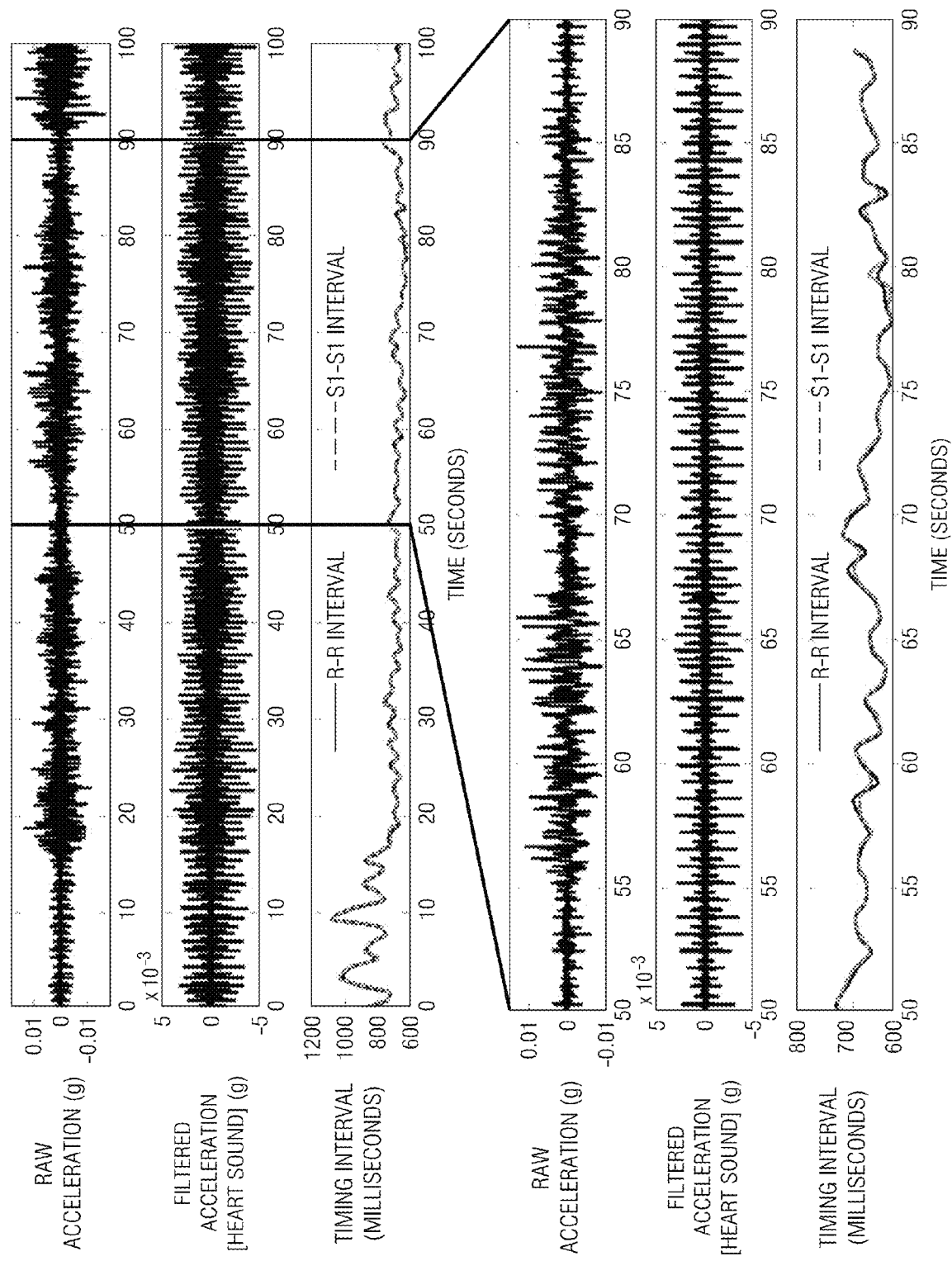
FIG. 18 is a set of three concurrent waveform traces of voltage versus time in various parts of the inventive structure and process of FIGS. 13-14, showing raw signal and inventively-obtained residue from filtered accelerometer-based signal, and further showing a respiration signal generated from ECG-R-R interval, and accelerometer heart sounds S1-S1 interval of the residue signal. A time interval portion of the traces is magnified and shown as three time-magnified waveforms maintaining the same voltage scale for the first two, and magnifying the voltage scale for the respiration signal.

In FIG. 18, a first waveform shows the raw acceleration signal fed from the 50 Hz LPF to the smoothing filter in FIG. 4. A second waveform shows the residue signal that delivers filtered heart sounds S1/S2. A third waveform shows a varying inter-beat interval—the S1-S1 Respiration-related waveform—derived according to the process of FIG. 17 and superimposed on a concurrent ECG (R-R) derived respiration waveform. The fit is quite favorable, as disclosed by inspecting the two different scales of illustration in FIG. 18.

In FIG. 19, another process embodiment is called the baseline wander method herein for respiration monitoring by a single accelerometer sensor. This process in a step 380 operates on the raw accelerometer ADC signal input from a person at rest by low-pass filtering it with a filter cutoff frequency at about 2 Hertz, or otherwise selected, e.g., with LPF cutoff in a range of about one (1) Hertz to about three (3) Hertz. A waveform called Baseline Wander thus obtained as an electronic respiration signal at a step 390, with example waveforms shown in FIGS. 20 and 21 for comparison with respiration outputs from each of the processes of FIGS. 17, 19 and 22. In other words, breathing periods of about half a second or more are passed, so that not only resting breathing periods of a breath every two or three seconds are detected, but also breathing periods under stress or after exercise down to about a third or half a second are detected. Shorter period signal variations in the accelerometer are suitably obtained from the S-G filter smoothing or by other types of filtering to represent body motions other than respiration.

Figure 20:
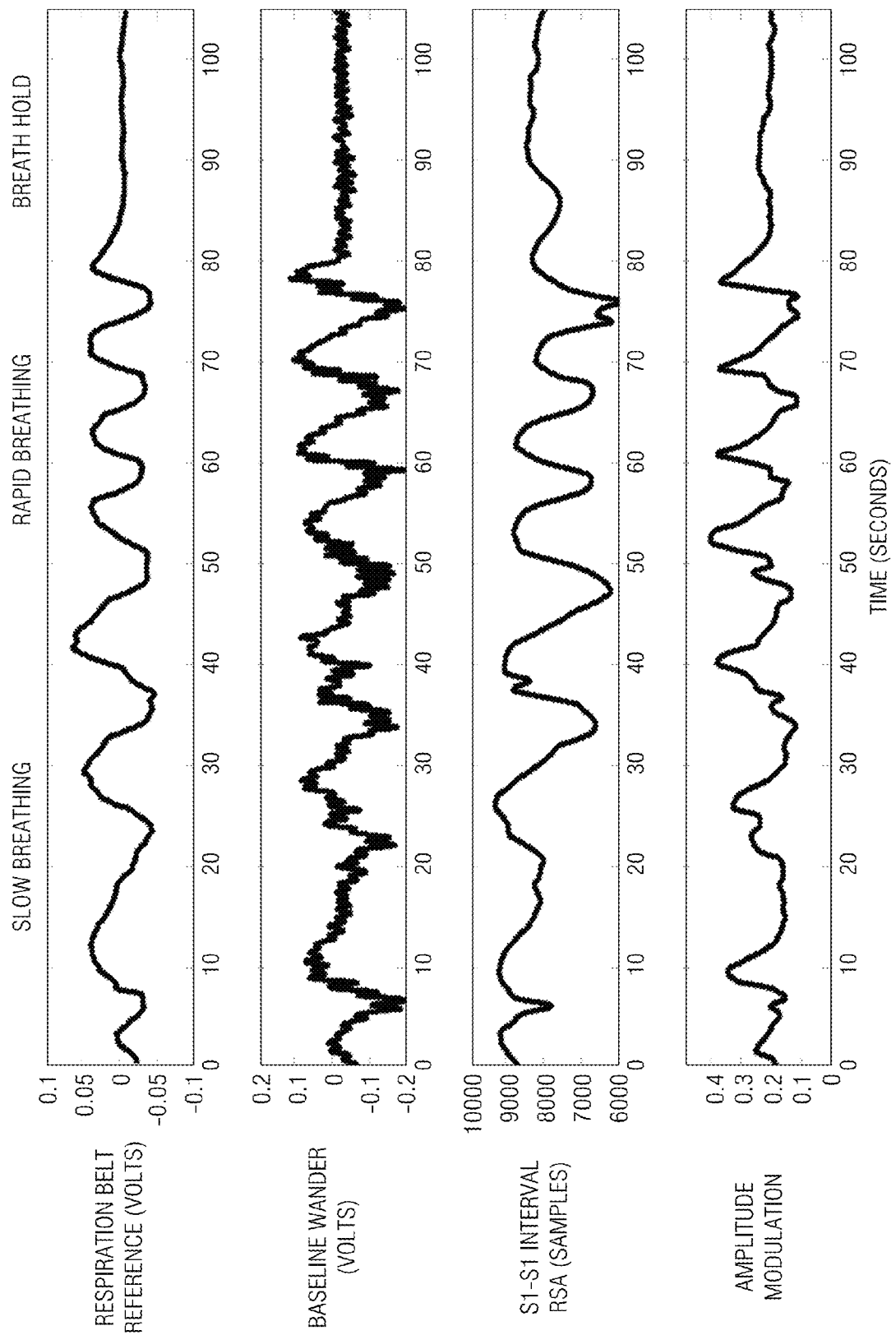
FIG. 20 is a set of four example waveforms of voltage versus time and shown for comparison of a respiration belt signal with respiration outputs from each of the processes of FIGS. 17, 19 and 22.

In FIG. 20, a comparison of concurrent waveforms of respiration generated by different embodiments is shown along with a reference respiration waveform obtained from a respiration belt or spirometer. A second waveform shows a baseline wander signal using the process embodiment of FIG. 19. A third waveform shows the varying inter-beat interval method or process of FIG. 17 (RSA: S1-S1 interval), and a fourth waveform shows output from a heart sound amplitude modulation process embodiment of FIG. 22.

Figure 21:
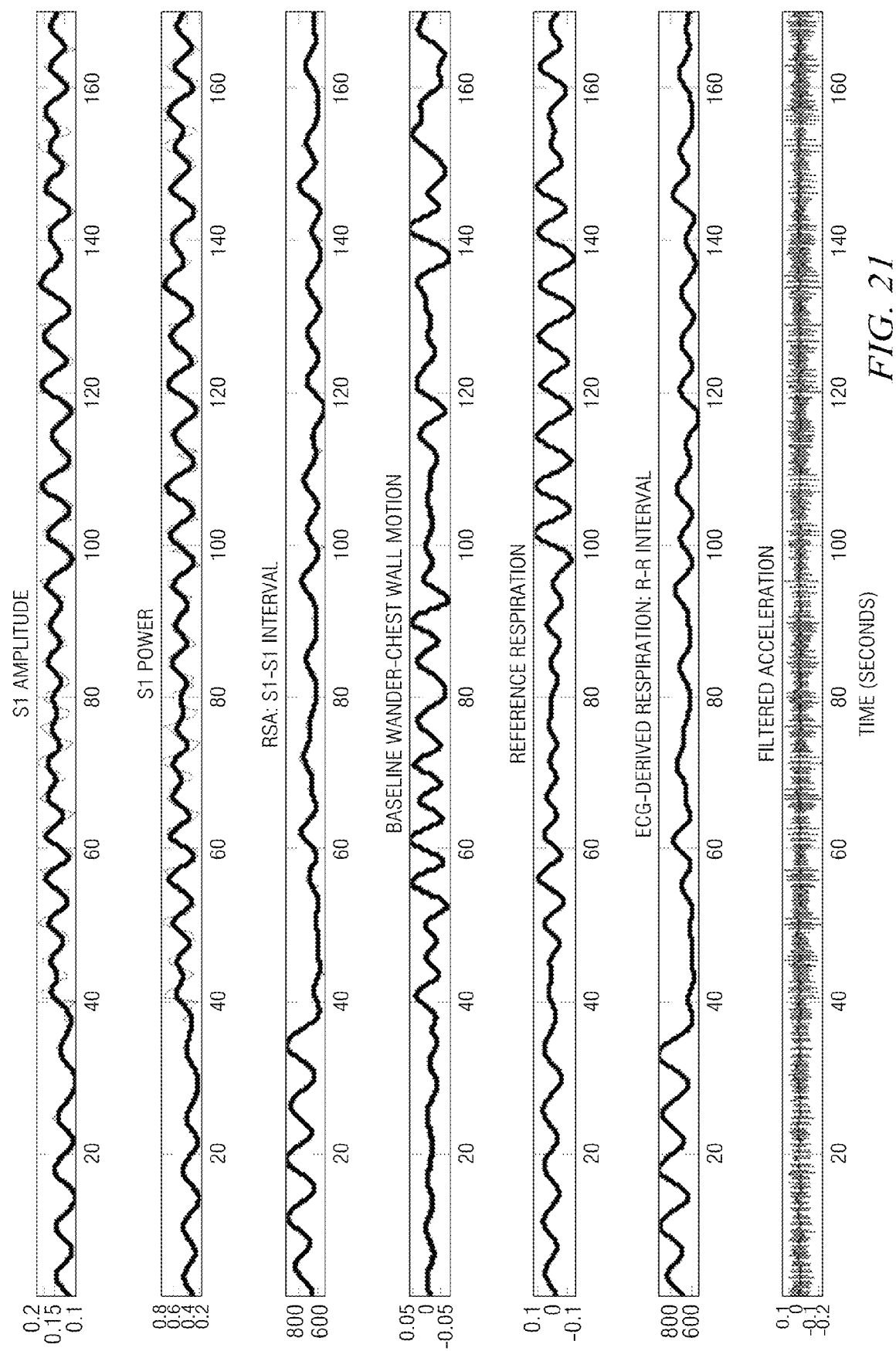
FIG. 21 is a set of seven example waveforms of voltage versus time, including a comparison of a reference respiration signal and ECG-derived respiration signal with respiration outputs from each of the processes of FIGS. 17, 19 and 22.

In FIG. 21, another comparison of concurrent waveforms of respiration generated by different embodiments is shown. A first waveform shows the variation of S1 amplitude output from a heart sound amplitude modulation process embodiment of FIG. 22. A second waveform shows a trace of S1 power obtained by further processing the first waveform. A third waveform shows the varying inter-beat interval method or process of FIG. 17 (RSA: S1-S1 interval). A fourth waveform shows a baseline wander signal using the process embodiment of FIG. 19. A fifth waveform shows a reference respiration signal. A sixth waveform shows an ECG-derived respiration signal from inter-beat interval obtained from the R-R interval of the ECG. A seventh waveform shows a trace of filtered acceleration.

In FIG. 22, a further process embodiment, for respiration monitoring by a single accelerometer sensor 210, obtains the heart sound signal at a step 410 by removal of motion-dependent wander in Phase 2 of FIG. 4. The heart sound peaks are reinforced through Folded Correlation 420, and peak detection 430 is performed to detect the S1 peaks. These S1 peaks are amplitude modulated as shown by the second (middle) waveform of FIG. 23. Instead of (or in some embodiments in addition to) inter-beat interval measurement as in FIG. 17, the successive S1 peak amplitudes (or S2 peak amplitudes) in a step 440 are repeatedly measured electronically beat-by-beat in FIG. 22 to electronically obtain data values of successive heart sound peak amplitudes. These data values are interpolated in a step 450, such as by linear or quadratic or other interpolation, to yield a continuous respiration waveform. Examples are comparatively shown as the first and second waveforms of FIG. 21 for amplitude and power respectively.

Figure 23:
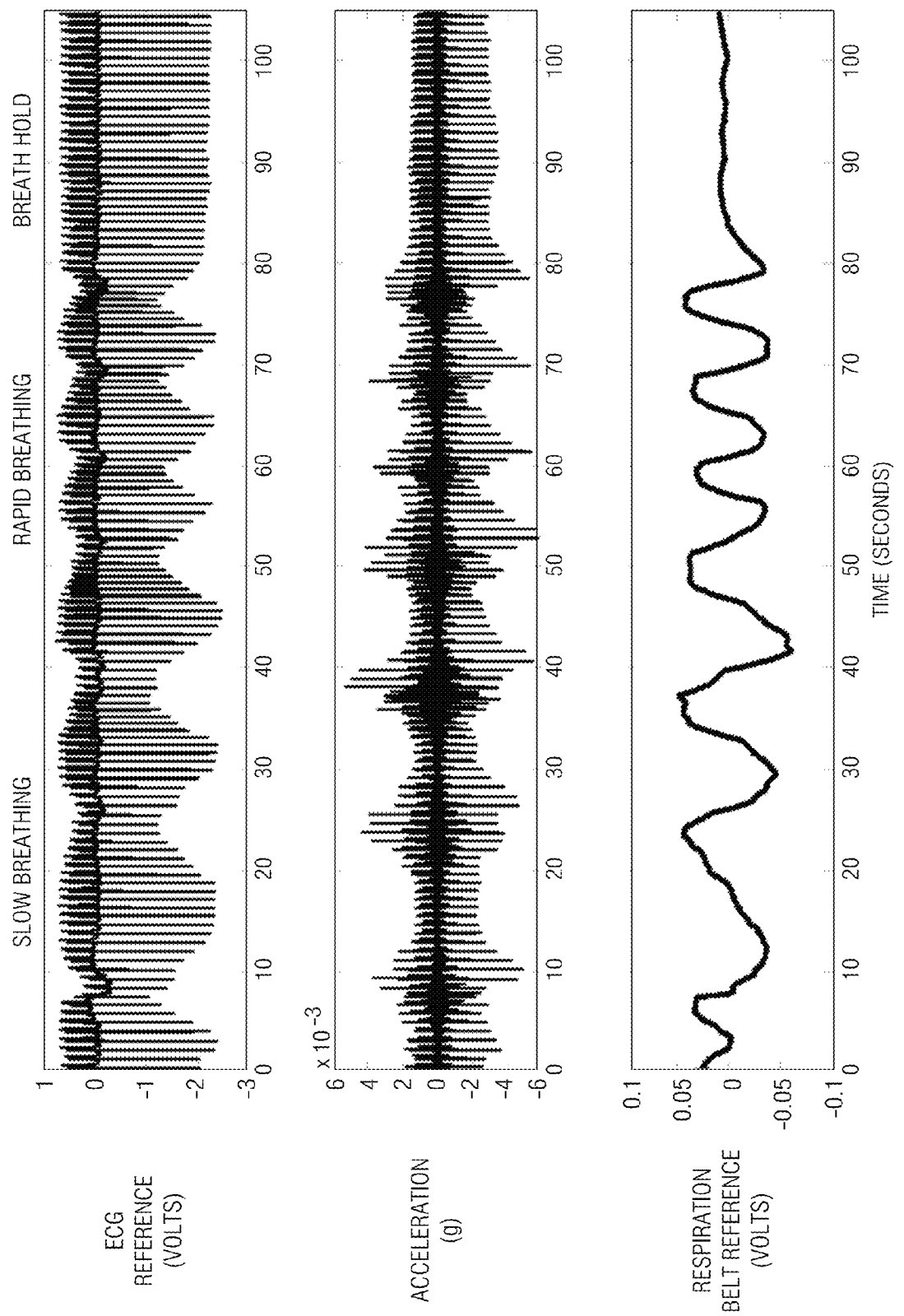
FIG. 23 is a set of three concurrent waveform traces of voltage versus time in various parts of the structure and process of FIGS. 2 and 13 and 22, showing ECG amplitude modulation on the R peaks, and further showing amplitude modulation on the S1 peaks from inventively filtered accelerometer based sensing, and also showing a respiration signal obtained from a respiration belt for reference.

FIG. 23 illustrates the close correspondence of respiration measurements obtained in different ways. In a first waveform from ECG, amplitude modulation rides on the R peaks. Amplitude modulation rides on the S1 peaks in the second (middle) waveform from accelerometer based sensing according to the process embodiment of FIG. 22. The S1 amplitude modulation correlates well, as seen by comparison with the R amplitude modulation on the first waveform from ECG. A third waveform shows a respiration signal obtained from a respiration belt for reference.

Figure 24:
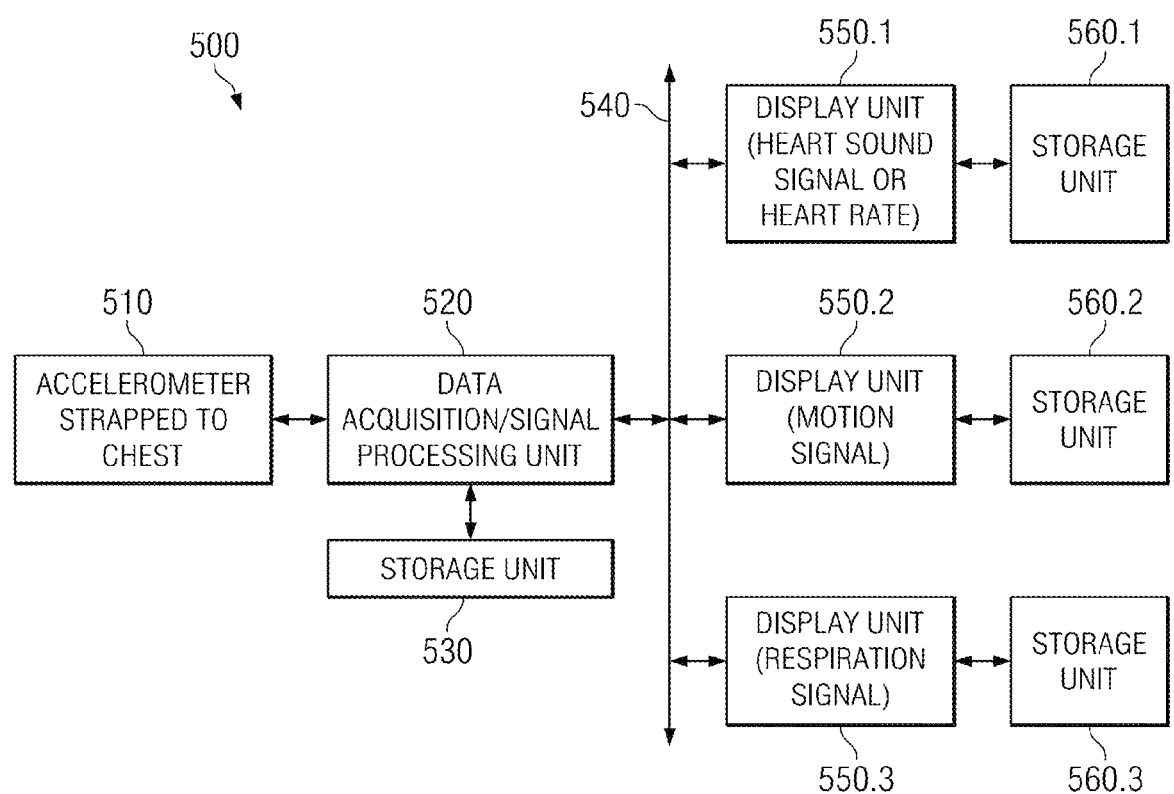
FIG. 24 is a block diagram of an inventive wired system structure and process and including inventive structures and processes from the other Figures.

FIG. 24 shows an implementation of a wired system embodiment 600 for a respiration and cardiac monitoring system. An accelerometer 510 is strapped to the chest of the person being monitored. An axis sensor signal is coupled to a data acquisition signal processing unit 520 having a stream data interface and an associated data storage unit 530 for the signal stream and for instructions and parameters. The signal processing unit 530 supplies process monitoring data to one or more display units 550.*i*, each having a respective data storage unit 560.*i*. A first form of display 550.1 shows the heart sound signal and/or heart rate. A second form of display 550.2 shows the body motion signal. A third form of display 550.3 shows the respiration signal and/or respiration rate and/or or respiration depth (how deeply the person is breathing) and/or other respiration parameters. Various parameters for respiration are obtained from the respiration waveforms by finding various values on the waveforms and differences and trends therein. For example, respiration rate is measured as the number of cycles of inhalation and exhalation in a given time window (e.g. one minute). Averaging and signal fusion methods/algorithms are also usable in some embodiments to derive more robust respiration rates from multiple parameters. For instance, how deeply the person is breathing is represented by an average of the difference between successive values of inhalation peak and exhalation trough in a given time window (e.g. one minute). Averages and trends in the inhalation peaks are readily calculated and displayed. Averages and trends in the exhalation troughs are also readily calculated and displayed.

The system 500 of FIG. 24 is suitably arranged and physically protected for mobile and ambulatory monitoring environments. In other forms the system 500 is set up for use in a clinic by one or more clinicians concurrently.

Figure 25:
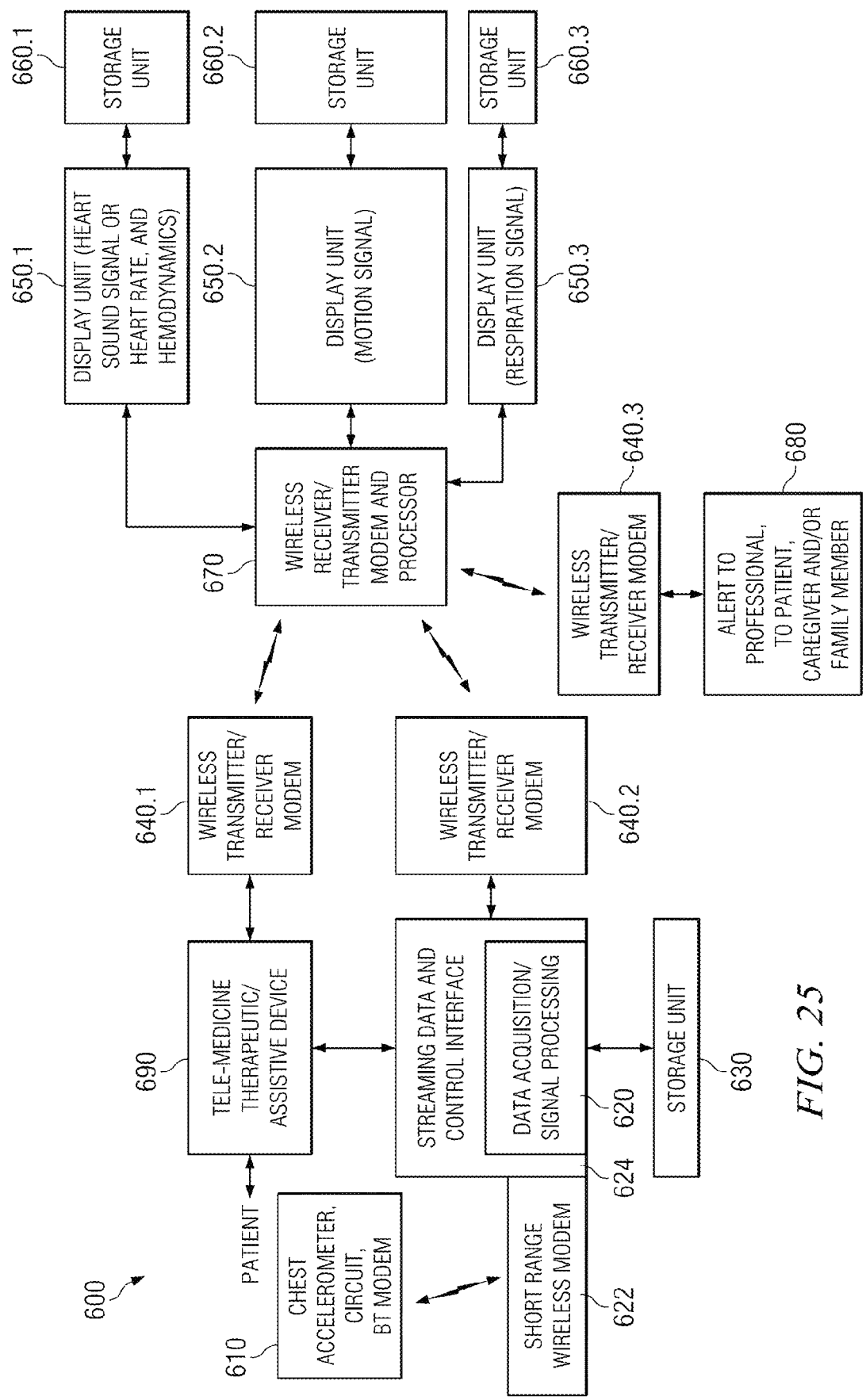
FIG. 25 is a block diagram of an inventive wireless system structure and process and including inventive structures and processes from the other Figures.

FIG. 25 shows an implementation of a wireless system embodiment 600 for a respiration and cardiac monitoring system including various remarkable device or component embodiments. The description parallels that of FIG. 24, except that the accelerometer sensor 610 and its electronic circuit also have a Bluetooth or other short range wireless modem wirelessly coupled to another short range wireless modem 622 that is coupled via a streaming data and control interface 624 to a data acquisition signal processing unit 620. Further, modems 640.2 and 670 for wireless transmission and reception remotely are provided at each of two locations so that the data acquisition signal processing unit 620 communicates via its modem 640.2 to the remote wireless transceiver unit or modem 670. The latter modem 670 is coupled to be one or more display units 650.*i* and their storage unit(s) 660.*i*. In this way, tele-medicine applications are supported. The acquisition signal processing unit 620 and its modem 640.2 are suitably provided in a residence or ambulance or on the person or in a wheelchair or gurney. The wireless transceiver 670 and display unit(s) 650.*i* are suitably provided in a clinic, hospital, medical monitoring center or otherwise. Either or both ends of the wireless system may be mobile, such as one example of a modem 640.3 and alert/processor/display 680 when a professional in a vehicle is urgently needed to review data coming in from a residence or another vehicle in case of emergency and to respond with instructions.

In FIG. 25, combinations with further processes, circuits and devices for automatic cautionary responses, warnings, and/or automated monitored therapeutic responses are contemplated. Upon occurrence of undue excursions of one or more measured parameters or relationships among parameters detected by signal processing unit 620, the remote processor 670 alerts any one or more of medical professional, patient, caregiver, and/or family member via a modem 640.3 and alert/processor/display unit 680 by sending a cellular telephone call and/or other voice call or message and/or written alert such as an automatic e-mail. The alert system suitably provides for acknowledgement by any of the recipients. Also, another modem unit 640.1 is suitably provided and coupled to a tele-medicine therapeutic or assistive device 690 for assisting the patient in some pharmacological, informational, or physically assistive way by administering a medicine, or adjusting a dosage or otherwise. In case of excursions that indicate an extreme medical emergency, the data acquisition signal processing unit 620 may be permitted to locally control the therapeutic or assistive device 690 temporarily and in a maximally-safe way until remote commands are received or first responders can arrive. Mere removal or inadvertent detachment of the accelerometer 610 from the chest is distinguished by the electronic processing 620 from affirmatively detected excursions of measured signals and parameters. Regarding telecare assistance, such assistance is suitably rendered in some physical way in response to the real-time accelerometer sensor 620 data by activating motorized apparatus comprehended by device 690 such as to adjust a motorized bed, or move a scooter into proximity for patient use, or servo-mechanically actuate and flush a toilet unit, or open a tub drain to empty a tub, or some other assistance.

In FIGS. 24 and 25, various parts of the systems 500 and 600 are each variously miniaturized and partitioned into various modules and provided with various types of wireline interfaces or wireless modems for different types of products. In this way, different system embodiments are provided. One type of embodiment forms a complete medical clinic system. Another type of embodiment is a patient-worn medical-sensor and/or therapeutic device that is wired or has a wireless modem. Another type of embodiment is a patient-worn signal processing and modem module on a belt clip that connects or wirelessly couples to such a sensor and wirelessly couples to a premises gateway or directly transmits to a remote location. Another type of embodiment includes the sensor, signal processor, memory, and modem together in a micro-miniature device that is taped to the chest and communicates to a router or gateway locally, and the latter communicates remotely. Another type of embodiment is the local router or gateway that includes signal processor, memory, and multiple types of modem to communicate with the sensor and separately communicate remotely, such as in a patient home-based system to telecommunicate to clinic or hospital. See FIG. 39 and FIGS. 40A/40B for an example of apparatus to support these various embodiments.

Respiration detection and monitoring for a person performing body motion or at rest are thus conveniently achieved along with cardiac monitoring. Local/remote assistance is suitably initiated responsively to such detection and monitoring. By contrast, conventional respiration measurement devices like respiration belts and spirometers are very susceptible to motion-dependent artifacts and/or are very unwieldy for continuous ambulatory monitoring. Various embodiments can therefore significantly facilitate the measurement of respiration in the presence of motion, or at rest. Benefits are obtained by themselves and with other benefits by structures and processes described elsewhere herein and in the simultaneously-filed TI-68553 and TI-68518 patent applications, which are incorporated herein by reference.

Description turns now to further embodiments for estimation of blood flow and hemodynamic parameters from a single chest-worn sensor. Embodiments are provided for measurement of blood flow trends (stroke volume, cardiac output) and other hemodynamic parameters (contractility, pre-ejection period, iso-volumic contraction interval) in a non-invasive and minimally obtrusive way. These measurements are believed to have been problematic, expensive, and inconvenient in the past. Conventional hemodynamic monitoring e.g., some forms of Doppler echo or impedance cardiograms, and some blood pressure monitors, may be expensive, invasive or obtrusive and too cumbersome for ambulatory and continuous monitoring applications. Here, by contrast, a single miniature sensor such as a MEMS accelerometer coupled with a data acquisition signal processing embodiment extracts hemodynamic parameters from the in-plane vertical accelerometer axis (Y-axis). These benefits are obtained by themselves and with the respiration detection and other features that are described hereinabove and in the simultaneously-filed TI-68552 and TI-68518 patent applications, which are incorporated herein by reference.

Among the advantages of some of the present embodiments, are:

a. Uses a single sensor and a single signal to extract several hemodynamic vitals such as any, some or all of changes in stroke volume, changes in cardiac output, heart-rate, iso-volumic contraction interval, etc.

b. Is minimally obtrusive (miniature sensor taped on the chest)

c. Can be used with minimal inconvenience in continuous monitoring applications d. Disposable patches/tapes carry the sensor and offer low cost and convenience.

Embodiments of system, circuits and process enable the use a single chest-worn miniature sensor (e.g., a dual-axis or triple-axis accelerometer) for the extraction of a signal closely related to the flow of blood from the heart. This enables extraction and assessment of other hemodynamic and cardiovascular parameters such as those discussed above and in the next several paragraphs.

Isovolumic contraction interval IVCI is the duration of an event during the early systole when the heart ventricles contract without any change in volume. During the isovolumic contraction interval the myocardial muscle fibers have begun to shorten but have not developed enough pressure in the ventricles to overcome the aortic and pulmonary end-diastolic pressures and thereby open the aortic and pulmonary valves. Such contraction interval occurs after the closure of the mitral and tricuspid valves and before the opening of the semi-lunar valves. Both pairs of heart valves are closed during this interval. IVCI can be estimated as the time difference between the peak of the S1 waveform (from the normal axis or Z-axis of the accelerometer) and beginning of the first peak of the vertical Y-axis accelerometer signal. This interval ICVI is expected to correlate well with the time difference in FIG. 32 between the time P1 of occurrence of the S1 sound and the peak location in time F1 of the flow signal.

Stroke volume SV is the difference between the end diastolic volume and end systolic volume and is a measure of the blood pumped by the heart per cardiac cycle. A conventional pulse contour method calculates a blood flow variable (milliliters/sec) from the pressure signal and computes the stroke volume by integrating the blood flow signal over a cardiac period. By embodiments of structure and process herein, a peak amplitude PAmp and Jamp of the flow signal derived by filtering from the accelerometer sensor is used to compute relative changes in the stroke volume. Stroke volume is computed by first applying a blood pressure signal, or a signal related thereto, to a model of the arterial system. One such model is called a non-linear Windkessel model, which regards the blood pressure as analogous to a voltage applied to a series-parallel network having a series impedance to a output, and a parallel resistor-capacitor combination across the output. These model circuit elements are modeled as non-linear to model behavior of the arteries as they expand under blood pressure. The blood flow is analogous to the voltage across the output of the circuit. The integrated output voltage over a period of heart rate S1-to-S1 is related to stroke volume for that period and is repeatedly computed. Some other models analogize a reflective electrical transmission line to the arterial system. Any model appropriate to the purposes at hand is employed.

Cardiac output CO is defined as the product of stroke volume and heart rate. CO is the volume of blood pumped by the heart per minute. Heart rate is obtained either by counting S1 pulses derived from an axis sensor of the accelerometer or counting R pulses using an ECG.

Pre-ejection period PEP is the time interval between onset of ECG QRS complex and the cardiac ejection. PEP is calculated from the beginning of the ECG QRS complex to the beginning of the first peak in the accelerometer signal, see FIG. 32. The R-F1 interval approximates the pre-ejection period.

Ventricular contractility VC measures the intrinsic ability of the heart to contract. Contractility can be estimated from the Stroke Volume SV. Increase in Stroke Volume causes an increase in contractility. Contractility VC may alternatively or additionally be measured by trending the pre-ejection period PEP.

Embodiments of structure and process herein are provided to monitor—by non-invasive and unobtrusive means—some or all of these vitals and others. Remarkably, a single, miniature, chest-worn MEMS accelerometer is processed to sense and measure blood flow and other hemodynamic parameters such as stroke volume variations—cardiac output variations, iso-volumic contraction interval; and jointly with a simultaneous ECG—contractility and pre-ejection period. The signal corresponding to and related to these parameters is picked up and extracted robustly from the accelerometer Y-axis, its axis parallel to or in the plane of the chest and oriented vertically if the patient is standing or seated vertically, or parallel to a line from head-to-feet (superior-inferior) if the patient is prone or otherwise not standing or seated vertically.

Figure 26:
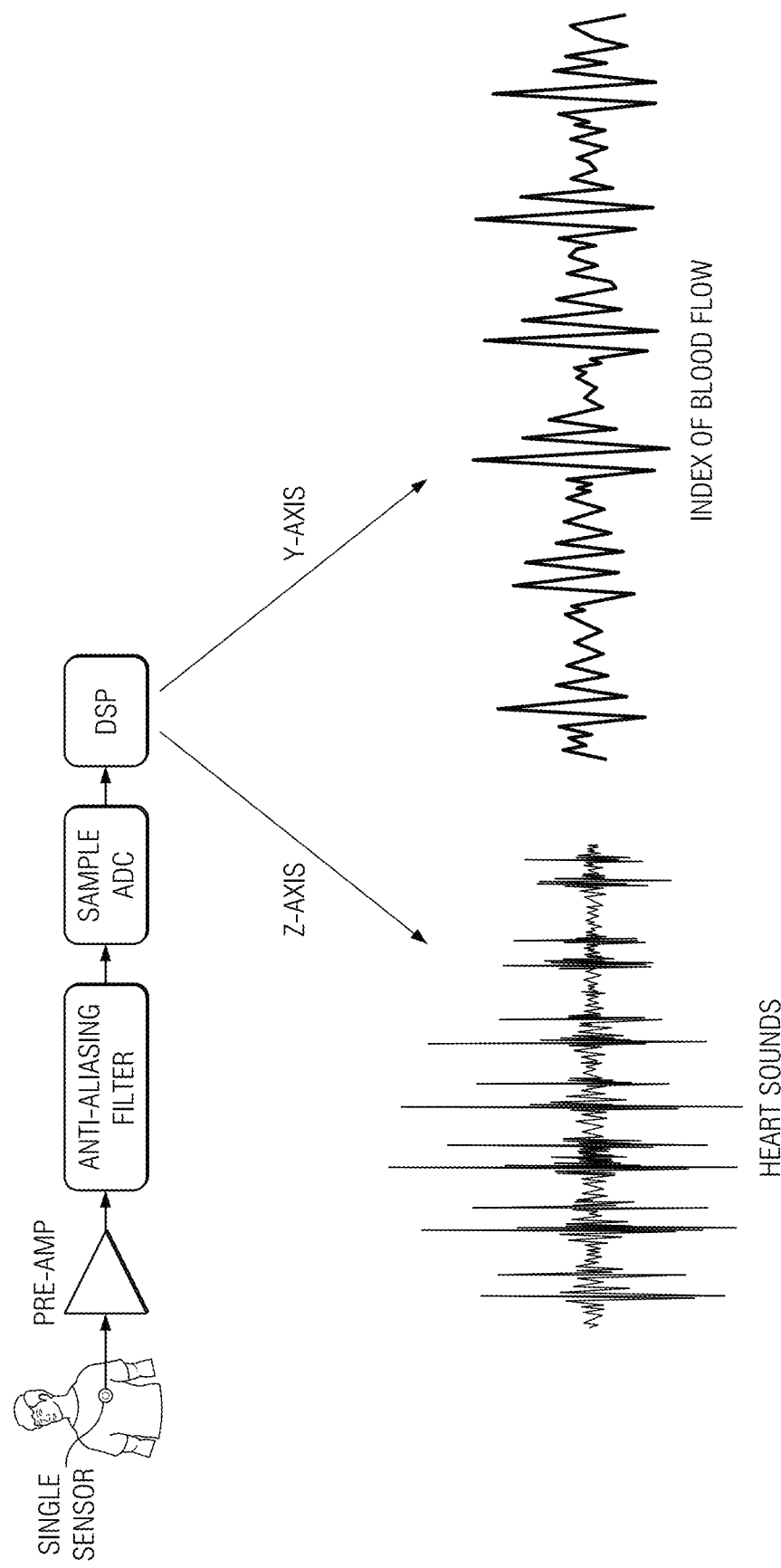
FIG. 26 is a partially-block, partially-pictorial, partially graphical depiction of an inventive structure and process for separating a blood flow signal from heart and other signals using sensor signals from one or more axes of a single chest sensor.
Figure 30:
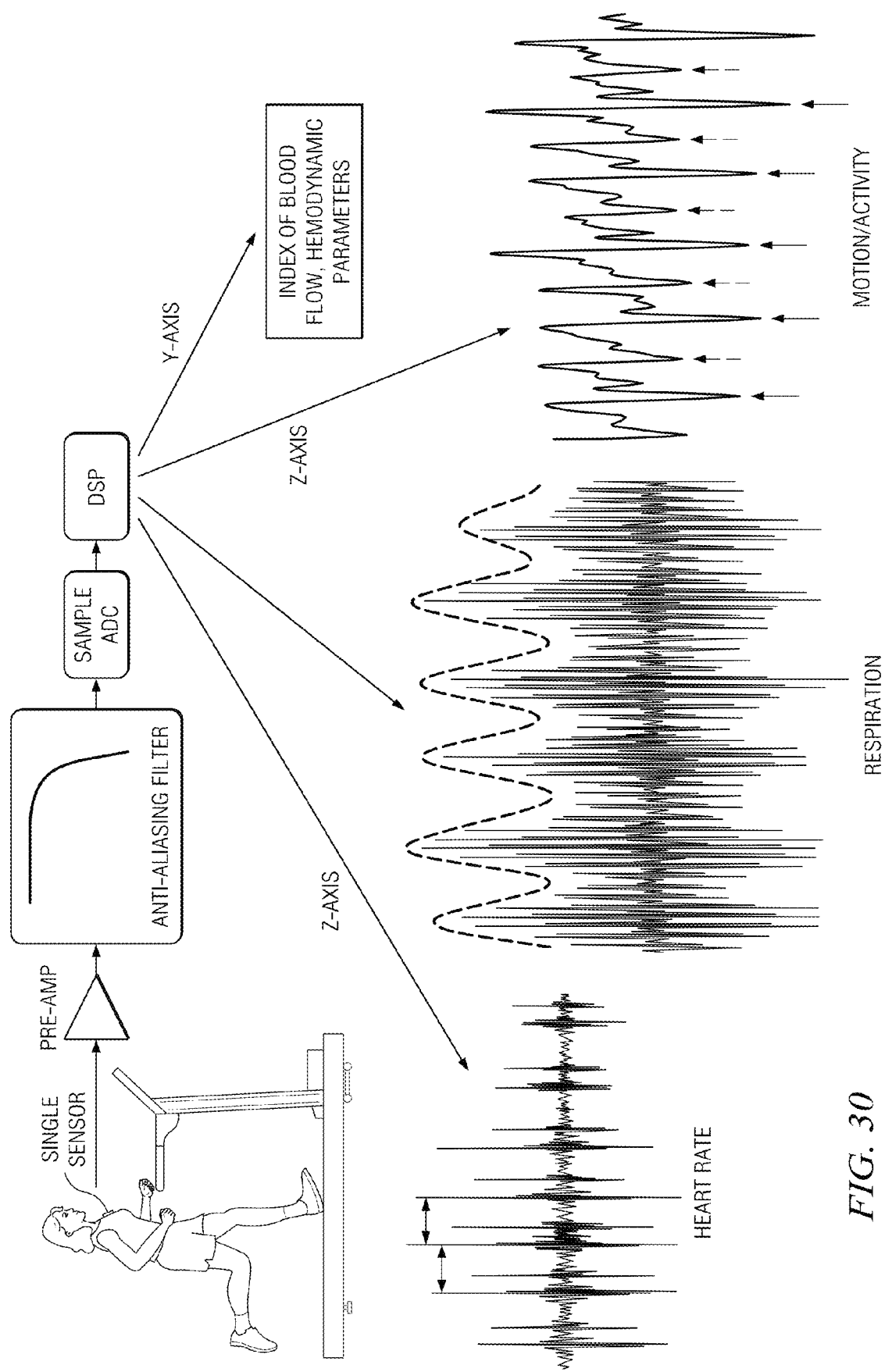
FIG. 30 is a partially-block, partially-pictorial, partially graphical depiction of another inventive structure and process for separating a blood flow signal and hemodynamic parameters, respiration signals, heart signals and motion signals from each other using sensor signals from one or more axes of a single chest accelerometer sensor.

In FIGS. 26 and 30, a system embodiment provides a convenient monitoring device and measurement set-up as shown. A miniature (weight—0.08 gram, size—5×5×1.6 mm) triple axis, low-power, analog output MEMS accelerometer (LIS3L02AL, STMicroelectronics, Geneva, Switzerland) is taped onto the chest and the acceleration signal along the Z-axis—orthogonal to the plane of the chest—corresponding to the heart sounds is captured. Simultaneously, the acceleration signal along the Y-axis—in the plane of the chest and oriented vertically upwards—corresponding to the blood flow and related hemodynamics is also captured by the same MEMS accelerometer. In this way, the acceleration signal along the in-plane vertical axis (Y-axis) is also captured.

The chest acceleration signals from both axes are, for instance, concurrently AC coupled (high pass rolloff was dropped about 10× in an example compared to the non-critical three (3) Hz described earlier hereinabove) and separately and in parallel are amplified with a gain of 100 and low pass filtered—for anti-aliasing—through a three-stage, 5-pole Sallen-and-Key Butterworth filters with a 1 kHz corner frequency. Two commercial quad operational amplifier packages (LT1014CN, Linear Technology, Milpitas, Calif.) are used for the analog front-end. The accelerometer signals are then each sampled at 10,000 (10 K) Samples/sec using a data acquisition card (National Instruments, Austin, Tex.) and captured and stored on a computer using MATLAB software (Version 2007b, The Mathworks, Natick, Mass.).

A reference ECG as in FIG. 2 is acquired simultaneously in a three electrode (single lead) electrocardiogram configuration for a reference in order to compare with the accelerometer-derived cardiac signal and also to extract information from the fusion (FIG. 33) of the electrical and mechanical signals (e.g., pre-ejection period PEP, contractility VC). An additional parallel signal path structure is replicated as described in the previous paragraph and used for the ECG signal.

Figure 31:
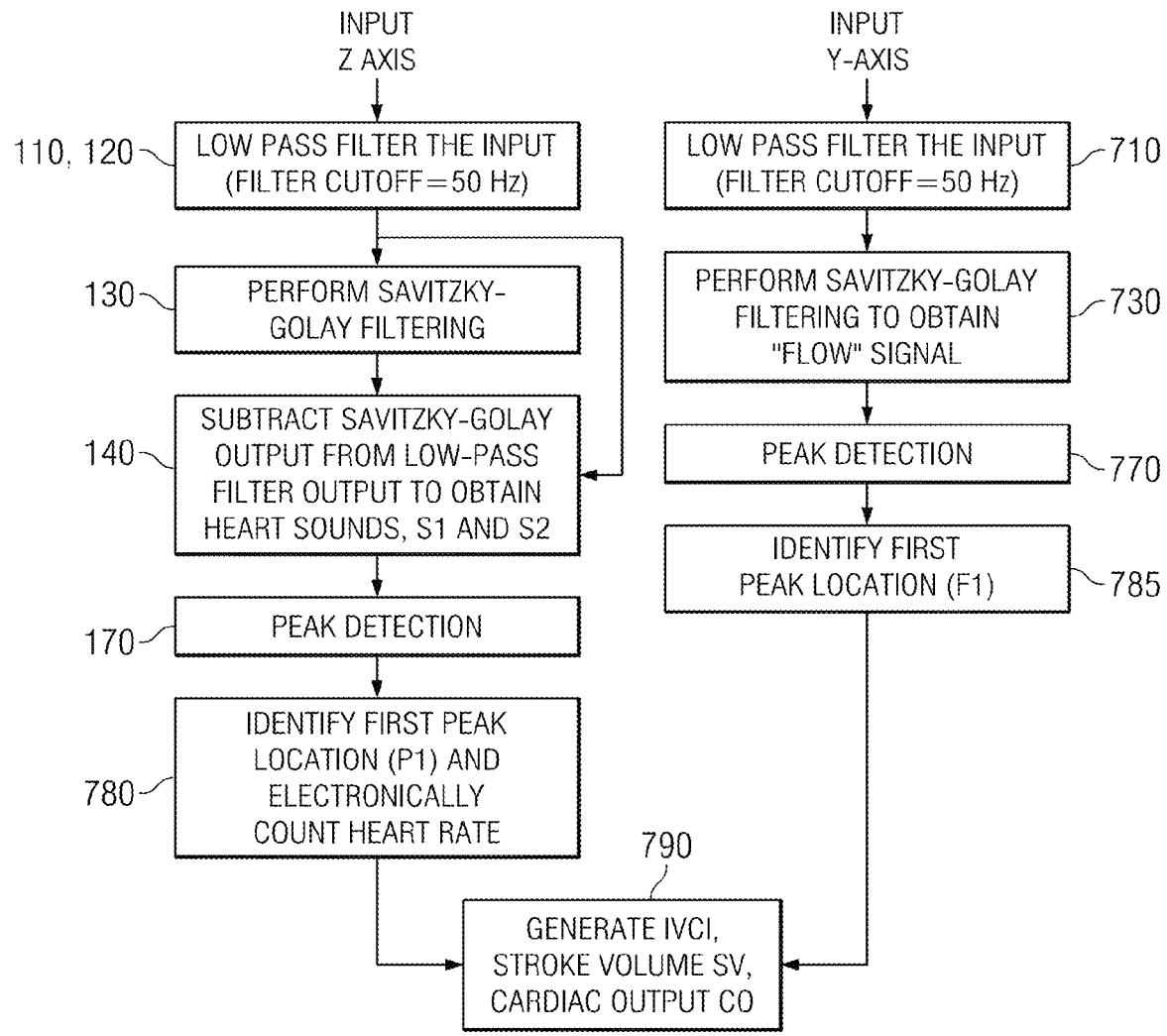
FIG. 31 is a combined flow diagram of inventive processes for separating a heart signal from body motion and noise using Z-axis sensor input and separating a blood flow signal using Y-axis sensor input from FIG. 30 and further electronically processing the heart signal and blood flow signal jointly to generate hemodynamic parameter signals for a display as in FIGS. 24 and 25.

The extraction of primary heart sounds (S1 and S2—produced by the heart valve pairs closing at the ends of the diastolic and systolic periods respectively of the cardiac cycle) uses a Z-axis sensor of the accelerometer worn on the chest. In FIG. 31 (and FIG. 4) the primary heart sounds are robustly detected through post-processing of the Z-axis chest acceleration signal as described earlier hereinabove, not only during resting conditions, but also in the presence of strongly interfering motion—like walking.

The acceleration signal acquired from a subject at rest is digitally low pass filtered at 50 Hz—using an FIR filter—and decimated by a factor of 10. The slow varying respiration baseline wander (e.g., sub-0.5 Hz respiration and body motion) is removed by smoothing filter and subtraction to yield a residue signal, and the primary heart sounds (S1 and S2) are detected through amplitude and timing based peak detection.

Figure 27:
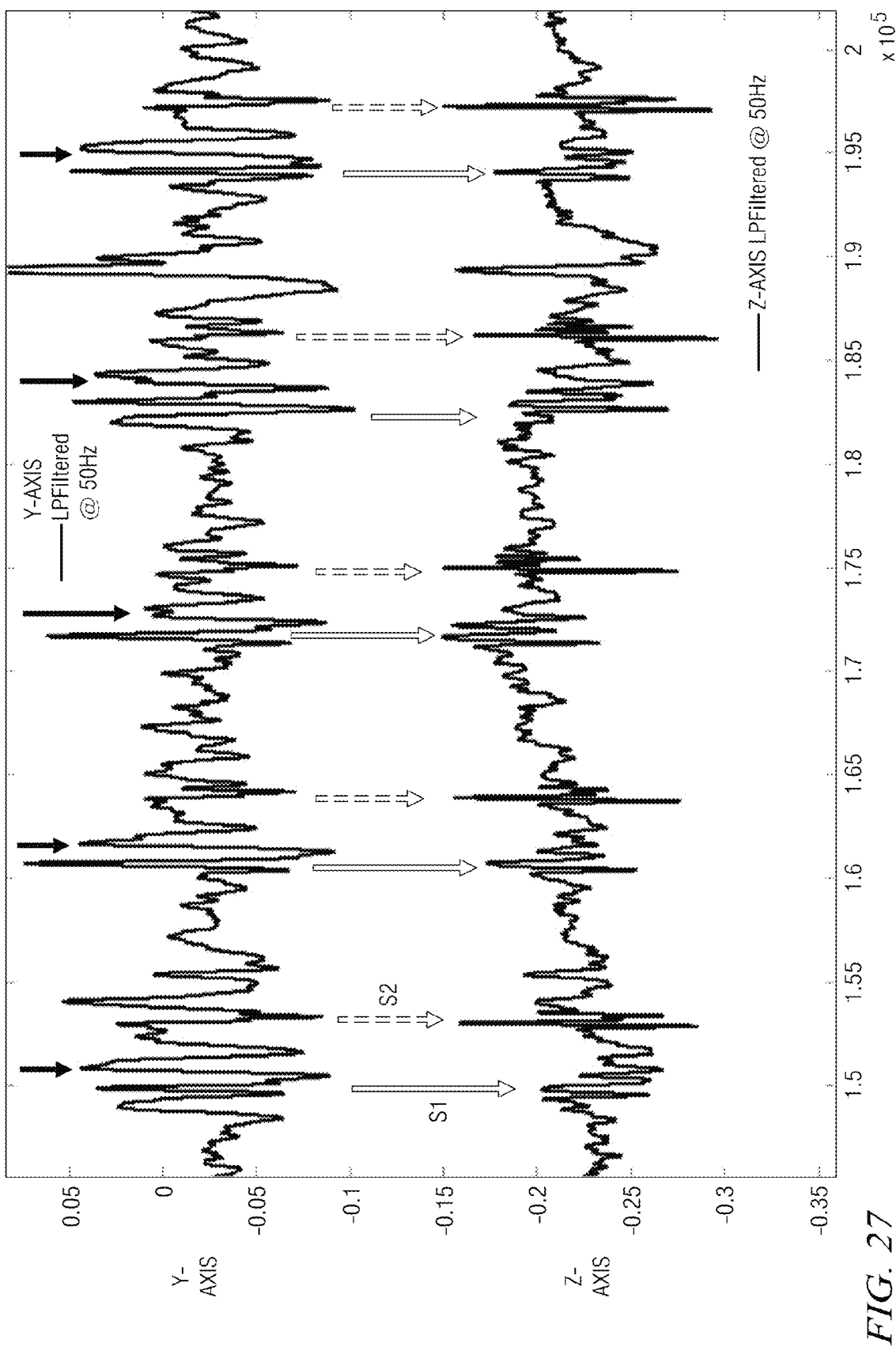
FIG. 27 is a pair of concurrent accelerometer-based waveform traces of voltage versus time of sensor signals from multiples axes of a single chest sensor in the inventive structures and processes of FIG. 26.

Hemodynamics from Y-axis: As shown in FIG. 27, striking differences were observed between the signals picked up by the Y-axis (in the chest plane) and the Z-axis. S1 and S2 align well in shape and timing in both axes, but the additional features (lower in frequency with the biggest peak between S1 and S2—marked at top in black arrows) occur very strongly along the Y-axis, but are hardly present in the Z-axis direction, as would be expected of a blood flow-related signal. In the description herein, the phrase flow signal or flow-related signal or blood flow signal is applied as a useful identifying label for this chest acceleration component, recognizing that the accelerometer is sensing a component of chest acceleration in meters/sec$^2$. This time-varying acceleration component may also be thought of as a body-reaction acceleration or skin-shear acceleration approximately parallel to the superior-inferior body axis in response to blood flow and is related in some way to an overall force of cardiac contraction in newtons and/or to systolic blood pressure in newtons/square meter and/or to blood flow acceleration in milliliters/sec$^2$ and/or blood flow velocity in milliliters/sec. Also, the dynamics of the blood varies spatially and with time at different points in the interior and along the blood vessels of the arterial system emanating from the heart. Arterial wall friction and elasticity are involved, and these change if hardening of the arteries occurs. With these considerations in mind, the accelerometer signal(s) are processed as described further and post-processed and interpreted in any appropriate manner by the skilled worker now and in the future to fully realize the benefits of various embodiments.

For example, the Y-axis signal is filtered or smoothed using a low order (4$^{th}$ order) Savitzky-Golay polynomial filter with a window size roughly 200 milliseconds. Different window length and polynomial orders are feasible. Also, specific polynomials and orders are illustrative and not limiting because they are related to the signal and the sampling rate. The smoothing filter extracts the slow varying (lower frequency) blood flow signal separated from the residue of the heart sounds (S1 and S2). Using Savitzky-Golay filtering as the smoothing filter is one of various possible ways of extracting the flow signal from the Y-axis. Slow varying respiration and body motion baseline wander (e.g., sub-0.5 Hz, below about one-half Hertz) is also removed or separated from the blood flow signal in some embodiments by either cascading or combining a high pass filter to attenuate the respiration wander, or using a smoothing filter to isolate the respiration wander and subtracting to yield a residue signal. Further in some embodiments, the respiration is separated from body motion as taught elsewhere herein. See filtering process discussion earlier hereinabove.

Figure 28:
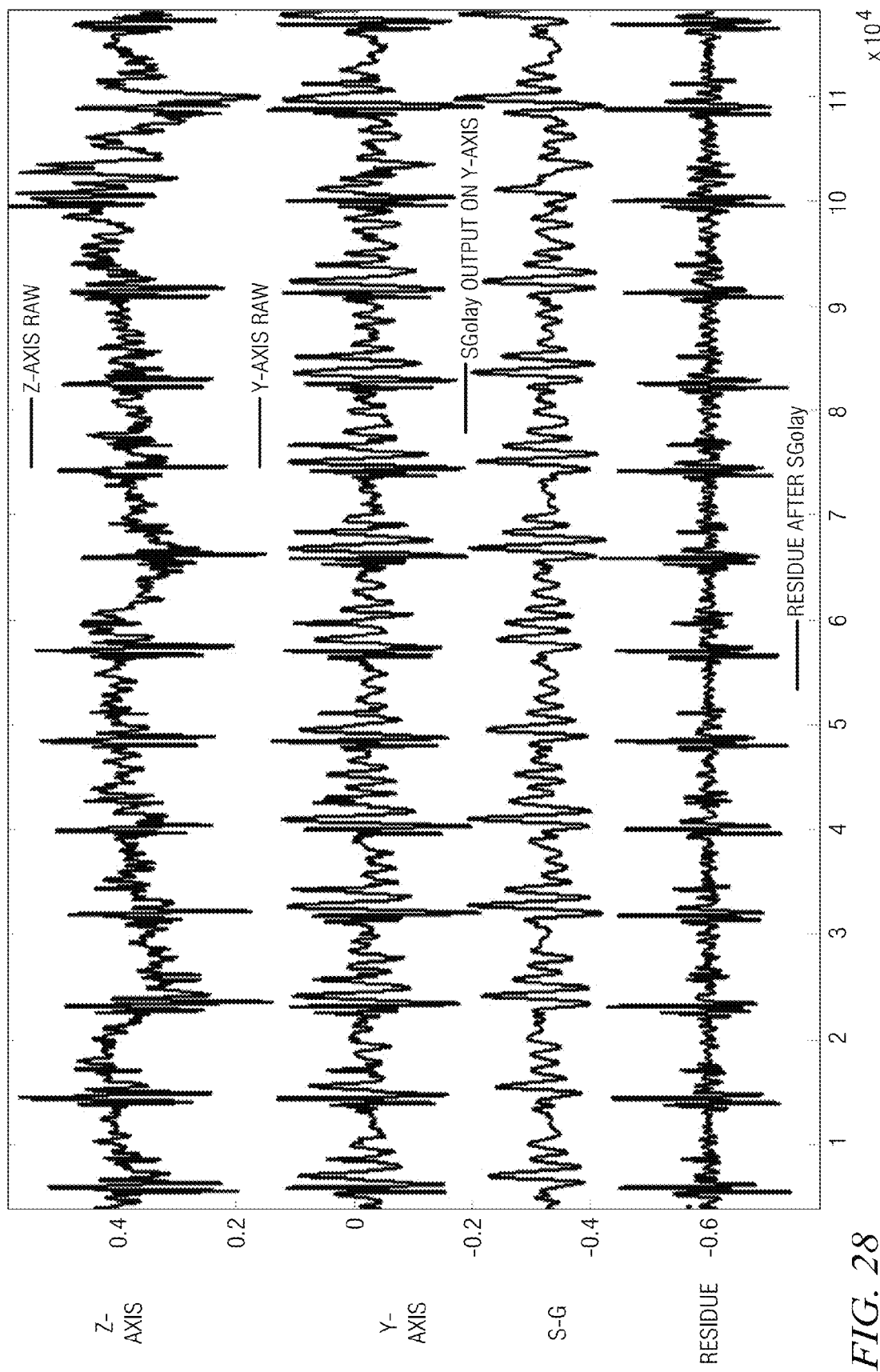
FIG. 28 is a voltage-versus-time graph of a pair of concurrent accelerometer-based waveforms from Z- and Y-axes of the single chest sensor, along with inventively filtered Y-axis signal and residue in the inventive structures and processes of FIG. 26.

FIG. 28 shows a first waveform with the raw Y axis signal and a second waveform with the raw Z axis signal. A third waveform traces the extracted flow signal from the S-G filter called a blood flow component, or flow signal, herein. Notice that the 200 msecs window size nicely encompasses either straight or curved portions within a cycle of the oscillating blood flow signal as the raw Y axis signal stream progresses through the filter window. A fourth waveform traces the residue along the Y-axis following Savitzky-Golay smoothing (chiefly the S1 and S2 sounds). Put another way, FIG. 16 concurrently shows raw Z-axis sensor signal, raw Y-axis sensor signal, a Savitzky-Golay smoothed signal along Y-axis (interpreted as blood flow), and a signal residue along the Y-axis after removal of blood flow component.

Figure 29:
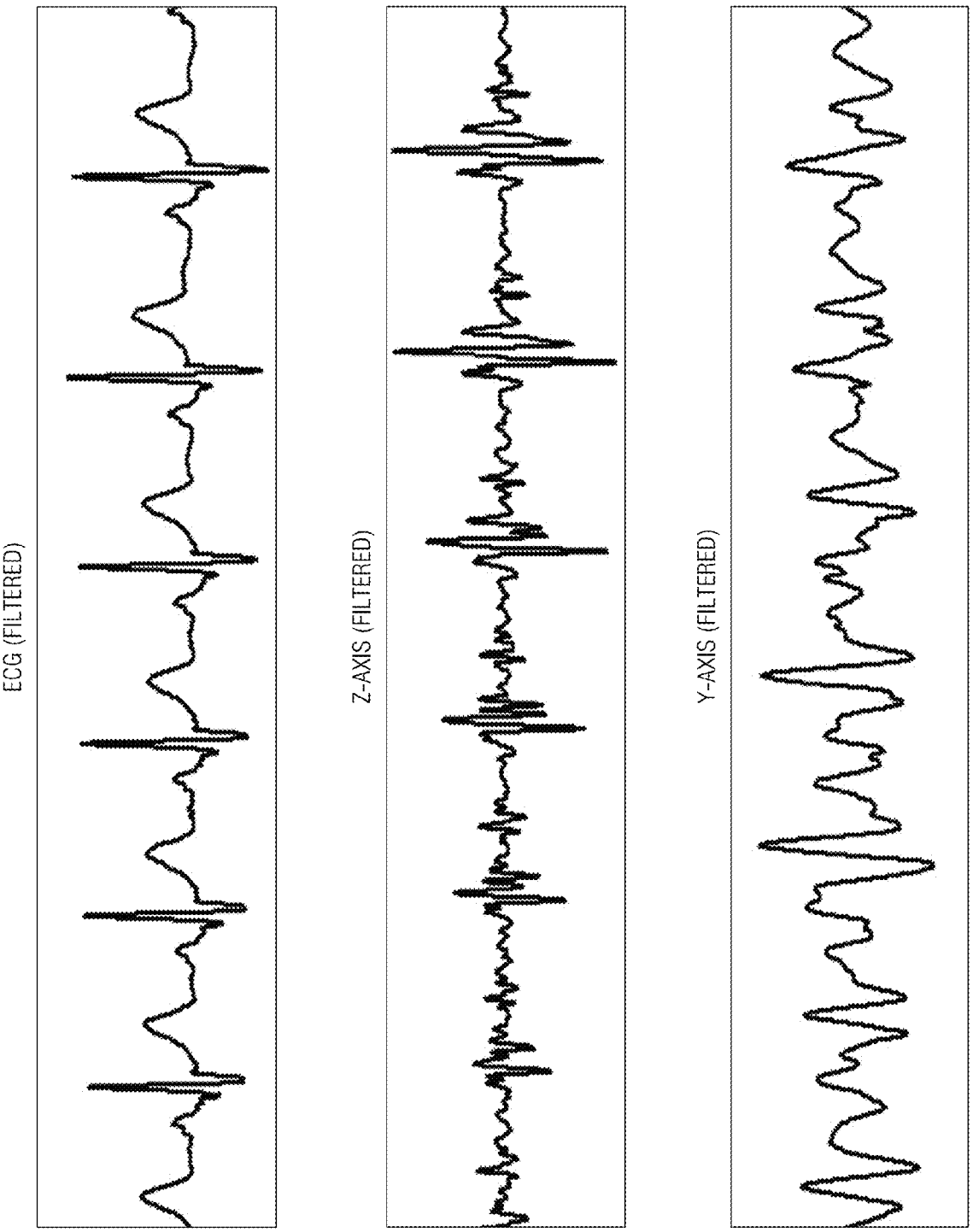
FIG. 29 is a voltage-versus-time graph of three concurrent waveforms including a pair of inventively filtered accelerometer-based waveforms from Z- and Y-axes of the single chest sensor in the inventive structures and processes of FIGS. 26, 30 and 31, compared with a reference ECG waveform.

In FIG. 29, a first waveform traces the ECG signal. A second waveform shows heart sounds derived from the Z axis accelerometer signal as the residue of polynomial filtering of FIG. 31 (left side). A third waveform traces the extracted flow signal from S-G filtering of the accelerometer Y-axis sensor signal of FIG. 31 (right side). In this third waveform, a primary "flow" peak (between S1 and S2) from the accelerometer-based waveform is prominent on the third waveform in FIG. 29 and bears some relationship to a signal from a ballistocardiogram (BCG) while not being identical to a BCG. This third waveform is called a flow signal and appears to be related to some extent with the acceleration of surge blood as it is pushed out of the heart's left ventricle into the aorta. The flow signal obtained from the accelerometer Y-axis has noticeable ringy-ness to it, and the additional features of the flow signal of the S-G filtered Y-axis accelerometer sensor can convey some useful information about heart and valve mechanics and possibly other subjects, as described further elsewhere herein. Such information is suitably generated and communicated electronically in the wired or wireless apparatus of FIGS. 24, 25 and 26 operating according to processes described in FIG. 31 and FIG. 36A, and/or in FIG. 36B.

Detection of Isovolumic Contraction Interval IVCI (FIG. 32) is provided in some embodiments by electronically measuring the time interval between the closure of the mitral and tricuspid valve (S1 waveform on the Z-axis signal) and the start of blood flow (measured by the first major inflection point on the Y-axis flow signal after S1) to output a measure signal representing the IVCI of the ventricle.

Detection of Pre-ejection Period PEP and Contractility VC involves the QRS waveform of the reference ECG (FIGS. 2, 29, 32) that signifies the instant of ventricular depolarization. PEP is provided in some embodiments by electronically measuring the time interval between the peak in the QRS wave and the start of blood flow to output a measure signal signifying PEP. The electronic measurement jointly processes 1) the flow signal from filtering the accelerometer-derived Y-axis (FIGS. 26, 28-31), and 2) the simultaneous ECG as shown in FIG. 2.

In FIG. 31, a process embodiment is represented physically in system storage unit or memory of FIG. 25 and executed on the signal processing unit of FIG. 25 or digital signal processor DSP of FIG. 26. In FIG. 31 (left side), Z-axis signal processing 110-170 generally is analogous to the Z-axis processing of FIG. 4, and additionally the peak detection 170 of the S1 pulse is followed in FIG. 31 by a time determination 780 of a first peak location in time P1 of the first heart sound peak S1 in each heart beat. Counter operation in response to the S1 pulses (and S2 pulses or both) electronically generates a heart rate signal as in FIG. 36.

Figure 32:
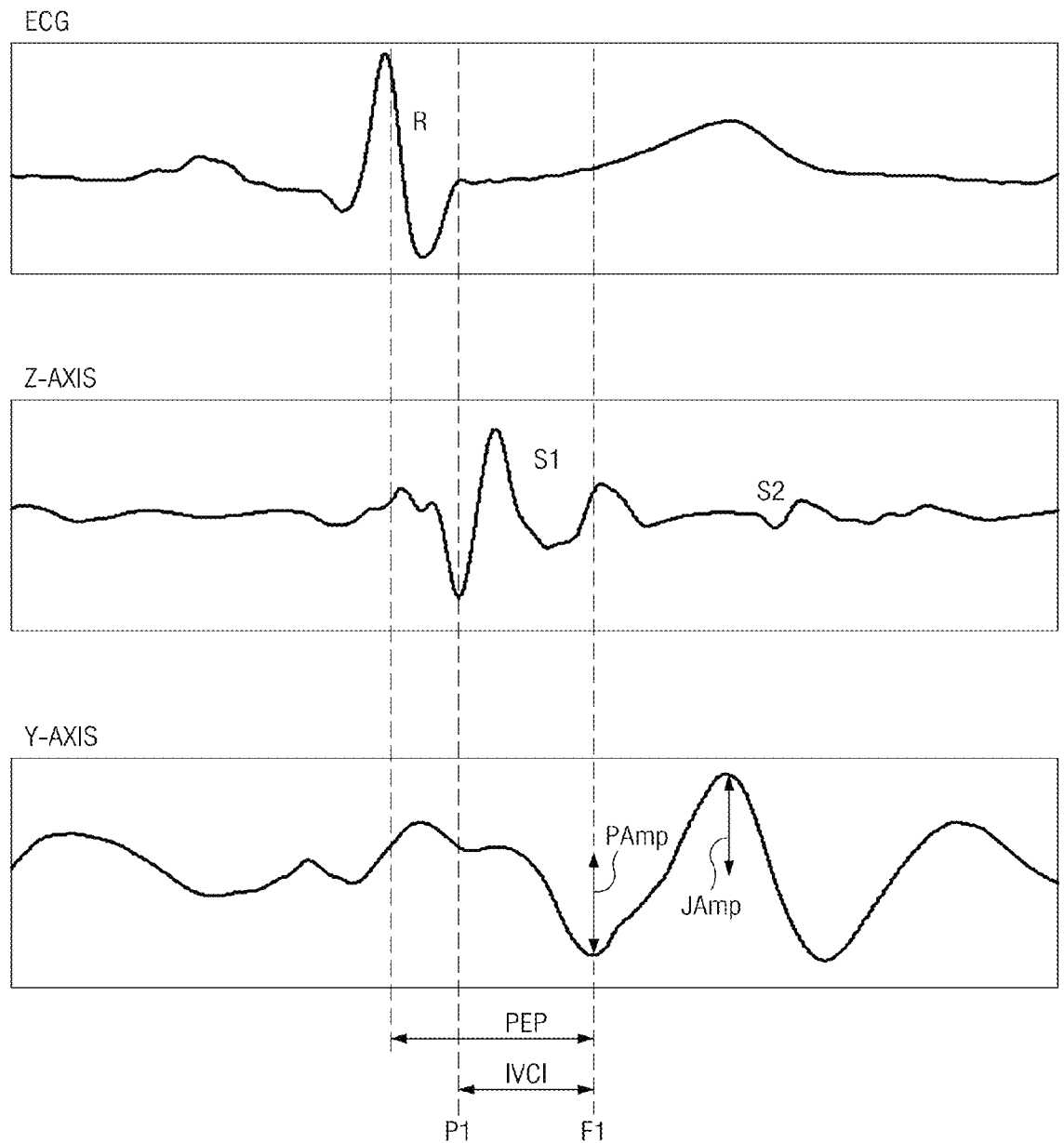
FIG. 32 is a voltage-versus-time graph of three concurrent waveforms including an ECG signal, a filtered heart signal from the Z-axis accelerometer sensor, and a blood flow signal filtered from Y-axis of the accelerometer sensor in the inventive structures and processes of FIGS. 26, 30 and 31, and further showing time locations P1 and F1 and hemodynamic parameters for isovolumic contraction interval IVCI, pre-ejection period PEP and flow peak amplitudes PAmp and Jamp.

In FIG. 31 (right), Y-axis signal processing at step 710 low pass filters (LPFs) the Y-axis input (filter cutoff 50 Hz) and then a step 730 S-G polynomial-filters (or otherwise filters effectively) the LPF signal from step 710 to produce a flow signal output from step 730. A step 770 performs electronic peak (and trough) detection on the flow signal to identify a flow peak amplitude PAmp. A succeeding step 785 identifies the location F1 of that peak in time, as illustrated graphically in FIG. 32. Then, in FIG. 31, both the heart rate signal output HR and first peak location in time P1 from step 780 are combined with and/or compared with first flow signal peak time location F1 from step 785 for each heartbeat. The time difference of F1-P1 represents or is proportional to the isovolumic contraction interval IVCI. IVCI in FIGS. 31 and 32 is estimated, for example, as the time difference between time P1 of the peak of the S1 waveform (derived from the residue signal based on the Z-axis sensor) and the time F1 of the first peak of the flow signal derived from the Y-axis sensor. (Some embodiments determine heart sound time P1 based on Y-axis processing instead of Z-axis processing.)

In FIG. 31, Stroke volume SV and relative changes therein are computed at a step 790 proportional to the peak amplitude PAmp of the flow signal derived by filtering from the Y-axis accelerometer sensor. SV in some embodiments is computed proportional to the peak amplitude PAmp of the flow signal multiplied by the ICVI estimate. Cardiac output CO in FIG. 31 is electronically generated by multiplying stroke volume SV by heart rate HR derived from Z-axis processing from the step 140 residue from accelerometer sensor filtering and the result is supplied to display 550.i or 650.i and other devices as discussed in connection with FIG. 25 and other system Figures. In FIG. 31, hemodynamic parameters including all of IVCI, SV, CO, PEP, and VC and others are obtained.

FIG. 32 depicts an ECG, heart sound signal, and flow signal from the accelerometer 610. The time P1 of occurrence of the S1 sound and the peak location in time F1 of the flow signal in FIG. 32 are used to provide a time difference for electronically estimating isovolumic contraction interval ICVI. Pre-ejection period PEP is electronically derived using the time difference between the peak of ECG signal and peak F1 of the flow signal. A peak amplitude of the flow signal is signified by PAmp in FIG. 32. Peak amplitude PAmp is electronically derived as the difference between the highest peak of the flow signal during a given heartbeat and a baseline average of the flow signal as indicated by a medial dotted line for that heartbeat. A succeeding peak Jamp is also depicted. An electronic process embodiment generates signals representing a value of PEP for every heartbeat and a value of PAmp for every heartbeat.

Figure 33:
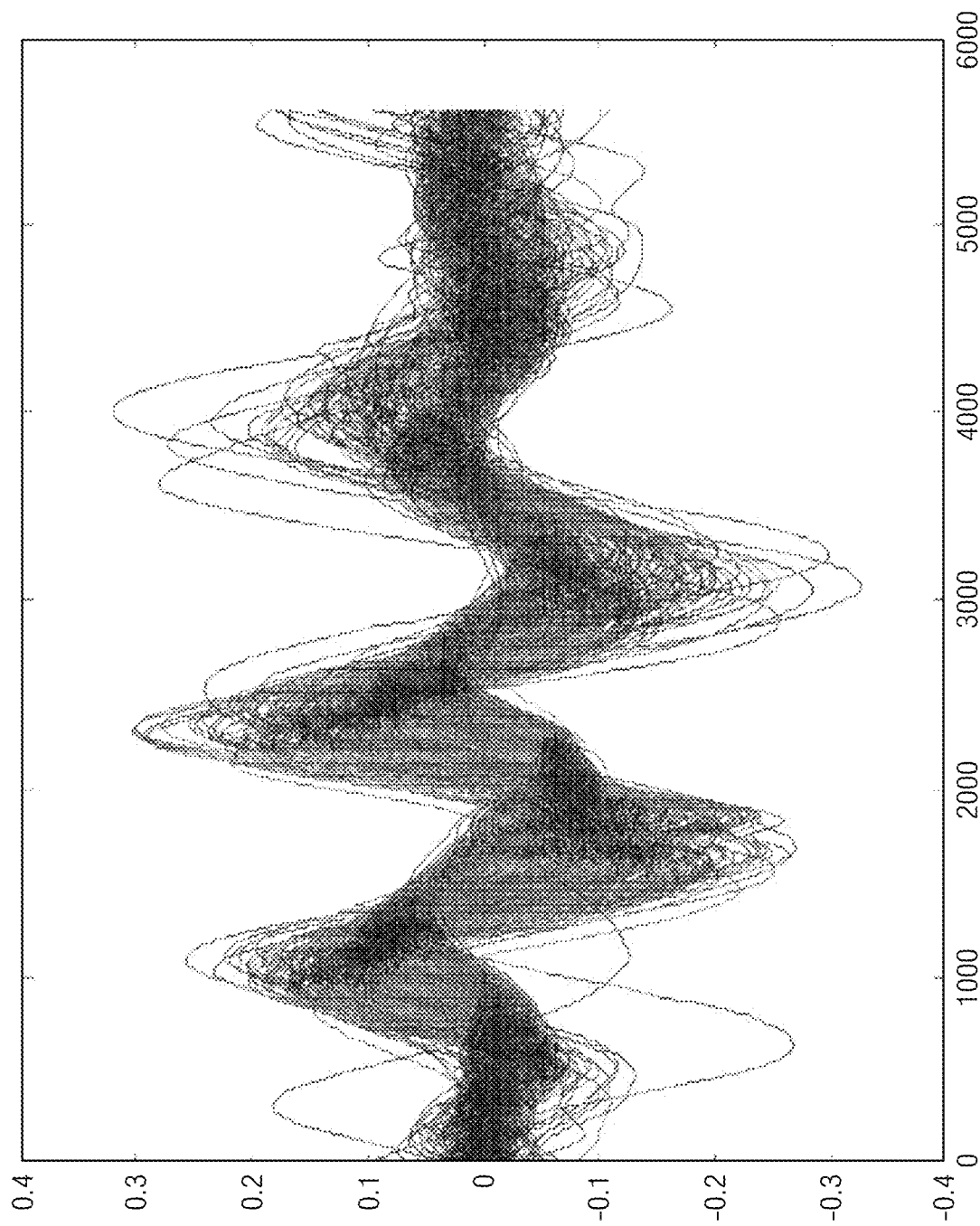
FIG. 33 is a graph of voltage (arbitrary units) versus time-samples for a multitude (ensemble) of waveforms each of a respective instance of inventively filtered blood flow signal from Y-axis of the accelerometer sensor in the inventive structures and processes of FIGS. 26 and 30.

FIG. 33 shows superimposed flow signal ensembles for individual heart beats aligned to the ECG R-waves. The superimposed ensembles show relative changes (up to 2×) in signal amplitude and timing (jitter/dilation) during recovery of subject from mild exercise. The multiple ensembles or heart-beat intervals from the same signal acquired during exercise recovery are superimposed after aligning to ECG R-wave. They show the amplitude and timing jitter in this Y-axis signal that is interpreted as blood flow. Amplitude jitter shows that the initial flow is almost twice stronger shortly after exercise and the intensity of blood flow decreased as the subject recovered over time. Also, the timing jitter shows that the initial flow peak is closer to the ECG R-wave (shorter pre-ejection period) corresponding to a more contractile state of the heart. Some embodiments also generate a signal representing the variance of the jitter in either or both of ICVI and PEP during a period of exercise and/or during a period of rest, as well as changes in such variance value, as an indication of heart function and changes therein.

Figure 40A:
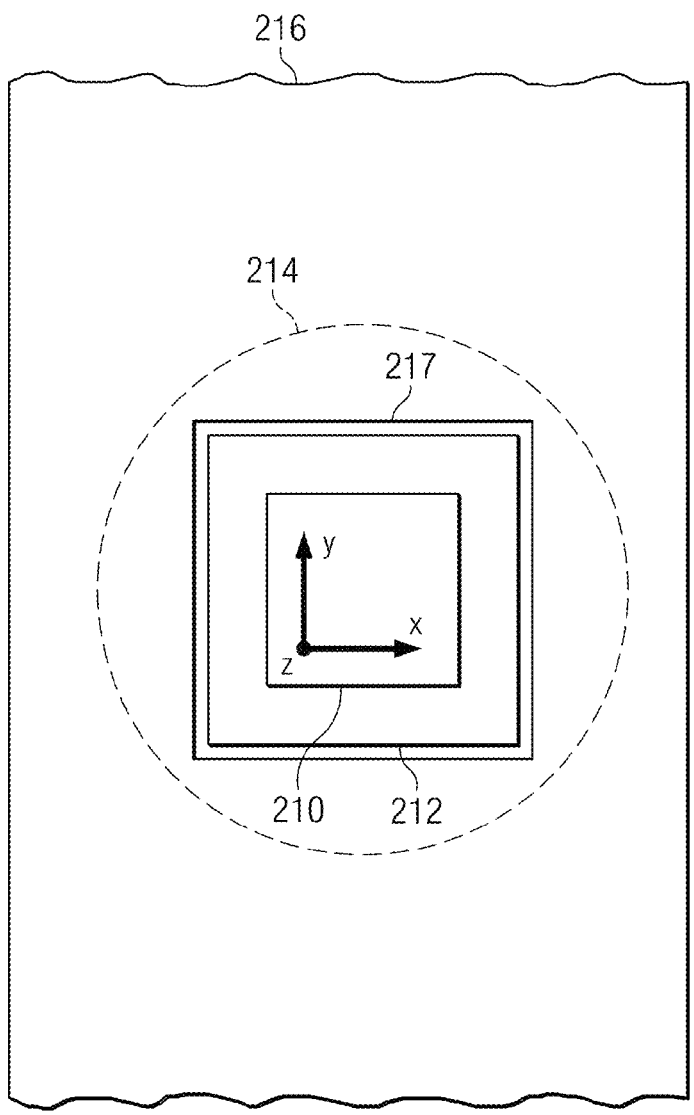
FIGS. 40A and 40B are respective broadside and cross-sectional views of an inventive accelerometer sensor and transponder chip mounted on a support plate affixed by an adhesive tape to the chest, and for use with the inventive structures and processes from the other Figures.
Figure 40B:
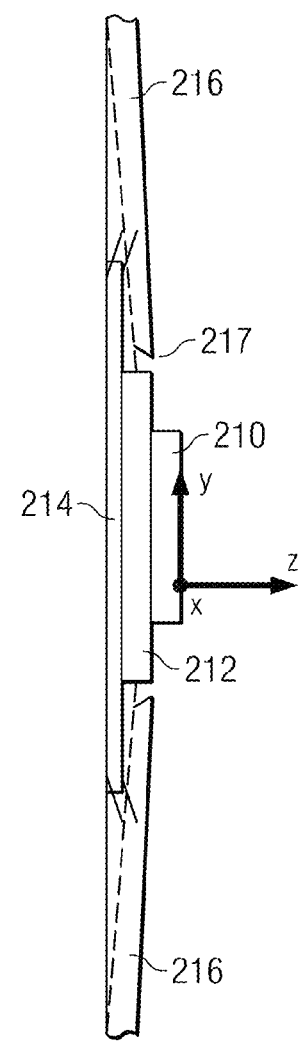

In some embodiments that measure Pre-ejection period PEP and contractility VC, one of the ECG electrodes of FIG. 2 is physically combined or associated with the accelerometer sensor of FIG. 2, FIG. 26, and/or FIGS. 40A, 40B. Affixing both the electrically-separate ECG sensor and accelerometer as one physical unit simultaneously to the chest affords additional convenience. Another ECG electrode of FIG. 2 in some embodiments has a flexible lead across the chest or along the body that physically joins to an operational amplifier chip of FIG. 2 in the same physical unit as the accelerometer to detect and amplify a potential difference between the two ECG electrodes.

Because of the micro-miniaturization of integrated circuits, the physical sensor unit is very light in weight and readily taped to the chest. Some further embodiments also include a miniature microphone along with the accelerometer in the same chest-worn physical unit for obtaining heart sound audio for parallel processing. Various embodiments recognize a multitude of concurrent signals that can be obtained by a single chest accelerometer and provide rich processing to separate them while managing to get physiologically relevant information from the multitude of signals. Some of these signals are: Heart-rate, Activity/Motion, Respiration and intrapleural or intra-thoracic pressure changes, Hemodynamics (timings and amplitudes and changes), Cough, sneeze, snore, speech, breathing sounds, and all other physiological processes, conditions, and parameters to which the teachings herein lend themselves. Coughing, sneezing, snoring, speech-related processes, and breathing sounds are detected in some embodiments by post-processing the accelerometer for acceleration patterns over both single instances and multiple instances to distinguish body motions due to coughing, sneezing, snoring, speech-related processes, and breathing sounds from those of gait and respiration and other activities.

Detecting and separating coughing, sneezing, snoring, speech-related processes, and breathing sounds are suitably also or alternatively provided by filtering of a microphone input and processing to detect a pattern and/or also processing the accelerometer in parallel to other processes described herein and at higher frequencies. In this way, nuanced analysis of cardiovascular, pulmonary, respiratory and other conditions is conveniently facilitated by the data representing the perspectives that ECG potential difference(s), chest-derived audio, and accelerometer sensor respectively support.

Some embodiments may be called upon to estimate Pre-ejection period PEP and contractility VC or trends therein, but lack the ECG electrodes of FIG. 2 and have only the accelerometer sensor. This may be the case in remote monitoring when a person is at a residence and away from the clinic. IVCI can be measured using the accelerometer sensor 610 as the only data source in some embodiments based on S1-to-F1 interval in FIG. 32. Then, recognizing a possibly temporary and not necessarily certain relationship or correlation of PEP and IVCI, the IVCI is guardedly either used as a proxy directly or for trends for Pre-ejection period PEP (and for use in obtaining contractility VC) where measurements indicate that it is sufficiently-correlated to PEP or trend therein, or at least sufficient for monitoring variations in PEP and VC to detect excursion conditions (departures from expected parameter ranges) indicative of advisability of a subsequent clinic visit. Also, previous clinical measurements on the patient with both accelerometer and ECG may be used to calibrate a time interval adjustment value $\alpha$ and scale value $\beta$ to estimate PEP from IVCI according to Equation (15), where measurements indicate that adjustment $\alpha$ and scale value $\beta$ are statistically significant and sufficiently accurate. That adjustment $\alpha$ and scale value $\beta$ are suitably additionally clinically measured for the patient as a function of heart rate and any other relevant parameter and, if similarly satisfactory, then further downloaded as a table of values $\alpha(HR, etc.)$ and $\beta(HR, etc.)$ representing a calibration adjustment to estimate PEP from IVCI adjusted by such tabulated function $\alpha(HR, etc.)$ and $\beta(HR, etc.)$ of heart rate HR, etc. That mechanism of estimating PEP from IVCI involves training a mapping function for each subject, recognizing that such approach is likely to be acceptable only when the subject thereafter is to be remote from the clinic and no other alternative will be immediately available at the remote location.

$$PEP=\beta*IVCI+\alpha \quad (15)$$

The table of values or parameter table for such functions $\alpha$(HR, etc.) and $\beta$(HR, etc.) is downloaded into flash memory for use by the signal processor that processes the accelerometer sensor signal. In that way, PEP estimates and VC estimates are obtained without an ECG and associated ECG electrodes when the patient is remote from the clinic subsequently.

Figure 34:
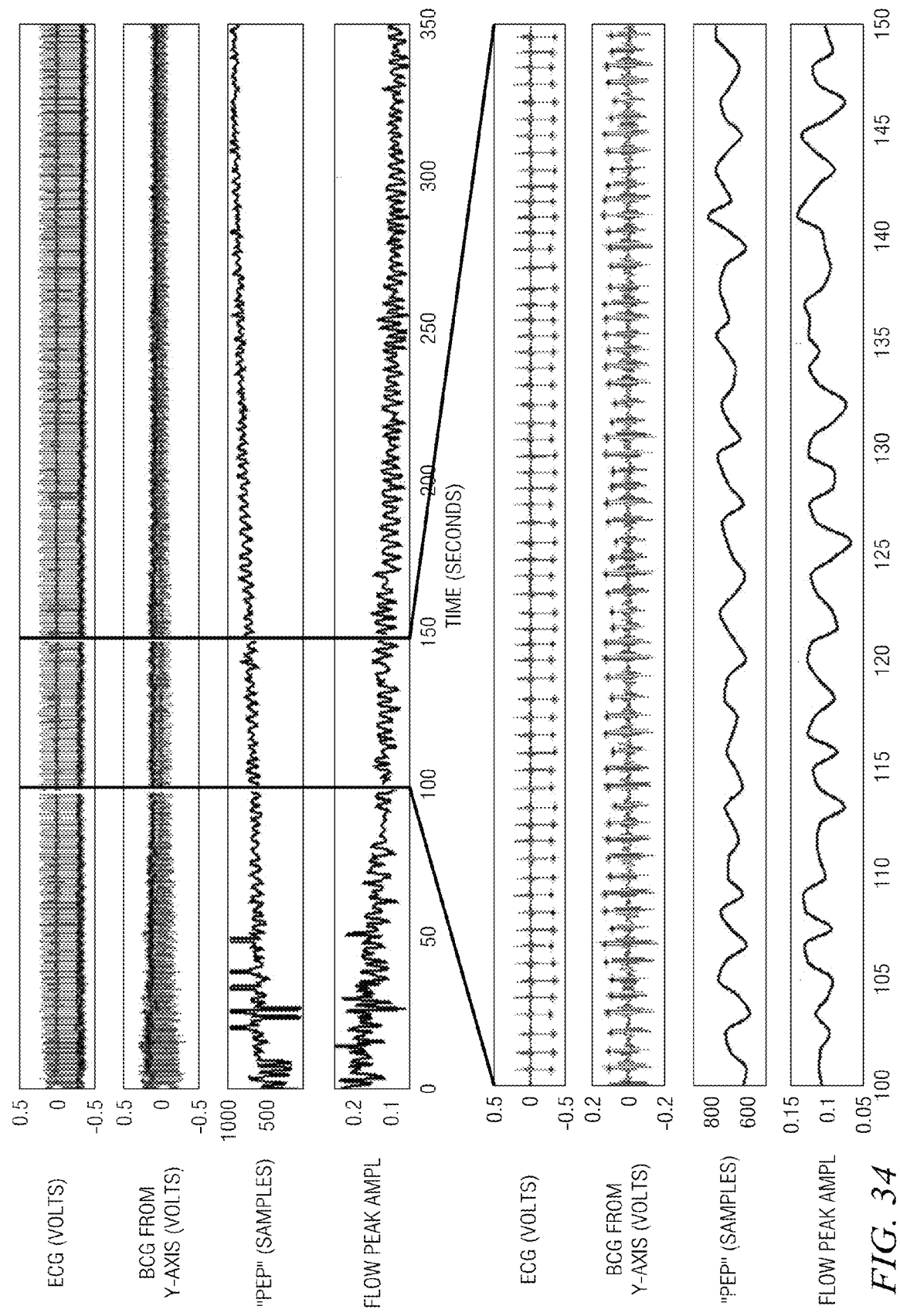
FIG. 34 is a voltage-versus-time graph of four concurrent waveforms during exercise recovery, the waveforms including reference ECG, inventively filtered blood flow signal from Y-axis, PEP, and PAmp. A time interval portion of the traces is magnified and shown as four time-magnified waveforms maintaining the same voltage scale for each except for modest voltage scale magnification for PEP and PAmp.

FIG. 34 shows the modulation of blood flow parameters—Pre-ejection period PEP (and therefore contractility VC) and flow amplitude PAmp—with exercise recovery. The data is collected for 350 seconds while a subject recovers from exercise. A first waveform traces the ECG signal. A second waveform traces the extracted flow signal from S-G filtering of the accelerometer Y-axis sensor signal. A third waveform shows a PEP signal derived from the first and second waveforms. A fourth waveform shows peak flow signal amplitude PAmp of the flow signal of the second waveform. As can be seen from the third waveform, the PEP increases (the heart becomes less contractile as subject recovers from exercise). Concurrently, the peak flow signal amplitude PAmp, interpreted as peak blood flow, decreases over time as shown in the fourth waveform. Smaller variations are clarified in the zoomed-in view and likely correspond to respiration modulation of the peak blood flow and contractility. In this way, the embodiment produces signals as in FIG. 34 for exercise recovery measurement of Pre-ejection Period PEP and amplitude of peak blood flow PAmp. Moreover, in some embodiments, respiration signals can be separated from either PEP or flow peak amplitude PAmp of FIG. 34.

Some medical diagnostic device embodiments have processing embodiments to detect blood flow using an accelerometer sensor, and hence calculate changes in various parameters such as Stroke Volume, contractility etc, as described herein. Deriving BCG-like flow data from an accelerometer sensor according to embodiments is suitably made part of post-operative recovery monitoring system embodiments, as well as device embodiments for use with an accelerometer for long term, continuous monitoring of a patient's heart. Various embodiments remarkably process input from a single accelerometer sensor and operate display and therapeutic devices on the basis of generated signals from the processing that electronically represent any, some or all of heart rate, body motion, respiration, blood flow and hemodynamic parameter signals.

Figure 35A:
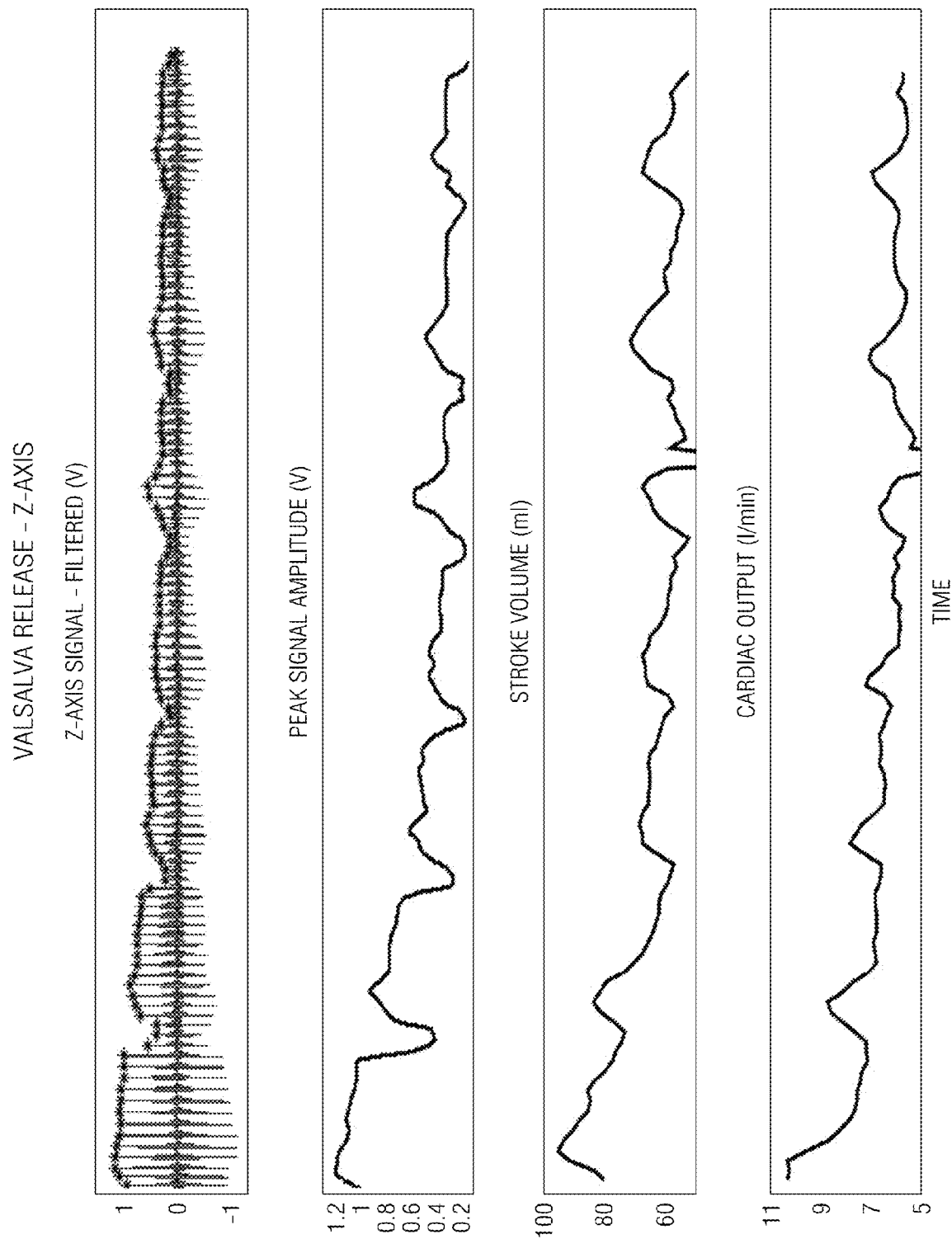
FIG. 35A is a voltage-versus-time graph of four concurrent waveforms over about a minute for a Valsalva Release phase of a Valsalva maneuver; the first waveform representing inventively-produced residue from polynomial filtering the accelerometer Z-axis as in FIG. 31 (left side), the second waveform representing peak amplitude PAmp of that residue, the third waveform representing Stroke Volume, and the fourth waveform representing Cardiac Output.

In FIGS. 35A and 35B, waveforms are depicted during the Valsalva maneuver—wherein the subject sits quietly and blows into a mouthpiece under predetermined back-pressure of the apparatus. By way of background, typical physiological responses expected during the Valsalva maneuver are that aortic pressure rises from a resting value and then falls back to it after a while. Concurrently, heart rate falls below resting rate and then rises above resting rate. Then breath is released after a predetermined time interval. Aortic pressure again rises from approximately the resting value and then falls back to it after a while. Heart rate concurrently falls below the resting rate and then slowly increases to the resting rate.

In FIGS. 35A and 35B, actual waveforms during two different instances of Valsalva Release phase are shown. In FIG. 35A, a first waveform traces the filtered heart signal residue wherein the heart rate is generally increasing, as indicated by decreasing separation between the numerous S1 residue spikes from filtered accelerometer Z-axis as in FIG. 31 (left side). In FIG. 35B, the first waveform traces the blood flow signal (FIG. 31 right side), and the heart rate is generally increasing also, as indicated by decreasing separation between the numerous flow peaks from the flow signal in FIG. 35B. The second waveform of each Figure represents peak amplitude PAmp of the first waveform in each same Figure, which is declining in both instances. The third waveform represents declining Stroke Volume, and the fourth waveform represents declining Cardiac Output. The waveforms appear to be consistent with the physiology of the Valsalva maneuver.

In FIGS. 35A/35B, the SV and CO waveforms ($3^{rd}$, $4^{th}$) were obtained indirectly, using ModelFlow software, responsive to a separate finger-mounted sensor using a continuous blood pressure measurement system manufactured by Finapres Medical Systems. The system is understood to use a non-linear Windkessel model (described elsewhere herein) to model arterial resistance so as to determine blood flow from continuous blood pressure measurements. Notice that the accelerometer-derived peak amplitude ($2^{nd}$ waveform) in both FIGS. 35A and 35B tracks the SV and CO.

Accordingly, some embodiments post-process the peak amplitude PAmp ($2^{nd}$ waveform in FIGS. 35A/35B) on Z-axis or other-axis signal amplitude (which correlates well with SV and CO) to provide or derive time-varying output signals and displays. Such signals and displays an estimation for hemodynamic parameters such as SV and CO and others derivable directly at FIG. 31 step 790 from the amplitude/power of the cardiac S1 pulse either independently of, or in combination with, information from the blood flow signal. The estimation may differ from SV and CO themselves by an additive constant and a scale factor, and this is likely to be acceptable for monitoring applications such as those that begin with a pre-existing physiological state of a subject person and are interested in subsequent variations and/or unusual departures. Notice that the SV and CO hemodynamic parameters vary much more slowly with time t (e.g., less than 0.2 Hz or less than 0.1 Hz or so) than respiratory variation in the peak amplitude signal PAmp(t), so that SV and CO are derived from or filtered out of the peak amplitude signal PAmp(t) in some embodiments and provided for display and recording. Respiration is separated from the peak amplitude signal PAmp(t) as described in FIG. 22 for instance. Respiration, gait and other body motions are detected and separated from each other based on an accelerometer signal as also taught elsewhere herein and also provided for display and recording.

In FIGS. 36A and 36B, a process embodiment is represented physically in system storage unit 630 or memory of FIG. 25 and executed on the signal processing unit 620 of FIG. 25 or digital signal processor DSP of FIG. 26. In FIG. 36A, Z-axis signal processing 110-180 generally is analogous to the Z-axis processing of FIG. 4 and Z-axis processing of FIG. 31 (left side), and outputs heart rate at step 180 and need not be further detailed. In FIG. 36B, Y-axis signal processing 910-940, 970, 980 independently also derives heart rate by obtaining a residue signal from the Y-axis input with the S-G filtered signal subtracted out. Electronic peak detection of the residue signal at step 940 is followed by peak detection 970 and counting 980. The heart rate signal output from step 980 is either combined with and/or compared with the heart rate output of FIG. 36A or used instead of and without the heart rate output of FIG. 36A, depending on embodiment.

Further in FIG. 36B, the S-G filtered signal from step 930 itself is a ringy flow signal of FIGS. 29 and 32 interpreted as blood flow and provided as an electronic output 950 for display 650.i and optional storage 660.i. Also, as described in connection with FIGS. 37 and 38, that flow signal 950 is further processed at a step 960 to recover a Forcing Function F(t) as a further electronic output indicative of cardiac function. In addition, that flow signal is processed at a step 965 to estimate one, two, or all of a triplet of $2^{nd}$ order model parameters for mass m, dashpot ρ (rho), spring γ (gamma) that are delivered as still further electronic outputs. FIG. 31 steps 770, 785 and 790 are suitably also included in FIG. 36B using the flow signal from step 930. Any or all of the outputs can be still further post-processed into electronically-represented interpretations and displays in FIG. 25 of the internals of the chest and heart and states of function.

Figure 37:
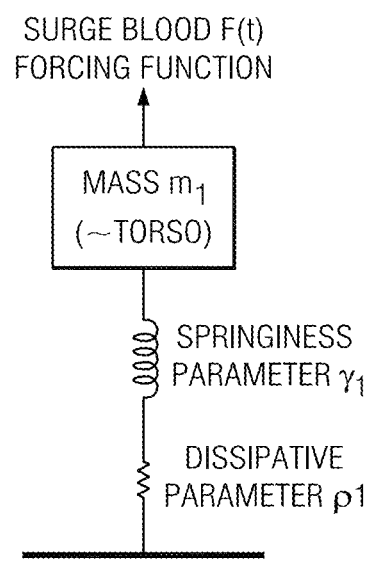
FIG. 37 is a model of a standing subject, the model described by a second-order differential equation to approximate the blood flow signal of the standing subject as a solution thereof.
Figure 38:
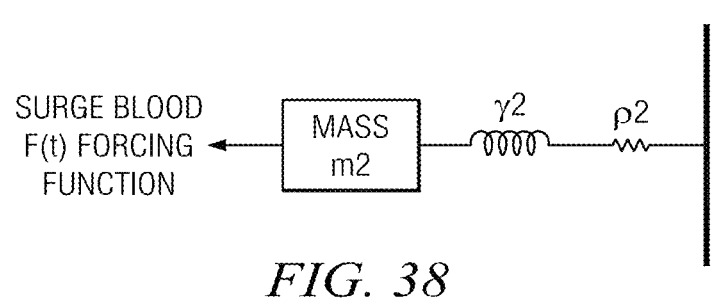
FIG. 38 is a model of a subject lying prone, the model described by a second-order differential equation having different model parameters than in FIG. 37, to approximate the blood flow signal of the prone subject as a solution thereof.

In FIGS. 37 and 38, post-processing is applied to the damped oscillatory flow signal at 950 of FIG. 36B (derived from the Y-axis accelerometer sensor) as from a 2nd order system model. That $2^{nd}$ order system model has a forcing function F(t) (newtons) and constant coefficient parameters for mass m, dashpot ρ (rho), spring γ (gamma) in its 2nd order linear differential equation of Equation (16). The variable y represents physical displacement of the chest sensor from an average y position (conceptually measured from some stationary point of reference on the body, such as the hips, relative to which the chest is displaced).

$$m\partial^2 y/\partial t^2 + \rho \partial y/\partial t + \gamma y(t) = F(t) \qquad (16)$$

FIG. 37 models a standing individual with a first triplet of those parameters subscripted "1." FIG. 38 models the individual lying prone, with a second triplet of values for those parameters subscripted "2." In both cases the accelerometer Y-axis sensor is used, where in FIG. 37 that sensor is vertical, and in FIG. 38 that sensor is horizontal. In both the standing and prone positions that sensor is positioned the same on the chest, parallel to a superior-inferior axis of symmetry of the body from head to feet.

Note that the flow signal 950, g(i) derived by step 930 from the Y-axis accelerometer sensor (e.g. by S-G filtering), can be regarded as a series of samples g(t) each substantially proportional to the second derivative $\partial^2 x/\partial t^2$ itself in Equation (16). The dashpot parameter ρ introduces energy dissipation, and the time constant τ of decay of the damped oscillatory signal is related to the ratio m/ρ, meaning the mass parameter m (kilograms) divided by the dashpot parameter ρ (newtons/(meters/sec)).

$$\tau = m/\rho \qquad (17)$$

The frequency $f_s$ of the damped oscillatory signal is related to $(1/2\pi)\sqrt{(\gamma/m)}$, i.e., the square root of the ratio of the spring parameter γ (newtons/meter) divided by the mass parameter m (kilograms), and that square-root result divided by 2π.

$$f_s = (1/2\pi)\sqrt{(\gamma/m)} \qquad (18)$$

The post-processing suitably estimates F(t)/m, such as by numerical integrations directly from the damped oscillatory flow signal waveform from the y-axis of the accelerometer, $S(t)=\partial^2 y/\partial t^2$ using Equation (16) written in the form of Equation (19). The numerical integration begins as each spindle-shaped accelerometer Y-axis waveform commences in FIG. 29 (3rd waveform) for a given heartbeat, and assumes that any constants of integration are zero (i.e., zero position, zero velocity. For applications based on the shape or morphology of the forcing function F(t), the mass m is merely a constant of proportionality that does not affect the shape. If mass is important to the application, the mass is taken as that of the head and torso such as some fraction (e.g., 0.6) of the body mass in kilograms. The time constant τ is numerically estimated as the length of time from the peak of the spindle-shaped acceleration waveform to the time when the waveform is about ⅔ dissipated (i.e., reduced on later end of the spindle to 1/e of its earlier peak amplitude, where e is base of natural logarithms 2.71828 . . . ). In FIG. 29, the time constant is about a quarter of a second. The frequency $f_s$ is numerically estimated as the number of cycles in some portion of the spindle-shaped acceleration waveform divided by the time in seconds occupied by that portion. In FIG. 29, the frequency $f_s$ is about 8 Hertz.

$$F(t)/m = S(t) + (1/T)\int_0^t S(t)dt + (2\pi f_s)^2 \int_0^t \int_0^t S(t)dt \qquad (19)$$

Alternatively, the post-processing uses any applicable statistical time-series analysis package or procedure to recover best statistical estimates for the forcing function and the $2^{nd}$ order constant coefficient parameters.

The forcing function $F_Y(t)$ component parallel to the Y-axis sensor may arise from a mixture of 1) physical acceleration of the heart itself upon ventricular contraction and 2) the acceleration of blood surging into the aorta when the blood is expelled from the left ventricle. The parameter γ for spring-constant and parameter ρ for dashpot seem to relate to some gross average of mechanical properties of the interiors of chest and abdomen. The mass parameter m probably is related or proportional to the mass of the torso and perhaps the head, but probably not to the mass of the legs because the legs are probably not accelerated in the Y-axis direction. The observed S1-S1 waveform also has a rising amplitude of oscillation immediately preceding the damped oscillation, see FIG. 32. The latter behavior can be due to entry of blood from the venae cavae into the right atrium, and the right ventricular contraction into the pulmonary artery. Accordingly, embodiments for extraction and analysis of forcing function $F_Y(t)$ can provide useful and more nearly comprehensive information on cardiac and pulmonary function as well as hemodynamic information.

Some embodiments are contemplated that monitor accelerometer X-axis sensor information as well as the Y-axis and Z-axis. By X-axis sensor is meant a sensor oriented to sense acceleration laterally across the chest. A transverse displacement variable x for purposes of Equation (20-X) represents side-to-side physical displacement of the chest sensor from an average x position (or conceptually also from a point of reference such as the center of mass of the heart relative to which the chest is displaced.) In such an embodiment, signal from the X-axis sensor is filtered in parallel with the filtering of the Y-axis signal, and in a manner for the X-axis analogous to the filtering described hereinabove for the Y-axis signal. Because of the assymetrical location and slantwise inclination and of the heart in the chest, the filtered signal from the X-axis sensor provides further information about a lateral (side-to-side) component $F_X(t)$ of the forcing function F(t) considered as a vector. Taken together, these two forcing function components $F_Y(t)$ and $F_X(t)$ can provide further useful information on cardiac function, pulmonary function, properties of the pleura, pleural cavity, and pericardium, as well as hemodynamics information relating to the aorta, venae cavae, and pulmonary arteries and pulmonary veins by any suitable process now known or hereafter devised. The parameter triplets are respectively subscripted "1Y" and "1X" to designate a standing position ("1") and the Y-axis or X-axis sensor involved. If the prone position is involved then the subscript "1" is changed to "2."

$$m_{1Y}\partial^2 y/\partial t^2 + \rho_{1Y}\partial y/\partial t + \gamma_{1Y}y(t) = F_{1Y}(t) \quad (20\text{-}Y)$$

$$m_{1X}\partial^2 x/\partial t^2 + \rho^{1x}\partial x/\partial t + \gamma^{1X}x(t) = F_{1X}(t). \quad (20\text{-}X)$$

Figure 39:
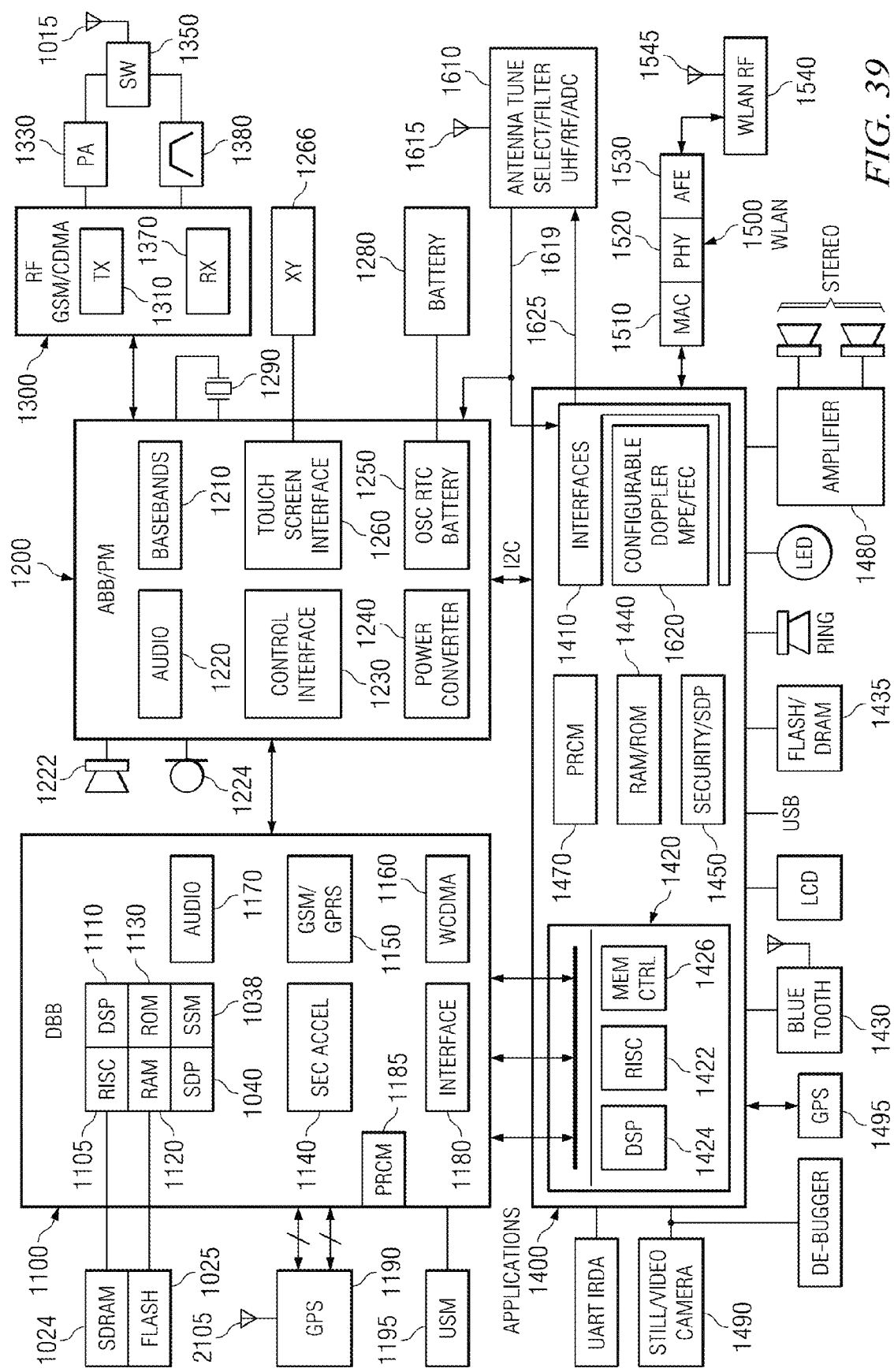
FIG. 39 is a block diagram of a system structure for use in and improved according to inventive structures and processes from the other Figures.

In FIG. 39, an embodiment is improved as in the other Figures herein and used as one or more replicas as discussed in connection with FIG. 25. FIG. 39 illustrates inventive integrated circuit chips including chips 1100, 1200, 1300, 1400, 1500, and GPS 1190 (1495) for use in any one, some or all of the blocks of the communications system 600 of FIG. 25. The skilled worker uses and adapts the integrated circuits to the particular parts of the communications system 600 as appropriate to the functions intended. It is contemplated that the skilled worker uses each of the integrated circuits shown in FIG. 39, or such selection from the complement of blocks therein provided into appropriate other integrated circuit chips, or provided into one single integrated circuit chip, in a manner optimally combined or partitioned between the chips, to the extent needed by any of the applications supported such as voice WLAN gateway, cellular telephones, televisions, internet audio/video devices, routers, pagers, personal digital assistants (PDA), microcontrollers coupled to controlled mechanisms for fixed, mobile, personal, robotic and/or automotive use, combinations thereof, and other application products now known or hereafter devised for increased, partitioned or selectively determinable advantages.

In FIG. 39, an integrated circuit 1100 includes a digital baseband (DBB) block that has a RISC processor 1105 (such as MIPS core(s), ARM core(s), or other suitable processor) and a digital signal processor 1110 such as from the TMS320C55x™ DSP generation from Texas Instruments Incorporated or other digital signal processor (or DSP core) 1110, communications software and security software for any such processor or core, security accelerators 1140, and a memory controller. Security accelerators 1140 provide additional computing power such as for hashing and encryption that are accessible, for instance, when the integrated circuit 1100 is operated in a security level enabling the security accelerators block 1140 and affording types of access to the security accelerators depending on the security level and/or security mode. The memory controller interfaces the RISC core 1105 and the DSP core 1110 to Flash memory 1025 and SDRAM 1024 (synchronous dynamic random access memory). On chip RAM 1120 and on-chip ROM 1130 also are accessible to the processors 1105 and 1110 for providing sequences of software instructions and data thereto. A security logic circuit 1038 of FIGS. 16 and 17 has a secure state machine (SSM) to provide hardware monitoring of any tampering with security features. A Secure Demand Paging (SDP) circuit 1040 is provided for effectively-extended secure memory.

Digital circuitry 1150 on integrated circuit 1100 supports and provides wireless modem interfaces for any one or more of GSM, GPRS, EDGE, UMTS, and OFDMA/MIMO (Global System for Mobile communications, General Packet Radio Service, Enhanced Data Rates for Global Evolution, Universal Mobile Telecommunications System, Orthogonal Frequency Division Multiple Access and Multiple Input Multiple Output Antennas) wireless, with or without high speed digital data service, via an analog baseband chip 1200 and GSM/CDMA transmit/receive chip 1300. Digital circuitry 1150 includes a ciphering processor CRYPT for GSM ciphering and/or other encryption/decryption purposes. Blocks TPU (Time Processing Unit real-time sequencer), TSP (Time Serial Port), GEA (GPRS Encryption Algorithm block for ciphering at LLC logical link layer), RIF (Radio Interface), and SPI (Serial Port Interface) are included in digital circuitry 1150.

Digital circuitry 1160 provides codec for CDMA (Code Division Multiple Access), CDMA2000, and/or WCDMA (wideband CDMA or UMTS) wireless suitably with HSDPA/HSUPA (High Speed Downlink Packet Access, High Speed Uplink Packet Access) (or 1xEV-DV, 1xEV-DO or 3xEV-DV) data feature via the analog baseband chip 1200 and RF GSM/CDMA chip 1300. Digital circuitry 1160 includes blocks MRC (maximal ratio combiner for multipath symbol combining), ENC (encryption/decryption), RX (downlink receive channel decoding, de-interleaving, viterbi decoding and turbo decoding) and TX (uplink transmit convolutional encoding, turbo encoding, interleaving and channelizing.). Blocks for uplink and downlink processes of WCDMA are provided.

Audio/voice block 1170 supports audio and voice functions and interfacing. Speech/voice codec(s) and speech recognition are suitably provided in memory space in audio/voice block 1170 for processing by processor(s) 1110. An applications interface block 1180 couples the digital baseband chip 1100 to an applications processor 1400. Also, a serial interface in block 1180 interfaces from parallel digital buses on chip 1100 to USB (Universal Serial Bus) of PC (personal computer) 2070. The serial interface includes UARTs (universal asynchronous receiver/transmitter circuit) for performing the conversion of data between parallel and serial lines. A power resets and control module PRCM 1185 provides power management circuitry for chip 1100. Chip 1100 is coupled to location-determining circuitry 1190 satellite positioning such as GPS (Global Positioning System) and/or to a network-based positioning (triangulation) system, to an accelerometer, to a tilt sensor, and/or other peripherals to support positioning, position-based applications, user real-time kinematics-based applications, and other such applications. Chip 1100 is also coupled to a USIM (UMTS Subscriber Identity Module) 1195 or other SIM for user insertion of an identifying plastic card, or other storage element, or for sensing biometric information to identify the user and activate features.

In FIG. 39, a mixed-signal integrated circuit 1200 includes an analog baseband (ABB) block 1210 for GSM/GPRS/EDGE/UMTS/HSDPA/HSUPA which includes SPI (Serial Port Interface), digital-to-analog/analog-to-digital conversion DAC/ADC block, and RF (radio frequency) Control pertaining to GSM/GPRS/EDGE/UMTS/HSDPA/HSUPA and coupled to RF (GSM etc.) chip 1300. Block 1210 suitably provides an analogous ABB for CDMA wireless and any associated 1xEV-DV, 1xEV-DO or 3xEV-DV data and/or voice with its respective SPI (Serial Port Interface), digital-to-analog conversion DAC/ADC block, and RF Control pertaining to CDMA and coupled to RF (CDMA) chip 1300.

An audio block 1220 has audio I/O (input/output) circuits to a speaker 1222, a microphone 1224, and headphones (not shown). Audio block 1220 has an analog-to-digital converter (ADC) coupled to an audio/voice codec 1170 and a stereo DAC (digital to analog converter) for a signal path to the baseband block 1210 and with suitable encryption/decryption. A control interface 1230 has a primary host interface (I/F) and a secondary host interface to DBB-related integrated circuit 1100 of FIG. 39 for the respective GSM and CDMA paths. The integrated circuit 1200 is also interfaced to an I2C port of applications processor chip 1400 of FIG. 39. Control interface 1230 is also coupled via circuitry to interfaces in circuits 1250 and the baseband 1210. A power conversion block 1240 includes buck voltage conversion circuitry for DC-to-DC conversion, and low-dropout (LDO) voltage regulators for power management/sleep mode of respective parts of the chip regulated by the LDOs. Power conversion block 1240 provides information to and is responsive to a power control state machine between the power conversion block 1240 and circuits 1250. Power management circuitry PRCM 1185 (1470) is coupled with and controls power conversion block 1240 and interfaces to GPS 1190 (1495) and to power save mode controller 2130 (2290) in systems of FIGS. 1-39 and as described elsewhere herein. Circuits 1250 provide oscillator circuitry for clocking chip 1200. The oscillators have frequencies determined by one or more crystals 1290. Circuits 1250 include a RTC real time clock (time/date functions), general purpose I/O, a vibrator drive (supplement to cell phone ringing features), and a USB On-The-Go (OTG) transceiver. A touch screen interface 1260 is coupled to a touch screen XY 1266 off-chip. Batteries such as a lithium-ion battery 1280 and backup battery and recharger provide power to the system and battery data to circuit 1250 on suitably provided separate lines from the battery pack. When needed, the battery 1280 also receives charging current from a Charge Controller in analog circuit 1250 which includes MADC (Monitoring ADC and analog input multiplexer such as for on-chip charging voltage and current, and battery voltage lines, and off-chip battery voltage, current, temperature) under control of the power control state machine. Battery monitoring is provided by either or both of 1-Wire and/or an interface called HDQ.

In FIG. 39 an RF integrated circuit 1300 includes a GSM/GPRS/EDGE/UMTS/CDMA RF transmitter block 1310 supported by oscillator circuitry with crystal(s) 1290. Transmitter block 1310 is fed by basebands block 1210 of chip 1200. Transmitter block 1310 drives a dual band RF power amplifier (PA) 1330. On-chip voltage regulators maintain appropriate voltage under conditions of varying power usage. Off-chip switchplexer 1350 couples wireless antenna and switch circuitry to both the transmit portion 1310, 1330 and the receive portion next described. Switchplexer 1350 is coupled via band-pass filters 1360 to receiving LNAs (low noise amplifiers) for 850/900 MHz, 1800 MHz, 1900 MHz and other frequency bands as appropriate. Depending on the band in use, the output of LNAs couples to GSM/GPRS/EDGE/UMTS/CDMA demodulator 1370 to produce the I/Q or other outputs thereof (in-phase, quadrature) to the GSM/GPRS/EDGE/UMTS/CDMA basebands block 1210.

Further in FIG. 39, an integrated circuit chip or core 1400 is provided for applications processing and more off-chip peripherals. Chip (or core) 1400 has interface circuit 1410 including a high-speed WLAN 802.11a/b/g interface coupled to a WLAN chip 1500. Further provided on chip 1400 is an applications processing section 1420 which includes a RISC processor 1422 (such as MIPS core(s), ARM core(s), or other suitable processor), a digital signal processor (DSP) 1424 such as from the TMS320C55x™ DSP generation and/or the TMS320C6x™ DSP generation from Texas Instruments Incorporated or other digital signal processor(s), and a shared memory controller MEM CTRL 1426 with DMA (direct memory access), and a 2D (two-dimensional display) graphic accelerator. Speech/voice codec/speech recognition functionality is suitably processed in chip 1400, in chip 1100, or both chips 1400 and 1100.

The RISC processor 1422 and the DSP 1424 in section 1420 have access via an on-chip extended memory interface (EMIF/CF) to off-chip memory resources 1435 including as appropriate, mobile DDR (double data rate) DRAM, and flash memory of any of NAND Flash, NOR Flash, and Compact Flash. On chip 1400, a shared memory controller 1426 in circuitry 1420 interfaces the RISC processor 1420 and the DSP 1424 via an on-chip bus to on-chip memory 1440 with RAM and ROM. A 2D graphic accelerator is coupled to frame buffer internal SRAM (static random access memory) in block 1440. A security block 1450 includes an SSM analogous to SSM 1038 of FIG. 1, and includes secure hardware accelerators having security features and provided for secure demand paging 1040 and for accelerating encryption and decryption. A random number generator RNG is provided in security block 1450.

On-chip peripherals and additional interfaces 1410 include UART data interface and MCSI (Multi-Channel Serial Interface) voice and data wireless interface for an off-chip IEEE 802.15 (Bluetooth and low and high rate piconet, Zigbee, and personal network communications) wireless circuit 1430. The Bluetooth or Zigbee wireless interface is useful for receiving from and controlling the accelerometer sensor and its associated analog circuitry and digital to analog-to-digital converter ADC in FIGS. 1 and 26, among other Figures. In arrangements including ECG electrodes and/or a chest microphone, the analog circuitry at the taped-on sensor unit also includes couplings from such pickup elements to the Bluetooth or Zigbee short distance transceiver from the chest sensor (e.g. FIGS. 40A/40B communicating with a counterpart short distance transceiver at the interface 1410.

Debug messaging and serial interfacing are also available through the UART. A JTAG emulation interface couples to an off-chip emulator Debugger for test and debug. GPS 1190 (1495) is scannable by the debugger, see FIG. 2. Further in peripherals 1410 are an I2C interface to analog baseband ABB chip 1200, and an interface to applications interface 1180 of integrated circuit chip 1100 having digital baseband DBB.

Interface 1410 includes a MCSI voice interface, a UART interface for controls and data to position unit GPS 1495 and otherwise, and a multi-channel buffered serial port (McBSP) for data. Timers, interrupt controller, and RTC (real time clock) circuitry are provided in chip 1400. Further in peripherals 1410 are a MicroWire (u-wire 4 channel serial port) and multi-channel buffered serial port (McBSP) to Audio codec, a touch-screen controller (or coupling to 1260), and audio amplifier 1480 to stereo speakers.

External audio content and touch screen (in/out) 1260, 1266 and LCD (liquid crystal display), organic semiconductor display, and DLP™ digital light processor display from Texas Instruments Incorporated, are suitably provided in various embodiments and coupled to interface 1410. In vehicular use, such as at unit 690 of FIG. 25, the display is suitably any of these types provided in the vehicle, and sound is provided through loudspeakers, headphones or other audio transducers provided in the vehicle. In some vehicles a transparent organic semiconductor display 2095 of FIG. 16 is provided on one or more windows of a vehicle and wirelessly or wireline-coupled to the video feed. Maps and visual position-based interactive imaging and user kinematics applications are provided using double-integrated accelerometer output as discussed elsewhere herein. Also GPS 1190 (1495) and processor 1105, 1110 (1422, 1424) support fixed, portable, mobile, vehicular and other platforms.

Interface 1410 additionally has an on-chip USB OTG interface that couples to off-chip Host and Client devices.

These USB communications are suitably directed outside handset 2010 such as to PC 2070 (personal computer) and/or from PC 2070 to update the handset 2010 or to a camera 1490.

An on-chip UART/IrDA (infrared data) interface in interfaces 1410 couples to off-chip GPS (global positioning system of block 1495 cooperating with or instead of GPS 1190) and Fast IrDA infrared wireless communications device. An interface provides EMT9 and Camera interfacing to one or more off-chip still cameras or video cameras 1490, and/or to a CMOS sensor of radiant energy. Such cameras and other apparatus all have additional processing performed with greater speed and efficiency in the cameras and apparatus and in mobile devices coupled to them with improvements as described herein. Further in FIG. 39, an on-chip LCD controller or DLP™ controller and associated PWL (Pulse-Width Light) block in interfaces 1410 are coupled to a color LCD display or DLP™ display and its LCD light controller off-chip and/or DLP™ digital light processor display.

Further, on-chip interfaces 1410 are respectively provided for off-chip keypad and GPIO (general purpose input/output). On-chip LPG (LED Pulse Generator) and PWT (Pulse-Width Tone) interfaces are respectively provided for off-chip LED and buzzer peripherals. On-chip MMC/SD multimedia and flash interfaces are provided for off-chip MMC Flash card, SD flash card and SDIO peripherals. On chip 1400, a power, resets, and control module PRCM 1470 supervises and controls power consuming blocks and sequences them, and coordinates with PRCM 1185 on chip 1100 and with Power Save Mode Controller 2130 (2290) in GPS 1495 as described elsewhere herein.

In FIG. 39, a WLAN integrated circuit 1500 includes MAC (media access controller) 1510, PHY (physical layer) 1520 and AFE (analog front end) 1530 for use in various WLAN and UMA (Unlicensed Mobile Access) modem applications. In some embodiments, GPS 1495 operates in close coordination with any one, some, or all of WLAN, WiMax, DVB, or other network, to provide positioning, position-based, and user real-time kinematics applications. Still other additional wireless interfaces such as for wideband wireless such as IEEE 802.16 WiMAX mesh networking and other standards are suitably provided and coupled to the applications processor integrated circuit 1400 and other processors in the system. WiMax has MAC and PHY processes and the illustration of blocks 1510 and 1520 for WLAN indicates the relative positions of the MAC and PHY blocks for WiMax.

In FIG. 39, a further digital video integrated circuit 1610 is coupled with a television antenna 1615 (and/or coupling circuitry to share antenna 1015 and/or 1545 and/or 2105) to provide television antenna tuning, antenna selection, filtering, RF input stage for recovering video/audio/controls from television transmitter (e.g., DVB station 2020 of FIG. 16). Digital video integrated circuit 1610 in some embodiments has an integrated analog-to-digital converter ADC on-chip, and in some other embodiments feeds analog to ABB chip 1200 for conversion by an ADC on ABB chip 1200. The ADC supplies a digital output 1619 to interfaces 1410 of applications processor chip 1400 either directly from chip 1610 or indirectly from chip 1610 via the ADC on ABB chip 1200. Controls for chip 1610 are provided on lines 1625 from interfaces 1410. Applications processor chip 1400 includes a digital video block 1620 coupled to interface 1410 and having a configurable adjustable shared-memory telecommunications signal processing chain such as Doppler/MPE-FEC. A processor on chip 1400 such as RISC processor 1422 and/or DSP 1424 configures, supervises and controls the operations of the digital video block 1620.

In combination with the GPS circuit 1190 and/or 1495, and video display 1266 or LCD, the RISC processor 1105/ 1422 and/or DSP 1110 (1424) support location-based embodiments and services of various types, such as roadmaps and directions thereon to a destination, pictorials of nearby commercial establishments, offices, and residences of friends, various family supervision applications, position sending to friends or to emergency E911 service, and other location based services now known or yet to be devised.

Digital signal processor cores suitable for some embodiments in the IVA block and video codec block may include a Texas Instruments TMS32055x™ series digital signal processor with low power dissipation, and/or TMS320C6000 series and/or TMS320C64x™ series VLIW digital signal processor, and have the circuitry and processes of the FIGS. 1-39 coupled with them as taught herein. A camera CAM provides video pickup for a cell phone or other device to send over the internet to another cell phone, personal digital assistant/personal entertainment unit, gateway and/or set top box STB with television TV.

FIGS. 40A and 40B are respective broadside and cross-sectional views of an accelerometer sensor 210 and transmitter, transceiver, or transponder chip 212 firmly mounted on a thin, resilient plastic support plate 214 that can be firmly affixed by an adhesive tape 216 to the chest. The electronics is conveniently light-weight and small and may be quarter-sized, dime-sized or even smaller in size. In FIG. 40A, a dotted outline shows a round smoothed or flanged periphery of plastic support 214 shaped for comfort on the chest.

In FIG. 40B, the Z-axis of accelerometer sensor 210 is perpendicular to the plane defined by plastic support 214 (and to the plane defined by chip 212). The Y-axis and X-axis of sensitivity to acceleration of the accelerometer sensor 210 are perpendicular to each other, with each parallel to the plane defined by a broadside of a package enclosing the accelerometer and likewise parallel to a plane defined by plastic support 214. Adhesive tape 216 adheres to the outward broad side of plastic support 214, thereby holding plastic support 214 firmly against the chest when applied thereto. Adhesive tape 216 has an inner edge 217 defining an approximately square aperture in FIG. 40A that admits the outward-placed transponder chip 212 and accelerometer sensor 210.

An ECG sensor of FIG. 2 and/or a small microphone may also be mounted on plastic support 214 to monitor chest potential and/or chest sounds. The chest-adjacent side of plastic support 214 may also be provided with ECG electrode paste for ECG connectivity with the chest.

In some embodiments, chip 212 harvests power from an interrogation signal from the circuitry of FIG. 39, and in other embodiments a small battery is also provided on plastic support 214 and electrically connected to supply a low power to chip 212. Accelerometer sensor 210 is electrically coupled to transponder chip 212 along with any ECG electrode and microphone elements for wireless communication to the system of FIG. 39. In various embodiments, none, one, some or all of the blocks of FIG. 1 are provided as part of transponder chip 212. Chip 212 in some embodiments includes a very low power processor such as an MSP430™ processor from Texas Instruments Incorporated or other such processor along with the short distance wireless transmitter. Chip 212 can have an antenna such as a spiral antenna fabricated as part of the chip 212, or in some other embodiments an antenna is suitably provided as part of plastic support 214 and electrically connected to chip 212.

Optionally, a plastic cap or header physically encloses and protects the chips over the support 214. Also, in some embodiments, a wireline interface is also provided in chip 212, and the support 214 physically has a miniature wireline female connector attached thereto and electrically connected to the wireline interface in chip 212, such as for USB (Universal Serial Bus). In that way, a clinician may connect a lightweight male connector from a monitoring processor and display unit to the miniature wireline female connector and bypass the short distance wireless function of chip 212 at will. In still other embodiments, the accelerometer 210 and transponder 212 are mounted in a pacemaker that is either implanted in the patient or affixed to the chest.

In FIGS. 40A and 40B, the orientation of the X, Y, and Z axes of the accelerometer sensor on the chest may vary depending on actual placement and actual physical manufacture. Actual orientation of the accelerometer sensor on the chest may vary because of convenience for categories of patients or particular patients or simply due to inadvertent mis-orientation of the sensor. However, physical orientation of the multiple axis accelerometer merely distributes the overall physical acceleration vector a to be sensed to the different sensor axes of the accelerometer according to their vector components in the various axis directions.

Figure 41:
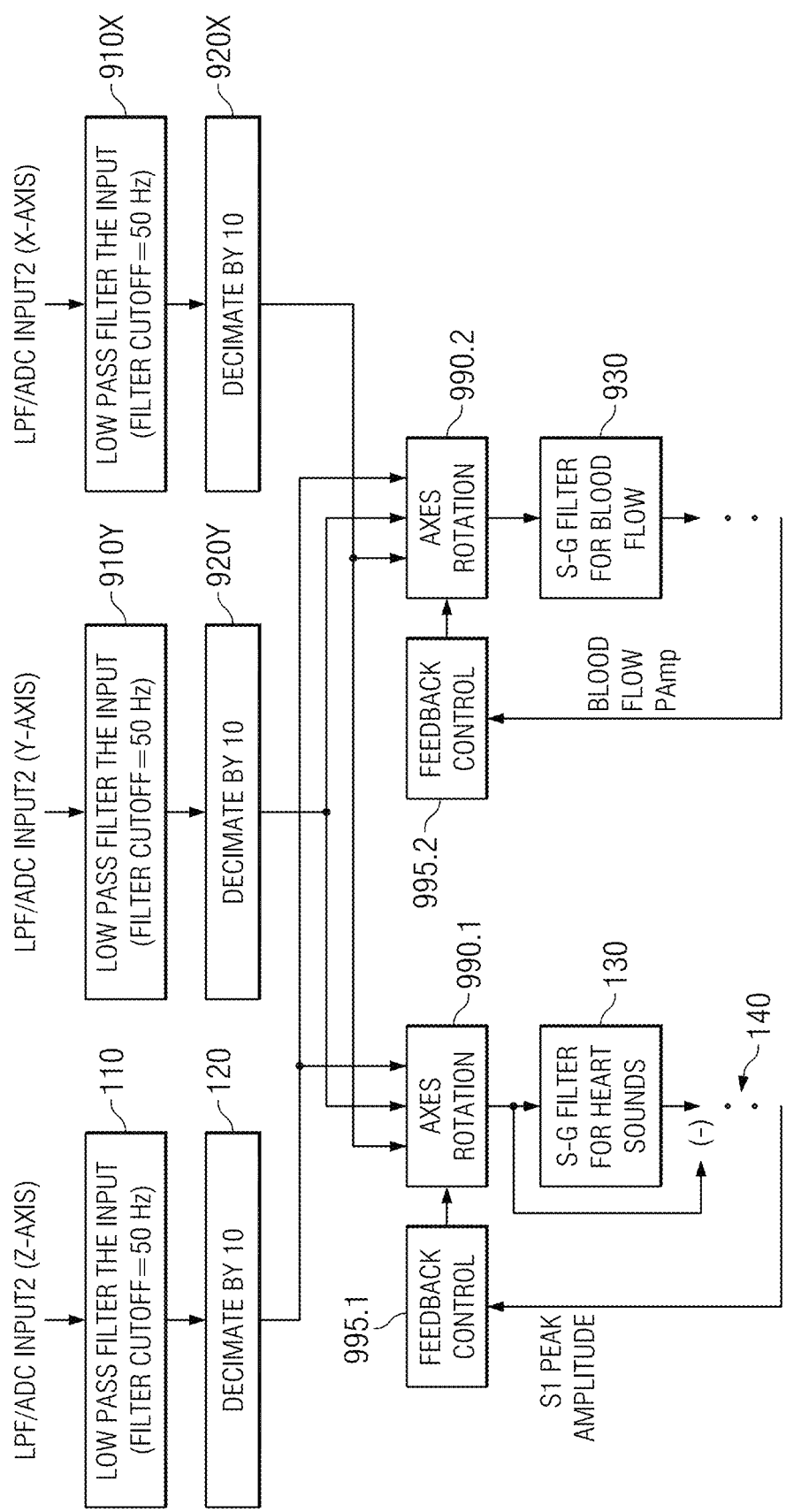
FIG. 41 is a block diagram of an inventive structure and process for variably combining accelerometer signals from multiple axes in various proportions to provide one or more inputs to the smoothing filtering of FIGS. 31, 36A and 36B and various other Figures herein.

Accordingly, some embodiments as in FIG. 41 include an electronic processing module 990.i for virtual re-orientation or optimization of the accelerometer sensor signals by applying a rotation of axes that introduces a multiplication by a rotation matrix to the signals. Such rotation of axes 990.i combines the signals for X, Y, Z accelerometer axes, such as shown for those axes in FIG. 42, according to linear combinations of the signals as if the accelerometer axes were rotated, as shown by Equation (21).

Let an angle θ represent an angle by which the accelerometer Y-axis sensor is to be virtually rotated from its affixed position on the chest to align with the foot-to-head direction on the body or for whatever purpose. Let an angle φ represent an angle by which the accelerometer Z-axis sensor is to be virtually rotated from its affixed position approximately perpendicular to the chest toward that foot-to-head direction on the body. Let a vector V represent the Z-axis signal, the Y-axis signal and the X-axis signal. Vector V of these signals is matrix multiplied electronically in FIG. 41 according to the rotation product R*V, using rotation matrix R expressed by Equation (21).

$$R = \begin{bmatrix} \cos\varphi & (\sin\varphi\sin\theta) & (\sin\varphi\cos\theta) \\ 0 & \cos\theta & -\sin\theta \\ -\sin\varphi & (\cos\varphi\sin\theta) & (\cos\varphi\cos\theta) \end{bmatrix} \quad (21)$$

In various embodiments, the axis rotations are suitably customized by the processing for the type of signal output (e.g., blood flow, heart sounds) which is to be maximized for a given purpose. The angles θ and φ are each varied by a given feedback control circuit 995.i to maximize the desired type of signal output to which that feedback control circuit is applied.

In FIG. 41, for instance, some embodiments execute a feedback control 995.1 to thus maximize the heart sound signal for the heart monitoring path, and the axes-rotation parameters for the rotation process 990.1 for a feedback loop 990.1, 130, 140, . . . , 995.1 established either as a configuration routine before run-time, or dynamically at run-time. The feedback loop rotates the axes to deliver a linear combination of Z-axis and Y-axis (and X-axis can also be useful) as an input in place of the raw Z-axis signal in FIGS. 31 and 36A to the Savitzky-Golay polynomial filter 130 for the Z-axis to maximize the amplitude of the S1 peaks at the output of the Folded Correlation, for heart sound and heart rate monitoring purposes.

Analogously, in FIG. 41, some embodiments additionally or alternatively execute a feedback loop 990.2, 930, . . . , 995.2 by independently rotating axes to deliver a linear combination of X-axis and Y-axis (and Z-axis can also be useful) as an input in place of the raw Y-axis signal in FIGS. 31 and 36B to the Savitzky-Golay polynomial filter 930 for the Y-axis, to maximize the blood flow signal peak amplitude PAmp of FIGS. 29 and 32. To save some processing, some embodiments can perform the blood flow axes-rotation on the X and Y axes only (φ=0 in Equation (21)) for the blood flow signal, see Equation (22).

$$R(\varphi = 0) = \begin{bmatrix} 1 & 0 & 0 \\ 0 & \cos\theta & -\sin\theta \\ 0 & \sin\theta & \cos\theta \end{bmatrix} \quad (22)$$

Note that the rotation matrix R of Equation (21) is the product of a tilt matrix M of Equation (23) with the XY rotation matrix of Equation (22):

$$M = \begin{bmatrix} \cos\varphi & 0 & \sin\varphi \\ 0 & 1 & 0 \\ -\sin\varphi & 0 & \cos\varphi \end{bmatrix} \quad (23)$$

In another way to save some processing, some embodiments can use one rotation 990 and one feedback control 995 operating in response to signals jointly, like heart sounds amplitude and/or blood flow signal amplitude. Various modes of operation and configuration can be activated or disabled by means of one or more control registers with bits or bit fields for the various operations and configurations. A manual mode, if activated, can override the feedback controls and let a clinician manually optimize the virtual rotations while examining signals like those of FIG. 29 on the computer display of FIG. 25.

Some embodiments also include an electronic compass physically included into the assembly of FIGS. 40A, 40B for supporting location-based services by the sensor assembly. An e-compass and signals therefrom are provided, calibrated and processed using the teachings of US patent application "Processes for More Accurately Calibrating E-Compass for Tilt Error, Circuits, and Systems" Ser. No. 12/398,696 (TI-65997) filed Mar. 5, 2009, and which is incorporated herein by reference in its entirety.

Figure 42:
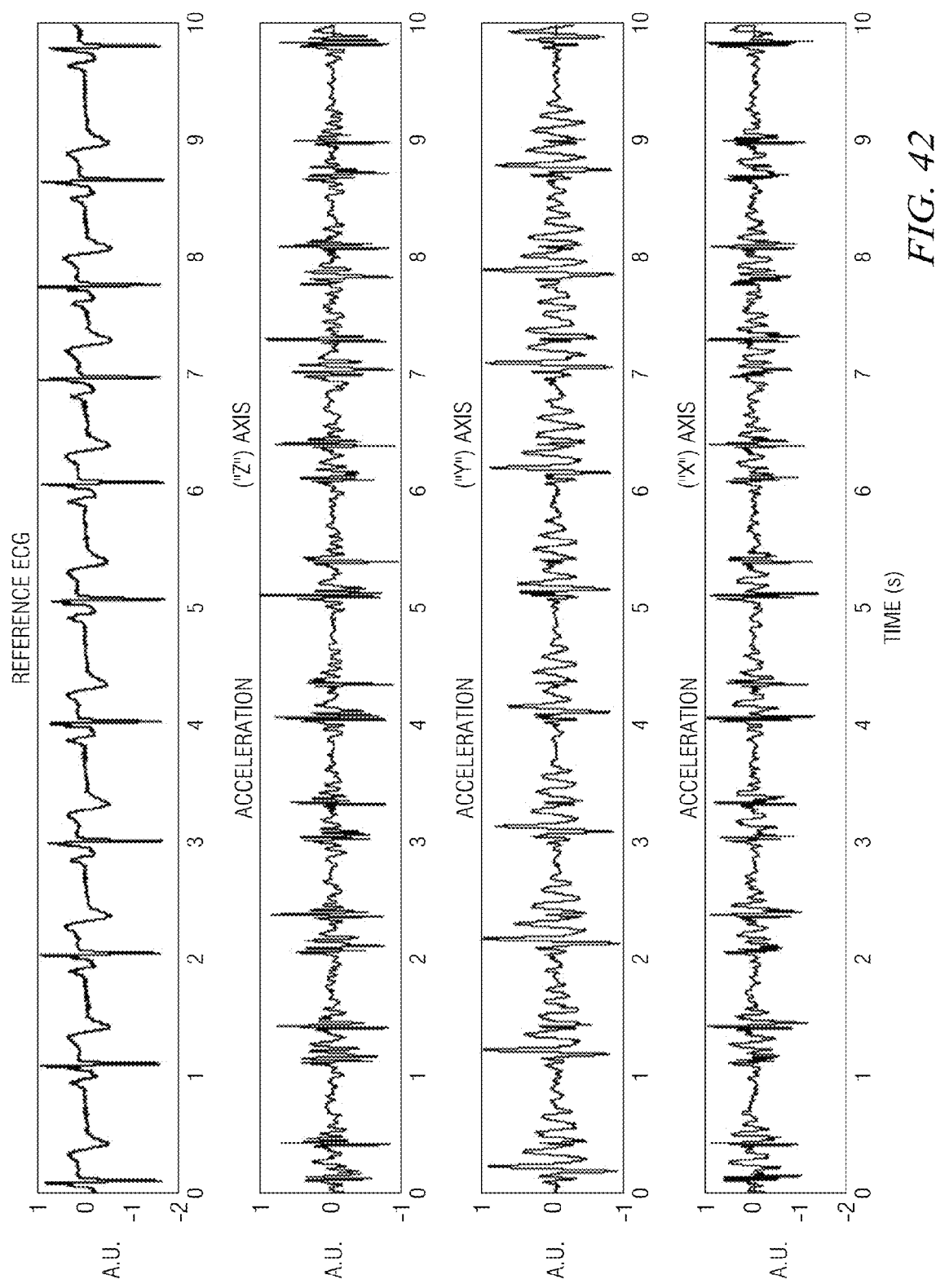
FIG. 42 is a voltage-versus-time graph of four concurrent waveforms including reference ECG, acceleration along a dorso-ventral axis (Z-axis), acceleration along a superior-inferior axis (Y-axis) and acceleration along a dextro-sinistral axis (X-axis), the various acceleration signals for use in the circuit FIG. 41 and circuits of other Figures.

FIG. 42 shows four concurrent waveforms including reference ECG, acceleration along the dorso-ventral axis (Z-axis), acceleration along the superior-inferior axis (Y-axis) and acceleration along the dextro-sinistral axis (X-axis). Notice the relatively prominent heart peaks in the Z-axis and X-axis waveforms and the relatively prominent spindle-shaped oscillatory blood flow component in the Y-axis waveform. The latter three acceleration signals for X, Y, Z accelerometer axes are suitably applied in the circuit FIG. 41 and circuits and processes of any other Figures that can benefit from use of signals from two or three of the accelerometer axes. Some further embodiments provide circuitry and/or firmware that fuses hemodynamic and acoustic signatures from multiple-axis signals and/or interaxis cross-talk using approaches like blind source separation, principal component analysis PCA and/or independent component analysis ICA.

Various embodiments as described herein are manufactured in a process that prepares a particular design and printed wiring board (PWB) of the system unit and has an applications processor coupled to a modem, together with one or more peripherals coupled to the processor and a user interface coupled to the processor or not, as the case may be. A storage, such as SDRAM and Flash memory is coupled to the system (e.g., FIG. 39) and has tables, configuration and parameters and an operating system OS, protected applications (PPAs and PAs), and other supervisory software. System testing tests operations of the integrated circuit(s) and system in actual application for efficiency and satisfactory operation of fixed or mobile video display for continuity of data transfer and content, display and other user interface operation and other such operation that is apparent to the human user and can be evaluated by system use. If further increased efficiency is called for, parameter(s) are reconfigured for further testing. Adjusted parameter(s) are loaded into the Flash memory or otherwise, components are assembled on PWB to produce resulting system units.

The electronic monitoring devices and processing described herein is suitably supported by any one or more of RISC (reduced instruction set computing), CISC (complex instruction set computing), DSP (digital signal processors), microcontrollers, PC (personal computer) main microprocessors, math coprocessors, VLIW (very long instruction word), SIMD (single instruction multiple data) and MIMD (multiple instruction multiple data) processors and coprocessors as cores or standalone integrated circuits, and in other integrated circuits and arrays. Other types of integrated circuits are applied, such as ASICs (application specific integrated circuits) and gate arrays and all circuits to which the advantages of the improvements described herein commend their use.

In addition to inventive structures, devices, apparatus and systems, processes are represented and described using any and all of the block diagrams, logic diagrams, and flow diagrams herein. Block diagram blocks are used to represent both structures as understood by those of ordinary skill in the art as well as process steps and portions of process flows. Similarly, logic elements in the diagrams represent both electronic structures and process steps and portions of process flows. Flow diagram symbols herein represent process steps and portions of process flows in software and hardware embodiments as well as portions of structure in various embodiments of the invention.

Processing circuitry comprehends digital, analog and mixed signal (digital/analog) integrated circuits, ASIC circuits, PALs, PLAs, decoders, memories, and programmable and nonprogrammable processors, microcontrollers and other circuitry. Internal and external couplings and connections can be ohmic, capacitive, inductive, photonic, and direct or indirect via intervening circuits or otherwise as desirable. Process diagrams herein are representative of flow diagrams for operations of any embodiments whether of hardware, software, or firmware, and processes of manufacture thereof. Flow diagrams and block diagrams are each interpretable as representing structure and/or process. While this invention has been described with reference to illustrative embodiments, this description is not to be construed in a limiting sense. Various modifications and combinations of the illustrative embodiments, as well as other embodiments of the invention may be made. The terms including, includes, having, has, with, or variants thereof are used in the detailed description and/or the claims to denote non-exhaustive inclusion in a manner similar to the term comprising. The appended claims and their equivalents should be interpreted to cover any such embodiments, modifications, and embodiments as fall within the scope of the invention.

What is claimed is:

1. A process of operating a data acquisition and signal processing unit comprising:
   A. receiving acceleration signals that contain cardiac activity signals at an input of the unit;
   B. digitally low pass filtering the acceleration signals with a filter cutoff of substantially a power line frequency to obtain filtered accelerometer signals;
   C. decimating the filtered accelerometer signals by a factor of 10 to obtain decimated filtered accelerometer signals, x(i);
   D. Savitzky-Golay polynomial smoothing filtering the decimated filtered accelerometer signals to obtain relatively slow-varying motion wander signals g(i);
   E. subtracting the slow-varying motion wander signals g(i) from the decimated filtered accelerometer signals, x(i) to obtain heart sound signals S1 and S2, r(i);
   F. generating envelope-processed residue signals R(i) from the heart sound signals S1 and S2, r(i);
   G. performing a folded correlation process of the envelope-processed residue signals R(i) to obtain folded correlation signals fc(i);
   H. locating peaks of the folded correlation signals fc(i) using an electronic amplitude-based peak picking process;
   I. counting the peaks to calculate heart rate signals; and
   J. providing calculated heart rate signals to an output of the unit.

2. The process of claim 1 in which digitally low pass filtering the acceleration signals includes filtering with a rolloff frequency less than 60 Hertz to attenuates 60 Hertz power line interference, and a rolloff frequency less than 50 Hertz to attenuate using 50 Hertz power line interference.

3. The process of claim 1 including processing the residue signals R(i) in overlapping frames indexed (i).

4. The process of claim 1 in which the Savitzky-Golay polynomial smoothing filtering uses 28th order and 401 point frame.

5. The process of claim 1 in which the folded correlation process includes folding heart monitoring residue samples R(i) from the later half of a frame around the center heart monitoring sample R(i) in the frame and multiplied by dot product with heart monitoring residue samples R(i) in the earlier half of the frame to obtain an instant (i) of an input residue signal stream R(i) in the center of the frame.

6. The process of claim 1 including performing at least some of the steps on a computer.

* * * * *